United States Patent
Wester et al.

(10) Patent No.: US 11,497,819 B2
(45) Date of Patent: Nov. 15, 2022

(54) PSMA LIGANDS FOR IMAGING AND ENDORADIOTHERAPY

(71) Applicant: Technische Universität München, Munich (DE)

(72) Inventors: Hans-Jurgen Wester, Schweitenkirchen (DE); Alexander Schmidt, Munich (DE); Mara Parzinger, Munich (DE)

(73) Assignee: Technische Universität München, Munich (DE)

( * ) Notice: Subject to any disclaimer, the term of this patent is extended or adjusted under 35 U.S.C. 154(b) by 0 days.

(21) Appl. No.: 16/765,729

(22) PCT Filed: Dec. 11, 2018

(86) PCT No.: PCT/EP2018/084399
§ 371 (c)(1),
(2) Date: May 20, 2020

(87) PCT Pub. No.: WO2019/115547
PCT Pub. Date: Jun. 20, 2019

(65) Prior Publication Data
US 2020/0297876 A1   Sep. 24, 2020

(30) Foreign Application Priority Data
Dec. 11, 2017 (EP) .................. 17206510

(51) Int. Cl.
| | | |
|---|---|---|
| *A61K 51/00* | (2006.01) | |
| *A61M 36/14* | (2006.01) | |
| *A61K 51/04* | (2006.01) | |
| *A61P 35/00* | (2006.01) | |
| *C07D 257/02* | (2006.01) | |

(52) U.S. Cl.
CPC .......... *A61K 51/0482* (2013.01); *A61P 35/00* (2018.01); *A61K 2121/00* (2013.01); *A61K 2123/00* (2013.01); *C07D 257/02* (2013.01)

(58) Field of Classification Search
None
See application file for complete search history.

(56) References Cited

FOREIGN PATENT DOCUMENTS

| | | |
|---|---|---|
| WO | WO-2017/116994 A1 | 7/2017 |
| WO | WO-2017/165473 A1 | 9/2017 |
| WO | WO-2019/115405 A1 | 6/2019 |
| WO | WO-2019/115547 A1 | 6/2019 |
| WO | WO-2019/118298 A1 | 6/2019 |

OTHER PUBLICATIONS

Chatalic et al. (Theranostics 2016, 6, 849-861).*
Lutje et al. (Theranostics 2015, 5, 1388-1401).*
Weineisen et al. (EJNMMI Research 2014, 4, 63; pp. 1-15).*
Third Party Observation for EP Application No. EP 18812215.4 dated Apr. 21, 2021.
Choy et al., "177Lu-Labeled Phosphoramidate-Based PSMA Inhibitors: The Effect of an Albumin Binder on Biodistribution and Therapeutic Efficacy in Prostate Tumor-Bearing Mice," Theranostics, 7(7): 1928-1939 (2017).
International Search Report and Written Opinion for International Application No. PCT/EP2018/084399 dated Mar. 1, 2019.
Benesova et al., "Linker Modification Strategies To Control the Prostate-Specific Membrane Antigen (PSMA)-Targeting and Pharmacokinetic Properties of DOTA Conjugated PSMA Inhibitors," Journal of Medicial Chemistry, 59: 1761-1775 (2016).
Chilean Examination Report and English Translation for CL Application No. 202001542 dated Apr. 5, 2021, 21 pages.
Chilean Search Report and English Translation for CL Application No. 202001542 dated Apr. 5, 2021, 7 pages.
Eder et al., "68Ga-Complex Lipophilicity and the Targeting Property of a Urea-Based PSMA Inhibitor for PET Imaging," Bioconjugate Chemistry, 23: 688-697 (2012).
Robu et al., "Preclinical Evaluation and First Patient Application of 99mTc-PSMA-I&S for SPECT Imaging and Radioguided Surgery in Prostate Cancer," J. Nucl. Med., 58(2): 235-242 (2017).
Third Party Observation for EP Application No. EP 18812215.4 dated Jan. 27, 2021.
Gourni et al., "Metal-Based PSMA Radioligands," Molecules, 22(4): Article 534 pp. 34 pages (2017).
Schmidt., "Structural modifications of PSMA ligands to optimize their pharmacokinetics," Dissertation Technischen Universitat: 221 pages (2017).

* cited by examiner

*Primary Examiner* — Michael G. Hartley
*Assistant Examiner* — Melissa J Perreira
(74) *Attorney, Agent, or Firm* — Foley Hoag LLP; David P. Halstead

(57) ABSTRACT

The present invention relates to compounds which bind and/or inhibit prostate-specific membrane antigen (PSMA) comprising at least one group electron dense substituent (EDS), and at least one moiety which is amenable to radiolabeling; and therapeutic and diagnostic uses thereof.

37 Claims, 7 Drawing Sheets

[⁶⁸Ga]PSMA-62

Figure 1:
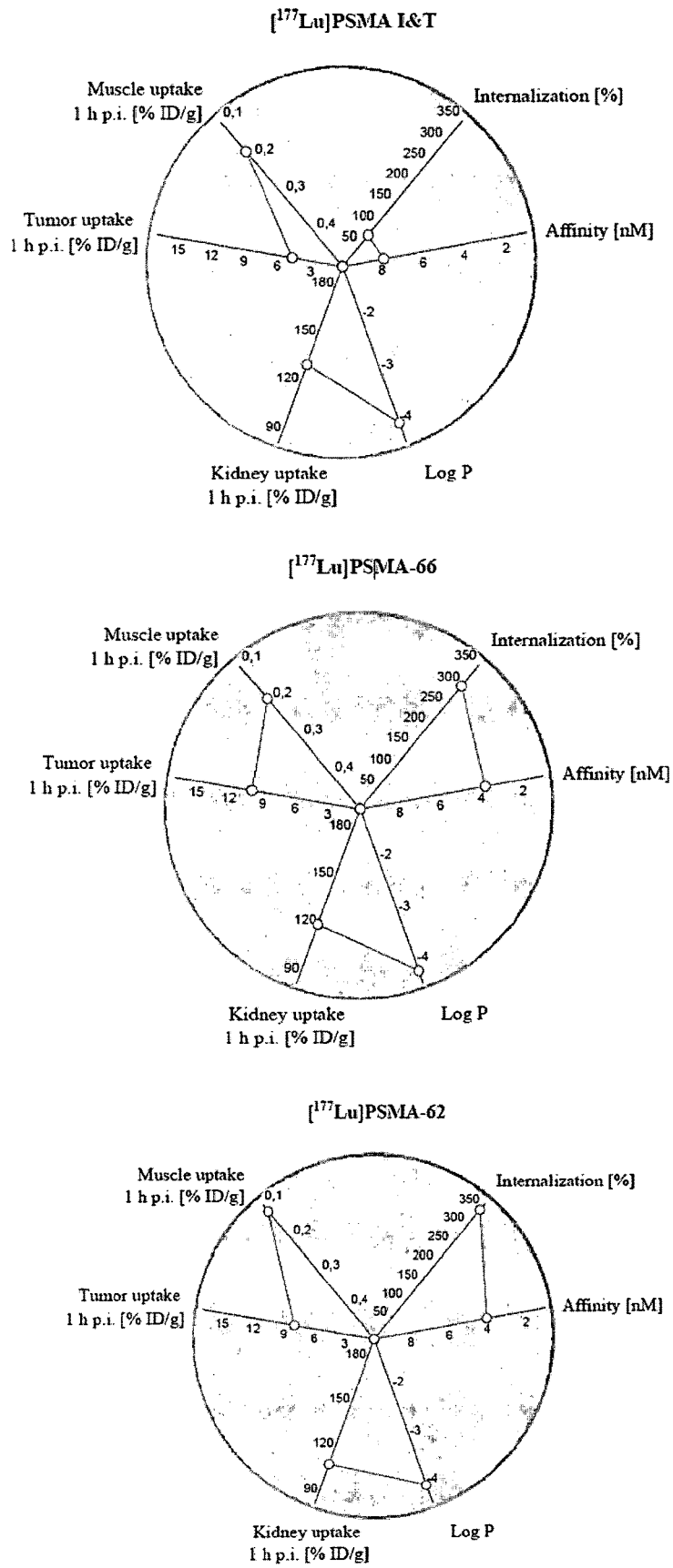

DOTAGA-F(4-
NH$_2$)y-2-nal-
k(d[$N^5$-orn-$C^4$-
EuE]-TMA)

[⁶⁸Ga]PSMA-66

DOTAGA-
Dap(TMA)y-2-
nal-k(d[$N^5$-orn-
$C^4$-EuE]-TMA)

PSMA LIGANDS FOR IMAGING AND ENDORADIOTHERAPY

RELATED APPLICATIONS

This application is a § 371 national-stage application based on PCT/EP2018/084399, filed Dec. 11, 2018 which claims the benefit of priority to European Patent Office Application No. 17206510.4 filed Dec. 11, 2017, both of which is hereby incorporated by reference in their entirety.

The present disclosure relates to imaging and endoradiotherapy of diseases involving prostate-specific membrane antigen (PSMA). Provided are compounds which bind or inhibit PSMA and furthermore carry at least one moiety which is amenable to radiolabeling. Provided are also medical uses of such compounds.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Prostate Cancer (PCa) remained over the last decades the most common malignant disease in men with high incidence for poor survival rates. Due to its overexpression in prostate cancer (Silver, D. A., et al., *Prostate-specific membrane antigen expression in normal and malignant human tissues*. Clinical Cancer Research, 1997. 3(1): p. 81-85), prostate-specific membrane antigen (PSMA) or glutamate carboxypeptidase II (GCP II) proved its eligibility as excellent target for the development of highly sensitive radiolabeled agents for endoradiotherapy and imaging of PCa (Afshar-Oromieh, A., et al., *The diagnostic value of PET/CT imaging with the 68Ga-labelled PSMA ligand HBED-CC in the diagnosis of recurrent prostate cancer*. European journal of nuclear medicine and molecular imaging, 2015. 42(2): p. 197-209; Benešová, M., et al., *Preclinical Evaluation of a Tailor-Made DOTA-Conjugated PSMA Inhibitor with Optimized Linker Moiety for Imaging and Endoradiotherapy of Prostate Cancer*. Journal of Nuclear Medicine, 2015. 56(6): p. 914-920; Robu, S., et al., *Preclinical evaluation and first patient application of 99mTc-PSMA-I&S for SPECT imaging and radioguided surgery in prostate cancer*. Journal of Nuclear Medicine, 2016: p. jnumed. 116.178939; Weineisen, M., et al., *Development and first in human evaluation of PSMA I&T-A ligand for diagnostic imaging and endoradiotherapy of prostate cancer*. Journal of Nuclear Medicine, 2014. 55(supplement 1): p. 1083-1083; Rowe, S., et al., *PET imaging of prostate-specific membrane antigen in prostate cancer: current state of the art and future challenges*. Prostate cancer and prostatic diseases, 2016; Maurer, T., et al., *Current use of PSMA-PET in prostate cancer management*. Nature Reviews Urology, 2016). Prostate-specific membrane antigen is an extracellular hydrolase whose catalytic center comprises two zinc(II) ions with a bridging hydroxido ligand. It is highly upregulated in metastatic and hormone-refractory prostate carcinomas, but its physiologic expression has also been reported in kidneys, salivary glands, small intestine, brain and, to a low extent, also in healthy prostate tissue. In the intestine, PSMA facilitates absorption of folate by conversion of pteroylpoly-γ-glutamate to the pteroylglutamate (folate). In the brain, it hydrolyses N-acetyl-Laspartyl-L-glutamate (NAAG) to N-acetyl-L-aspartate and glutamate. The enzymatic function of PSMA in normal and diseased prostate has yet not been clarified.

PSMA targeting molecules usually comprise a binding unit that encompasses a zinc-binding group (such as urea (Zhou, J., et al., *NAAG peptidase inhibitors and their potential for diagnosis and therapy*. Nature Reviews Drug Discovery, 2005. 4(12): p. 1015-1026), phosphinate or phosphoramidate) connected to a P1' glutamate moiety, which warrants high affinity and specificity to PSMA and is typically further connected to an effector functionality (Machulkin, A. E., et al., *Small-molecule PSMA ligands. Current state, SAR and perspectives*. Journal of drug targeting, 2016: p. 1-15). The effector part is more flexible and to some extent tolerant towards structural modifications. The entrance tunnel of PSMA accommodates two other prominent structural features, which are important for ligand binding. The first one is an arginine patch, a positively charged area at the wall of the entrance funnel and the structural explanation for the preference of negatively charged functionalities at the P1 position of PSMA. Upon binding the concerted repositioning of the arginine side chains can lead to the opening of an S1 hydrophobic accessory pocket, the second important structure, that has been shown to accommodate an iodobenzyl group of several urea based inhibitors, thus contributing to their high affinity for PSMA (Barinka, C., et al., *Interactions between Human Glutamate Carboxypeptidase II and Urea-Based Inhibitors: Structural Characterization†*. Journal of medicinal chemistry, 2008. 51(24): p. 7737-7743).

Zhang et al. discovered a remote binding site of PSMA, which can be employed for bidentate binding mode (Zhang, A. X., et al., *A remote arene-binding site on prostate specific membrane antigen revealed by antibody-recruiting small molecules*. Journal of the American Chemical Society, 2010. 132(36): p. 12711-12716). The so called arene-binding site is a simple structural motif shaped by the side chains of Arg463, Arg511 and Trp541, and is part of the PSMA entrance lid. The engagement of the arene-binding site by a distal inhibitor moiety can result in a substantial increase in the inhibitor affinity for PSMA due to avidity effects. PSMA I&T (see FIG. 1) was developed with the intention to interact this way with PSMA, albeit no crystal structure analysis of binding mode is available. A necessary feature according to Zhang et al. is a linker unit (suberic acid in the case of PSMA I&T) which facilitates an open conformation of the entrance lid of PSMA and thereby enabling the accessibility of the arene-binding site. It was further shown that the structural composition of the linker has a significant impact on the tumor-targeting and biologic activity as well as on imaging contrast and pharmacokinetics (Liu, T., et al., *Spacer length effects on in vitro imaging and surface accessibility of fluorescent inhibitors of prostate specific membrane antigen*. Bioorganic & medicinal chemistry letters, 2011. 21(23): p. 7013-7016), properties which are crucial for both high imaging quality and efficient targeted endoradiotherapy.

Two categories of PSMA targeting inhibitors are currently used in clinical settings. On the one side are tracer with chelating units for radionuclide complexation as PSMA I&T or related compounds (Kiess, A. P., et al., *Prostate-specific membrane antigen as a target for cancer imaging and therapy*. The quarterly journal of nuclear medicine and molecular imaging: official publication of the Italian Association of Nuclear Medicine (AIMN)[and] the International Association of Radiopharmacology (IAR), [and] Section of the Society of . . . 2015. 59(3): p. 241). On the other side are small molecules, comprising a targeting unit and effector molecules. Depending on the used radionuclide/halogen, the radiolabeled PSMA inhibitors may be used for imaging or endoradiotherapy. Among small molecule inhibitors with chelators for imaging, the most often used agents for selective PSMA imaging are PSMA HBED-CC (Eder, M., et al., *68Ga-complex lipophilicity and the targeting property of a urea-based PSMA inhibitor for PET imaging*. Bioconjugate chemistry, 2012. 23(4): p. 688-697), PSMA-617 (Benešová, M., et al., *Preclinical Evaluation of a Tailor-Made DOTA-Conjugated PSMA Inhibitor with Optimized Linker Moiety for Imaging and Endoradiotherapy of Prostate Cancer*. Journal of Nuclear Medicine, 2015. 56(6): p. 914-920) and PSMA I&T (Weineisen, M., et al., *Development and first in human evaluation of PSMA I&T-A ligand for diagnostic imaging and endoradiotherapy of prostate cancer*. Journal of Nuclear Medicine, 2014. 55(supplement 1): p. 1083-1083). PSMA HBED-CC, or PSMA-11 was one the first PSMA inhibitors and is currently used for imaging since therapeutic applications are not possible with the chelator HBED-CC. However, due to the unique physical characteristics and the advantages of 18F for PET imaging, like the longer half-life, the low positron energy, which results in higher image resolution and the possibility for largescale production in a cyclotron, several groups have focused on the development of $^{18}$F-labeled urea-based Inhibitors for PCa imaging. The $^{18}$F-labeled urea-based PSMA inhibitor [$^{18}$F]DCFPyl demonstrated promising results in detection of primary and metastatic PCa (Rowe, S. P., et al., *PSMA-Based [18F] DCFPyL PET/CT Is Superior to Conventional Imaging for Lesion Detection in Patients with Metastatic Prostate Cancer*. Molecular Imaging and Biology, 2016: p. 1-9) and superiority to [$^{68}$Ga]PSMA-HBED-CC in a comparative study (Dietlein, M., et al., *Comparison of [18F] DCFPyL and [68Ga] Ga-PSMA-HBED-CC for PSMA-PET imaging in patients with relapsed prostate cancer*. Molecular Imaging and Biology, 2015. 17(4): p. 575-584).

PSMA DKFZ 617 (Benešová, M., et al., *Preclinical Evaluation of a Tailor-Made DOTA-Conjugated PSMA Inhibitor with Optimized Linker Moiety for Imaging and Endoradiotherapy of Prostate Cancer*. Journal of Nuclear Medicine, 2015. 56(6): p. 914-920, Becker, A., et al., *Nephro-and hepatotoxicity after radioligand therapy of metastatic castrate-resistant prostate cancer with 177Lu-PSMA-617*. Journal of Nuclear Medicine, 2016. 57(supplement 2): p. 1430-1430; Rahbar, K., et al., *Response and tolerability of a single dose of 177Lu-PSMA-617 in patients with metastatic castration-resistant prostate cancer: a multicenter retrospective analysis*. Journal of Nuclear Medicine, 2016: p. jnumed. 116.173757) and PSMA I&T (Weineisen, M., et al., *Development and first in human evaluation of PSMA I&T-A ligand for diagnostic imaging and endoradiotherapy of prostate cancer*. Journal of Nuclear Medicine, 2014. 55(supplement 1): p. 1083-1083, Eiber, M., et al., *Systemic radioligand therapy with 177Lu-PSMA I&T in patients with metastatic castration-resistant prostate cancer*. Journal of Nuclear Medicine, 2016. 57(supplement 2): p. 61-61; Schottelius, M., et al., *[111In] PSMA-I&T: expanding the spectrum of PSMA-I&T applications towards SPECT and radioguided surgery*. EJNMMI research, 2015. 5(1): p. 1) are applied in clinical settings for palliative treatment of prostate cancer patients. The chelating unit DOTA and the related DOTAGA, allow not only imaging but also therapeutical applications, since the scope for possible radiometal chelation encompasses $^{111}$In, $^{177}$Lu, $^{90}$Y and $^{213}$Bi amongst others. [$^{111}$In]PSMA I&T was already clinically implemented for radioguided surgery to assist the surgeon during excision of the malignant tissue (Schottelius, M., et al., *[111In] PSMA-I&T: expanding the spectrum of PSMA-I&T applications towards SPECT and radioguided surgery*. EJNMMI research, 2015. 5(1): p. 1). Likewise, the recent developed and clinically tested PSMA Inhibitor PSMA I&S (imaging and surgery) demonstrated highly encouraging results (Robu, S., et al., *Preclinical evaluation and first patient application of 99mTc-PSMA-I&S for SPECT imaging and radioguided surgery in prostate cancer*. Journal of Nuclear Medicine, 2016: p. jnumed. 116.178939).

Endoradiotherapeutic approaches with [$^{177}$Lu]PSMA I&T demonstrated efficiency, tolerability and high safety potential in patients receiving up to four cycles with 7.4 GBq. The obtained dosimetric values for organ radiation revealed, that especially the kidneys and the salivary glands receive the highest dose after tumor lesions. Similar radiation values were shown for PSMA DKFZ 617 and [$^{18}$F] DCFPyL (Rowe, S. P., et al., *PSMA-Based [18F] DCFPyL PET/CT Is Superior to Conventional Imaging for Lesion Detection in Patients with Metastatic Prostate Cancer*. Molecular Imaging and Biology, 2016: p. 1-9; Delker, A., et al., *Dosimetry for 177Lu-DKFZ-PSMA-617: a new radiopharmaceutical for the treatment of metastatic prostate cancer*. European journal of nuclear medicine and molecular imaging, 2016. 43(1): p. 42-51; Kabasakal, L., et al., *Pre-therapeutic dosimetry of normal organs and tissues of 177Lu-PSMA-617 prostate-specific membrane antigen (PSMA) inhibitor in patients with castration-resistant prostate cancer*. European journal of nuclear medicine and molecular imaging, 2015. 42(13): p. 1976-1983; Yadav, M. P., et al., *177Lu-DKFZ-PSMA-617 therapy in metastatic castration resistant prostate cancer: safety, efficacy, and quality of life assessment*. European Journal of Nuclear Medicine and Molecular Imaging, 2016: p. 1-11). These elevated numbers are explainable by the physiologic expression of PSMA (Silver, D. A., et al., *Prostate-specific membrane antigen expression in normal and malignant human tissues*. Clinical Cancer Research, 1997. 3(1): p. 81-85) and the renal excretion of the radiolabeled compound. The occasional occurring renal and hematological toxicities after administration are usually reversible, although is legitimate concern about chronic toxicity especially in patients with overall long survival rates, like in PCa patients. Therefore, a suitable concept is needed to reduce the unwanted radiation and simultaneously to increase the tumor uptake.

In view of the above, the technical problem underlying the present invention can be seen in the provision of means and methods of alleviating radiation-induced side effects of PSMA-targeting radiolabeled diagnostics and therapeutics. A further technical problem can be seen in the provision of means and methods to increase tumor uptake of such diagnostics and therapeutics. More generally speaking, the technical problem can be seen in the provision of improved PSMA binding agents.

The technical problem is solved by the subject-matter summarized in the attached claims and explained in further detail below.

In particular, the present invention provides, in a first aspect, a compound of formula (I), or a pharmaceutically acceptable salt thereof, $$\text{(I)}$$

[Chemical structure of formula (I) showing:
HOOC—(CH₂)ₘ—CH(R¹ᴸ)—R²ᴸ(=O)—R³ᴸ(COOH) branch and
Rᴹ—X³—[(CH₂)ₚ—CH((CH₂)_q—R⁴)—C(=O)—NH—CH(R³)—C(=O)]ᵣ—NH—CH(R²)—X²—L¹—X¹—(CH₂)ₙ— connecting to the above branch with COOH]

wherein:

m is an integer of 2 to 6, preferably 2 to 4, more preferably 2;

n is an integer of 2 to 6, preferably 2 to 4, more preferably 2 or 4;

$R^{1L}$ is $CH_2$, NH or O, preferably NH;

$R^{2L}$ is C or P(OH), preferably C;

$R^{3L}$ is $CH_2$, NH or O, preferably NH;

$X^1$ is selected from an amide bond, an ether bond, a thioether bond, an ester bond, a thioester bond, a urea bridge, and an amine bond, and is preferably an amide bond;

$L^1$ is a divalent linking group with a structure selected from an oligoamide, an oligoether, an oligothioether, an oligoester, an oligothioester, an oligourea, an oligo(ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo(ether-urea), an oligo(thioether-ester), an oligo(thioether-thioester), an oligo(thioether-urea), an oligo(ester-thioester), an oligo(ester-urea), and an oligo(thioester-urea), preferably with a structure selected from an oligoamide and an oligo(ester-amide), which linking group may carry a group EDS;

$X^2$ is selected from an amide bond, an ether bond, a thioether bond, an ester bond, a thioester bond, a urea bridge, and an amine bond, and is preferably an amide bond;

$R^2$ is an optionally substituted aryl group or an optionally substituted aralkyl group, which aryl group or aralkyl group may be substituted on its aromatic ring with one or more substituents selected from halogen, preferably I, and —OH;

$R^3$ is an optionally substituted aryl group or an optionally substituted aralkyl group, which aryl group or aralkyl group may be substituted on its aromatic ring with one or more substituents selected from halogen, preferably I, and —OH;

r is 0 or 1, preferably 1;

p is 0 or 1;

q is 0 or 1;

and preferably p+q=1;

$R^4$ is selected from an aryl group and a group EDS;

$X^3$ is selected from an amide bond, an ether bond, a thioether bond, an ester bond, a thioester bond, a urea bridge, an amine bond, and a group of the formula

[Chemical structure showing a group with C(=O)NH—CH₂— connected to a triazole ring (N=N)]

, wherein the marked bond at the carbonyl group attaches $X^3$ to $R^M$ and the other marked bond attaches $X^3$ to the remainder of the compound of formula (I);

and is preferably an amide bond;

$R^M$ is a marker group which comprises a chelating group optionally containing a chelated non-radioactive or radioactive cation;

and wherein the group EDS is contained at least once in the compound of formula (I) and has a structure selected from (E-1A), (E-1B), (E-2A) and (E-2B):

(E-1A)

[Phenyl ring with $(R^{5A})_s$ substituent]

(E-2A)

[Phenyl ring with HN—C(=O)— group and $(R^{6A})_t$ substituent]

(E-1B)

[Phenyl ring with $(R^{5B})_s$ substituent]

(E-2B)

[Phenyl ring with HN—C(=O)— group and $(R^{6B})_t$ substituent]

wherein

〜〜〜 marks the bond which attaches the group EDS, to the remainder of the compound of formula (I);

s is 1, 2 or 3, preferably 1 or 2, and more preferably 1;
t is 1, 2 or 3, preferably 1 or 2, and more preferably 2;
$R^{5A}$ is, independently for each occurrence for s>1, an electron withdrawing substituent, which is preferably selected from —$NO_2$ and —COOH, and which is more preferably —COOH, and wherein the bond between $R^{5A}$ and the phenyl ring indicates that the s groups $R^{5A}$ replace s hydrogen atoms at any position on the phenyl ring;

$R^{5B}$ is, independently for each occurrence for s>1, a substituent carrying an electron lone pair at the atom directly attached to the phenyl ring shown in formula (E-1B), which substituent is preferably selected from —OH and —$NH_2$, and which is more preferably —$NH_2$, and wherein the bond between $R^{5B}$ and the phenyl ring indicates that the s groups $R^{5B}$ replace s hydrogen atoms at any position on the phenyl ring;

$R^{6A}$ is, independently for each occurrence for t>1, an electron withdrawing substituent, which is preferably selected from —$NO_2$ and —COOH, and which is more preferably —COOH, and wherein the bond between $R^{6A}$ and the phenyl ring indicates that the t groups $R^{6A}$ replace t hydrogen atoms at any position on the phenyl ring; and $R^{6B}$ is, independently for each occurrence for t>1, a substituent carrying an electron lone pair at the atom directly attached to the phenyl ring shown in formula (E-1B), which substituent is preferably selected from —OH and —$NH_2$, and which is more preferably —OH, and wherein the bond between $R^{6B}$ and the phenyl ring indicates that the t groups $R^{6B}$ replace t hydrogen atoms at any position on the phenyl ring.

The introduction of an EDS substituent as shown above, wherein an aromatic ring carries one or more substituents with a high electron density selected from an electron withdrawing substituent and a substituent carrying an electron lone pair leads to several unexpected advantages. These advantages include increased affinity, improved internalization, elevated tumor cell retention, lower unspecific binding, reduced renal accumulation and an increased tumor uptake.

Especially the reduced unspecific uptake in organs other than prostate leads to less unwanted radiation and reduces radiation-induced side effects.

To exemplify these advantages, we refer to the properties of the particularly preferred compounds herein designated PSMA-71 and PSMA-66 which is discussed in more detail below.

In particular, nanomolar affinity (5.3±2.0 nM vs. 7.9±2.4 nM), drastically improved internalization (206.8±1.7% vs. 75.5±1.6%) demonstrate the superiority of [$^{177}$Lu]PSMA-71 when compared to [$^{177}$Lu]PSMA I&T. The biodistribution data revealed that [$^{177}$Lu]PSMA-71 exhibited markedly higher tumor (14.29±0.89 vs. 4.06±1.12% ID/g, respectively) uptake compared to [$^{177}$Lu]PSMA I&T while the renal accumulation was similar (32.36±2.49 vs. 34.66±17.20% ID/g, respectively).

Similarly, lower nanomolar affinity (3.8±0.3 nM vs. 7.9±2.4 nM), drastically improved internalization (297.8±2.0% vs. 75.5±1.6%), elevated in vitro tumor cell retention (90.1±3.5% vs. 62.8±0.4%, 60 min incubation) together with lower unspecific binding in vivo, reduced renal accumulation (117.5±6.9% ID/g vs. 128.9±10.7% ID/g) and a more than twofold increase in tumor uptake (10.0±0.4% ID/g vs. 4.7±1.0% ID/g), demonstrate the superiority of [$^{177}$Lu]PSMA-66 in direct comparison to [$^{177}$Lu]PSMA I&T.

As noted above, salts of the compounds of the invention including compounds of formula (I) (and including their preferred embodiments) are also suitable for use in the context of the invention. It will be understood that these salts are generally pharmaceutically acceptable salt forms of these compounds which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Further examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

It is understood that throughout the present specification the term "compound" encompasses solvates, polymorphs, prodrugs, codrugs, cocrystals, tautomers, racemates, enantiomers, or diastereomers or mixtures thereof unless mentioned otherwise.

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichiometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

The compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups.

To the extent compounds of the invention exhibit a pH-dependent charged state, it is understood that all possible charged states are embraced. A preferred pH range in this regard is from 0 to 14.

To the extent a compound according to the invention bears a net charge, it is understood that the compound is provided in electroneutral form. This is achieved by one or more counterions, preferred counterions being defined in relation to the term "salt" herein above.

In formula (I), m is an integer of 2 to 6. Preferably, m is 2 to 4, more preferably 2. $R^{1L}$ is $CH_2$, NH or O, preferably NH. $R^{2L}$ is C or P(OH), preferably C. $R^{3L}$ is $CH_2$, NH or O, preferably NH. Thus, compounds of formula (I) or their salts are also preferred wherein m is 2, $R^{1L}$ is NH, $R^{2L}$ is C, and $R^{3L}$ is NH.

n is an integer of 2 to 6, preferably 2 to 4, more preferably 2 or 4, and most preferably 2.

Thus, compounds of formula (I) or their salts are particularly preferred wherein m is 2, n is 2 or 4, $R^{1L}$ is NH, $R^{2L}$ is C, and $R^{3L}$ is NH. More preferred are compounds of formula (I) or their salts wherein m is 2, n is 2, $R^{1L}$ is NH, $R^{2L}$ is C, and $R^{3L}$ is NH.

$X^1$ in formula (I) is selected from an amide bond (i.e. —C(O)—NH—), an ether bond (i.e. —O—), a thioether bond (i.e. —S—), an ester bond (i.e. —C(O)—O—, a thioester bond (i.e. —C(S)—O— or —C(O)—S—), a urea bridge (i.e. —NH—C(O)—NH—), and an amine bond (i.e. —NH—). Preferred as $X^1$ is the amide bond.

Moreover, it is further preferred in formula (I) that either n is 2 and $X^1$ is the amide bond with the carbon atom of the amide bond —C(O)—NH— being attached to the group —(CH$_2$)$_n$—, or that n is 4 and $X^1$ is the amide bond with the carbon atom of the amide bond —C(O)—NH— being attached to the group —(CH$_2$)$_n$—. Among these, more preferred is the option that n is 2 and $X^1$ is the amide bond with the carbon atom of the amide bond —C(O)—NH— being attached to the group —(CH$_2$)$_n$—.

Thus, particularly preferred are compounds of formula (I) and their salts wherein, in formula (I), m is 2, n is 2, $R^{1L}$ is NH, $R^{2L}$ is C, $R^{3L}$ is NH, and $X^1$ is an amide bond with the carbon atom of the amide bond —C(O)—NH— being attached to the group —(CH$_2$)$_n$—.

$L^1$ in formula (I) is a divalent linking group with a structure selected from an oligoamide, an oligoether, an oligothioether, an oligoester, an oligothioester, an oligourea, an oligo(ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo(ether-urea), an oligo(thioether-ester), an oligo(thioether-thioester), an oligo(thioether-urea), an oligo(ester-thioester), an oligo(ester-urea), and an oligo(thioester-urea), preferably with a structure selected from an oligoamide and an oligo(ester-amide), and more preferably with an oligoamide structure, which linking group may carry a group EDS.

The term "oligo" as used in the definition of $L^1$ in the terms oligoamide, oligoether, oligothioether, oligoester, oligothioester, oligourea, oligo(ether-amide), oligo(thioether-amide), oligo(ester-amide), oligo(thioester-amide), oligo(urea-amide), oligo(ether-thioether), oligo(ether-ester), oligo(ether-thioester), oligo (ether-urea), oligo(thioether-ester), oligo(thioether-thioester), oligo(thioether-urea), oligo(ester-thioester), oligo(ester-urea), and oligo(thioester-urea) is preferably to be understood as referring to a group wherein 2 to 20, more preferably wherein 2 to 10 subunits are linked by the type of bonds specified in the same terms. As will be understood by the skilled reader, where two different types of bonds are indicated in brackets, both types of bonds are contained in the concerned group (e.g. in "oligo (ester-amide)", ester bonds and amide bonds are contained).

It is more preferred that $L^1$ has a structure selected from an oligoamide which comprises a total of 1 to 5, more preferably a total of 1 to 3, and most preferably a total of 1 or 2 amide bonds within its backbone, and an oligo(ester-amide) which comprises a total of 2 to 5, more preferably a total of 2 to 3, and most preferably a total of 2 amide and ester bonds within its backbone. In a particularly preferred embodiment, $L^1$ represents a divalent linking group with an oligoamide structure which comprises 1 or 2 amide bonds within its backbone.

Furthermore, $L^1$ may carry a group EDS (i.e. a group carrying a substituent with a high electron density or "electron dense substituent") as defined herein, i.e. a group EDS which is covalently attached to $L^1$. Preferably, the optional group EDS is attached as a substituent to the backbone of the divalent linking group $L^1$, $L^1$ having a structure as defined above selected from an oligoamide, an oligoether, an oligothioether, an oligoester, an oligothioester, an oligourea, an oligo(ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo(ether-urea), an oligo(thioether-ester), an oligo(thioether-thioester), an oligo(thioether-urea), an oligo (ester-thioester), an oligo(ester-urea), and an oligo(thioester-urea), preferably a structure selected from an oligoamide and an oligo(ester-amide), and most preferably an oligoamide structure, which backbone extends between $X^1$ and $X^2$ in the compound of formula (I). Also in this regard, the further preferred definitions for $L^1$ apply, i.e. it is more preferred that $L^1$ has a structure selected from an oligoamide which comprises a total of 1 to 5, more preferably a total of 1 to 3, and most preferably a total of 1 or 2 amide bonds within its backbone, and an oligo(ester-amide) which comprises a total of 2 to 5, more preferably a total of 2 to 3, and most preferably a total of 2 amide and ester bonds within its backbone. In a particularly preferred embodiment, $L^1$ represents a divalent linking group with an oligoamide structure which comprises 1 or 2 amide bonds within its backbone.

In accordance with the above, $L^1$ may carry one or more, e.g. 2 or 3, groups EDS. However, it is preferred that $L^1$ does not carry a group EDS, or that $L^1$ carries one group EDS, and it is more preferred that $L^1$ carries one group EDS.

If $L^1$ carries a group EDS (including the more preferred case that EDS carries one group EDS), it is preferred that the group EDS has a structure selected from (E-1A), (E-2A) and (E-2B). It is more preferred that the group EDS has a structure selected from (E-2A) and (E-2B), and most preferably it has the structure (E-2A).

As will be understood by the skilled reader, the indication that $L^1$ may carry a group EDS serves as information on a possible position of this group in the compounds in accordance with the invention. The fact that L may carry a group EDS does not impose a restriction on the presence of other groups that may be present e.g. as alternative or additional substituents on the backbone of $L^1$. For example, it is preferred that the linking group $L^1$ contains one or more, such as two, groups which are independently selected from —OH, —OCH$_3$, —COOH, —COOCH$_3$, —NH$_2$, and —NHC(NH)NH$_2$ attached as substituents to its backbone. More preferably, the linking group $L^1$ contains one or more, such as two, groups —COOH, attached as substituents to its backbone.

In formula (I), $X^2$ is selected from an amide bond, an ether bond, a thioether bond, an ester bond, a thioester bond, a urea bridge, and an amine bond, and is preferably an amide bond. It is more preferred that the nitrogen atom of the amide bond —C(O)—NH— is attached to $L^1$.

Thus, it is also preferred that $X^1$ and $X^2$ are both amide bonds, especially amide bonds arranged in the preferred orientations further defined above.

In line with the above, it is preferred that the moiety —$X^2$-$L^1$-$X^1$— in formula (I) has a structure selected from:

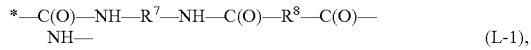

\*—C(O)—NH—$R^7$—NH—C(O)—$R^8$—C(O)—NH—     (L-1),

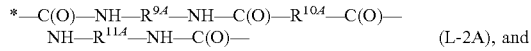

\*—C(O)—NH—$R^{9A}$—NH—C(O)—$R^{10A}$—C(O)—NH—$R^{11A}$—NH—C(O)—     (L-2A), and

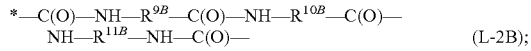

\*—C(O)—NH—$R^{9B}$—C(O)—NH—$R^{10B}$—C(O)—NH—$R^{11B}$—NH—C(O)—     (L-2B);

wherein the amide bond marked with \* is attached to the carbon atom carrying $R^2$ in formula (I), and wherein $R^7$, $R^8$, $R^{9A}$, $R^{9B}$, $R^{11A}$ and $R^{11B}$ are independently selected from optionally substituted C2 to C10 alkanediyl, preferably optionally substituted linear C2 to C10 alkanediyl, which alkanediyl groups may each be substituted by one or more substitutents independently selected from —OH, —OCH$_3$, —COOH, —COOCH$_3$, —NH$_2$, —NHC(NH)NH$_2$, and a group EDS, and $R^{10A}$ and $R^{10B}$ are selected from optionally substituted C2 to C10 alkanediyl, preferably optionally substituted linear C2 to C10 alkanediyl, and optionally substituted C6 to C10 arenediyl, preferably phenylene, which alkanediyl and arenediyl group may each be substituted by one or more substitutents independently selected from —OH, —OCH$_3$, —COOH, —COOCH$_3$, —NH$_2$, —NHC(NH)NH$_2$, and a group EDS. $R^{10A}$ is preferably optionally substituted C2 to C10 alkanediyl, more preferably optionally substituted linear C2 to C10 alkanediyl as defined above. $R^{10B}$ is preferably optionally substituted C6 to C10 arenediyl as defined above, more preferably a phenylene group, e.g. para-phenylene group.

In the groups of formula (L-1), (L-2A) and (L-2B), it is preferred that the optional substituent on $R^7$ is —COOH, that the optional substituent of $R^8$ is a group EDS, that the optional substituent on $R^{9A}$ and $R^{9B}$ is —COOH, that the optional substituent on $R^{10A}$ is a group EDS, and that the optional substituent on $R^{11A}$ and $R^{11B}$ is —COOH.

It is also preferred that each of the groups of formula (L-1) and (L-2A) carries a group EDS as at least one substituent, as explained above preferably as a substituent of $R^8$ and $R^{10A}$. Also in this context, it is preferred that the group EDS has a structure selected from (E-1A), (E-2A) and (E-2B). It is more preferred that the group EDS has a structure selected from (E-2A) and (E-2B), and most preferably it has the structure (E-2A).

Furthermore, it is preferred that the total number of carbon atoms in $R^7$ and $R^8$ of formula (L-1) is 6 to 20, more preferably 6 to 16, without carbon atoms contained in optional substituents, that the total number of carbon atoms in $R^{9A}$, $R^{10A}$ and $R^{11A}$ of formula (L-2A) is 6 to 20, more preferably 6 to 16, without carbon atoms contained in optional substituents, and that the total number of carbon atoms in $R^{9B}$, $R^{10B}$ and $R^{11B}$ of formula (L-2B) is 6 to 20, more preferably 6 to 16, without carbon atoms contained in optional substituents.

It will be understood from the information provided with respect to preferred meanings of n and $X^1$ above that it is still further preferred that —$X^2$-$L^1$-$X^1$— in formula (I) has a structure (L-1) if n is 4, and that —$X^2$-$L^1$-$X^1$— in formula (I) has a structure (L-2A) or (L-2B) if n is 2.

In line with the above definitions, it is even further preferred that the moiety —$X^2$-$L^1$-$X^1$— in formula (I) has a structure selected from:

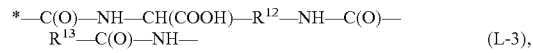

\*—C(O)—NH—CH(COOH)—$R^{12}$—NH—C(O)—$R^{13}$—C(O)—NH—     (L-3),

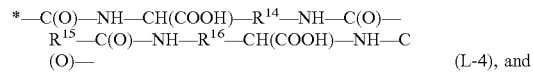

\*—C(O)—NH—CH(COOH)—$R^{14}$—NH—C(O)—$R^{15}$—C(O)—NH—$R^{16}$—CH(COOH)—NH—C(O)—     (L-4), and

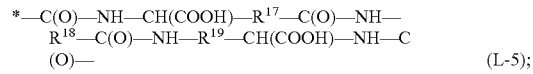

\*—C(O)—NH—CH(COOH)—$R^{17}$—C(O)—NH—$R^{18}$—C(O)—NH—$R^{19}$—CH(COOH)—NH—C(O)—     (L-5);

wherein the bond marked with \* is attached to the carbon atom carrying $R^2$ in formula (I), $R^{12}$ and $R^{14}$ are independently selected from linear C2 to C6 alkanediyl, preferably from linear C3 to C6 alkanediyl, $R^{13}$ is a linear C2 to C10 alkanediyl, preferably a linear C4 to C8 alkanediyl, $R^{15}$ and $R^{16}$ are independently selected from linear C2 to C6 alkanediyl, preferably from linear C2 to C4 alkanediyl, and wherein each of $R^{13}$ and $R^{15}$ may carry one group EDS as a substituent and preferably each of $R^{13}$ and $R^{15}$ carries one group EDS as a substituent, $R^{17}$ is a linear C2 to C6 alkanediyl, preferably a linear C2 to C4 alkanediyl, $R^{18}$ is a phenylene group, e.g. a para-phenylene group, and $R^{19}$ is a linear C2 to C6 alkanediyl, preferably a linear C2 to C4 alkanediyl.

Also in this context, it is preferred that the group EDS which may be attached to $R^{13}$ and $R^{15}$ has a structure selected from (E-1A), (E-2A) and (E-2B). It is more preferred that the group EDS has a structure selected from (E-2A) and (E-2B), and most preferably it has the structure (E-2A).

Furthermore, it is preferred that the total number of carbon atoms in $R^{12}$ and $R^{13}$ in formula (L-3), without carbon atoms contained in the group EDS as substituent, is 6 to 16, more preferably 6 to 14, and the total number of carbon atoms in $R^{14}$, $R^{15}$ and $R^{16}$ in formula (L-4), without carbon atoms contained in the group EDS as substituent, is 6 to 16, more preferably 6 to 14.

It will be understood from the information provided with respect to preferred meanings of n and $X^1$ above that it is particularly preferred that —$X^2$-$L^1$-$X^1$— in formula (I) has a structure (L-3) if n is 4, and that —$X^2$-$L^1$-$X^1$— in formula (I) has a structure (L-4) or (L-5) if n is 2.

It is specifically preferred that, in formula (I), n is 2 and the moiety —$X^2$-$L^1$-$X^1$— has one of the following structures:

*—C(O)—NH—CH(COOH)—(CH$_2$)$_4$—NH—C(O)—CH(EDS)—CH$_2$—C(O)—NH—(CH$_2$)$_3$—CH(COOH)—NH—C(O)—      (L-6)

*—C(O)—NH—CH(COOH)—(CH$_2$)$_2$—C(O)—NH-Ph-C(O)—NH—(CH$_2$)$_3$—CH(COOH)—NH—C(O)—      (L-7)

wherein the bond marked with * is attached to the carbon atom carrying $R^2$ in formula (I), EDS is a group EDS as defined herein, including its preferred embodiments, and Ph is a para-phenylene group.

Also in this context, it is preferred that the group EDS has a structure selected from (E-1A), (E-2A) and (E-2B). It is more preferred that the group EDS has a structure selected from (E-2A) and (E-2B), and most preferably it has the structure (E-2A).

In formula (I), $R^2$ is an optionally substituted aryl group or an optionally substituted aralkyl group, preferably an optionally substituted aralkyl group. As will be understood, the term "aralkyl group" as used herein refers to an alkyl group wherein a hydrogen atom is replaced by an aryl group as a substituent. Preferably, the aralkyl group is a group wherein one aryl group is bound to an alkanediyl group. The aryl group or aralkyl group represented by $R^2$ may be substituted on its aromatic ring with one or more substituents selected from halogen, preferably I, and —OH. The aryl and the aryl portion of the aralkyl group are preferably selected from phenyl and naphthyl, such as 2-naphthyl. The alkanediyl portion of the aralkyl group is preferably a C1-C4 alkanediyl group, more preferably a —CH$_2$— group. Thus, $R^2$ is more preferably selected from optionally substituted —CH$_2$-phenyl, and optionally substituted —CH$_2$-naphtyl, in particular optionally substituted —CH$_2$-(2-naphtyl). Optionally substituted —CH$_2$-(2-naphtyl) is a particularly preferred option for $R^2$.

The optionally substituted aryl group and the aryl portion of the optionally substituted aralkyl group, including their preferred embodiments, may be substituted with one or more substituents selected from halogen, preferably I, and —OH. Thus, one or more than one, e.g. 2 or 3, substituent(s) selected from halogen, preferably I, and —OH can be present. However, it is preferred that $R^2$ is non-substituted.

In view of the above, it will be understood that, $R^2$ is most preferably non-substituted —CH$_2$-(naphtyl), and that the naphthyl group is most preferably a 2-naphtyl group to provide $R^2$ as —CH$_2$-(2-naphtyl).

In formula (I), $R^3$ is an optionally substituted aryl group or an optionally substituted aralkyl group, preferably an optionally substituted aralkyl group. The aryl group or aralkyl group may be substituted on its aromatic ring with one or more substituents selected from halogen, preferably I, and —OH. The aryl and the aryl portion of the aralkyl group are preferably selected from phenyl and naphthyl, such as 2-naphtyl. It is more preferred that the aryl and the aryl portion of the aralkyl are phenyl. The alkanediyl portion of the aralkyl group is preferably a C1-C4 alkanediyl group, more preferably a —CH$_2$— group. Thus, $R^3$ is more preferably optionally substituted —CH$_2$-phenyl.

The optionally substituted aryl group and the aryl portion of the optionally substituted aralkyl group, including their preferred embodiments, may be substituted with one or more substituents selected from halogen, preferably I, and —OH. Thus, one or more than one, e.g. 2 or 3, substituent(s) selected from halogen, preferably I, and —OH can be present.

Preferably, $R^3$ is substituted with one substituent which is —OH, or with a combination of one substituent —OH and one substituent —I.

Thus, it is particularly preferred that $R^3$ is —CH$_2$-phenyl substituted on the phenyl ring with one substituent which is —OH, or with a combination of one substituent —OH and one substituent —I, and it is most preferred that the substituent —OH is present in the para-position of the phenyl ring relative to the —CH$_2$— group.

In line with the above, it is preferred in formula (I) that $R^2$ is a group of the formula

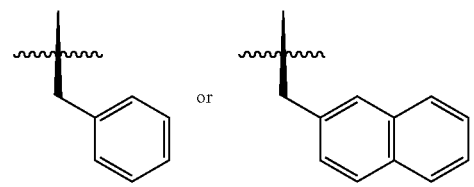

and $R^3$ is a group of the formula

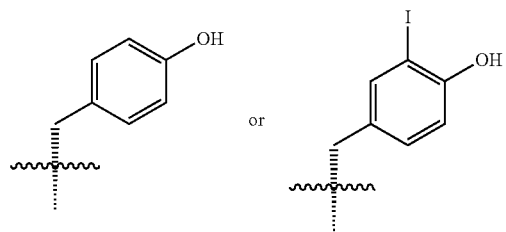

wherein ～ marks the bond which attaches $R^2$ and $R^3$, respectively, to the remainder of the compound of formula (I).

Even more strongly preferred is the combination of $R^2$ and $R^3$ wherein $R^2$ is a group of the formula

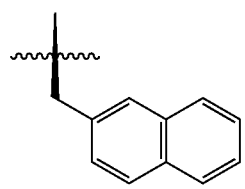

and $R^3$ is a group of the formula

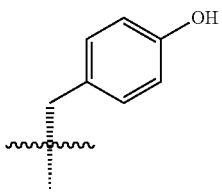

wherein ⁓⁓⁓ marks the bond which attaches $R^2$ and $R^3$, respectively, to the remainder of the compound.

In formula (I), r can be 0 or 1, and it is preferred that r is 1.

Furthermore, as explained above, p is 0 or 1 and q is 0 or 1, and it is preferred that p+q=1. More preferably, p is 0 and q is 1.

$R^4$ in formula (I) is selected from an aryl group and a group EDS. The aryl is preferably selected from phenyl and naphthyl, such as 2-naphthyl. Thus, $R^4$ is more preferably selected from phenyl, naphtyl, such as 2-naphthyl, and a group EDS. It is most preferably a group EDS.

If $R^4$ is a group EDS, it is preferred that the group EDS has a structure selected from (E-1A), (E-2A) and (E-1B).

$X^3$ is selected from an amide bond, an ether bond, a thioether bond, an ester bond, a thioester bond, a urea bridge, an amine bond, and a group of the formula

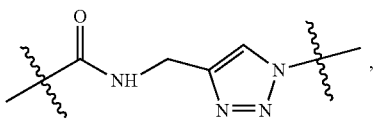 [SMILES: *C(=O)NCc1cn(*)nn1]

wherein the marked bond at the carbonyl group attaches $X^3$ to $R^M$ and the other marked bond attaches $X^3$ to the remainder of the molecule.

Preferably, $X^3$ is selected from an amide bond and a group of the formula

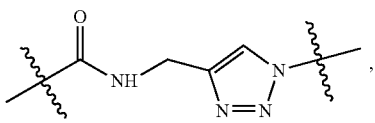 [SMILES: *C(=O)NCc1cn(*)nn1]

wherein the marked bond at the carbonyl group attaches $X^3$ to $R^M$ and the other marked bond attaches $X^3$ to the remainder of the molecule.

In a more preferred embodiment, $X^3$ is an amide bond —C(O)—NH— with the carbon atom attached to $R^M$.

$R^M$ is a marker group which comprises a chelating group optionally containing a chelated non-radioactive or radioactive cation.

As will be understood by the skilled reader, the above definition according to which $R^M$ comprises a chelating group encompasses the case that $R^M$ is a chelating group; in this case the chelating group is typically directly bound to $X^3$;

and the case that $R^M$ comprises, together with the chelating group, e.g. a further linker moiety; in this case the chelating group can be indirectly bound via this further linker moiety to $X^3$.

The chelating group provided by $R^M$ is suitable to form a chelate with a radioactive or non-radioactive cation. Suitable chelating groups for diverse cations are well known in the art, and can be used in the context of the present invention.

The chelating group optionally containing a chelated non-radioactive or radioactive cation is preferably selected from a chelating group comprising at least one of (i) a macrocyclic ring structure with 8 to 20 ring atoms of which 2 or more, preferably 3 or more, are selected from oxygen atoms, sulfur atoms and nitrogen atoms; and (ii) an acyclic, open chain chelating structure with 8 to 20 main chain atoms of which 2 or more, preferably 3 or more are heteroatoms selected from oxygen atoms, sulfur atoms and nitrogen atoms.

An exemplary chelating group, and thus also an exemplary group $R^M$, is a residue of a chelating agent selected from bis(carboxymethyl)-1,4,8,11-tetraazabicyclo[6.6.2] hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicyclo[6.6.2] hexadecan (DO2A) 1,4,7,10-tetraazacyclododecan-N,N',N'', N'''-tetraacetic acid (DOTA), 2-[1,4,7,10-tetraazacyclododecane-4,7,10-triacetic acid]-pentanedioic acid (DOTAGA), N,N'-dipyridoxylethylendiamine-N,N'-diacetate-5,5'-bis (phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N'',N'''-tetraacetic acid (TRITA), triethylenetetraaminehexaacetic acid (TTHA), N,N'-bis[(6-carboxy-2-pyridil)methyl]-4,13-diaza-18-crown-6 ($H_2$macropa) and 4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide] (THP);

which residue is provided by covalently binding a carboxyl group contained in the chelating agent to the remainder of the compound via an ester or an amide bond, preferably an amide bond. It will be understood by the skilled reader that, in formula (I), this ester or amide bond can in this case be encompassed by $X^3$ or can preferably be represented by $X^3$.

Among these chelating agents, DOTA and DOTAGA are preferred.

Thus, it is also preferred that $R^M$—$X^3$— in formula (I) is a group of the formula

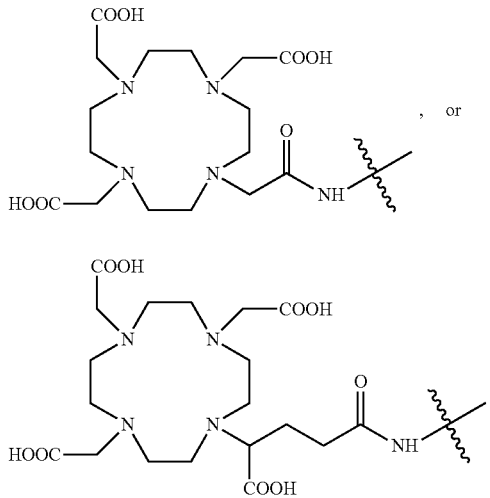

(M-1)

, or (M-2)

wherein the bond marked with ⌇⌇⌇ is attached to the remainder of the compound of formula (I), and wherein the chelating group may contain a chelated non-radioactive or radioactive cation.

Exemplary radioactive cations that are optionally chelated by the chelating group are selected from the cations of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F—[AlF]$^{2+}$.

Preferred chelated cations are selected from the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th, or a cationic molecule comprising $^{18}$F.

In formula (I), the group EDS is contained at least once, such that e.g. one, two or three groups EDS may be contained. Preferably, the compounds or salts in accordance with the invention contain one group or two groups EDS. As explained above, the group(s) EDS may be carried by $L^1$, and/or may be represented by $R^4$.

The most preferred compounds of formula (I) or their salts are those which contain one group EDS which is carried by the linking group $L^1$, including its preferred embodiments as set forth above, and those which contain two groups EDS, one being represented by $R^4$ (i.e. r is 1) and one being carried by $L^1$, including its preferred embodiments as set forth above.

As set out above, the group EDS has a structure selected from (E-1A), (E-1B), (E-2A) and (E-2B):

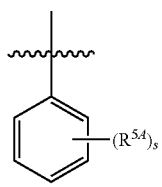

(E-1A)

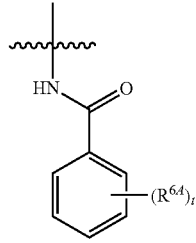

(E-2A)

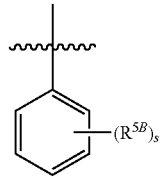

(E-1B)

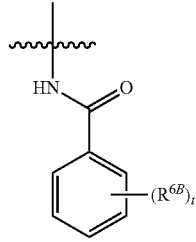

(E-2B)

wherein

⌇⌇⌇ marks the bond which attaches the group EDS, to the remainder of the compound of formula (I);

s is 1, 2 or 3, preferably 1 or 2, and more preferably 1;

t is 1, 2 or 3, preferably 1 or 2, and more preferably 2;

$R^{5A}$ is, independently for each occurrence for s>1, an electron withdrawing substituent, which is preferably selected from —NO$_2$ and —COOH, and which is more preferably —COOH, and wherein the bond between $R^{5A}$ and the phenyl ring indicates that the s groups $R^{5A}$ replace s hydrogen atoms at any position on the phenyl ring;

$R^{5B}$ is, independently for each occurrence for s>1, a substituent carrying an electron lone pair at the atom directly attached to the phenyl ring shown in formula (E-1B), which substituent is preferably selected from —OH and —NH$_2$, and which is more preferably —NH$_2$, and wherein the bond between $R^{5B}$ and the phenyl ring indicates that the s groups $R^{5B}$ replace s hydrogen atoms at any position on the phenyl ring;

$R^{6A}$ is, independently for each occurrence for t>1, an electron withdrawing substituent, which is preferably selected from —NO$_2$ and —COOH, and which is more preferably —COOH, and wherein the bond between $R^{6A}$ and the phenyl ring indicates that the t groups $R^{6A}$ replace t hydrogen atoms at any position on the phenyl ring; and $R^{6B}$ is, independently for each occurrence for t>1, a substituent carrying an electron lone pair at the atom directly attached to the phenyl ring shown in formula (E-1B), which substituent is preferably selected from —OH and —NH$_2$, and which is more preferably —OH, and wherein the bond between $R^{6B}$ and the phenyl ring indicates that the t groups $R^{6B}$ replace t hydrogen atoms at any position on the phenyl ring.

It is generally preferred that, in the group EDS (E-1A), the substituents $R^{5A}$ are the same for s>1 and are selected from —NO$_2$ and —COOH, and are more preferably —COOH, and that, in the group EDS (E-2A), the substituents $R^{6A}$ are the same for t>1 and are selected from —NO$_2$ and —COOH, and are more preferably —COOH.

It is likewise generally preferred that, in the group EDS (E-1B), the substituents $R^{5B}$ are the same for s>1 and are selected from —OH and —NH$_2$, and are more preferably —NH$_2$, and that, in the group EDS (E-2B), the substituents $R^{6B}$ are the same for t>1 and are selected from —OH and —NH$_2$, and are more preferably —OH.

Thus, it is further preferred that the compound of formula (I) contains a group EDS which has the formula (E-2A):

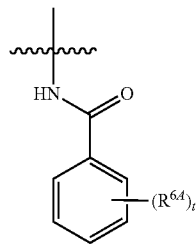

(E-2A)

wherein ⁓ marks the bond which attaches the group EDS to the remainder of the compound of formula (I); and t is 1 or 2, and $R^{6A}$ is —NO$_2$ or —COOH.

Most preferred as group EDS in the context of the present invention is the group

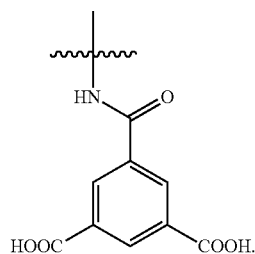

(E-3)

In line with the above, preferred compounds of formula (I) are illustrated by the following formula (Ia)

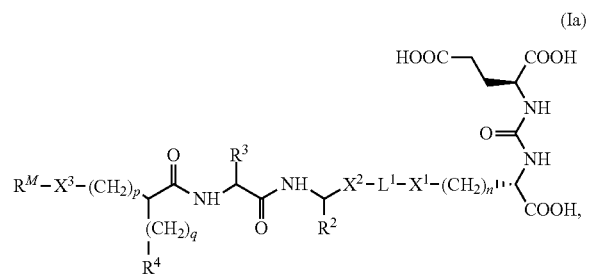

(Ia)

wherein n, $X^1$, $L^1$, $X^2$, $R^2$, $R^3$, $R^4$, q, p, $X^3$ and $R^M$ are defined as above, including their preferred embodiments, and wherein the group EDS is contained at least once and has a structure as defined above, including the preferred embodiments.

More preferred compounds of formula (I) are illustrated by the following formula (Ib)

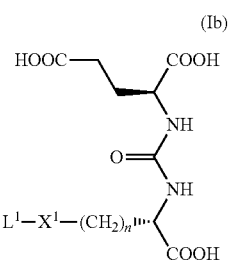

(Ib)

wherein n, $X^1$, $L^1$, $X^2$, $R^2$, $R^3$, $R^4$, $X^3$ and $R^M$ are defined as above, including their preferred embodiments, and wherein the group EDS is contained at least once and has a structure as defined above, including the preferred embodiments.

Still more preferred compounds of formula (I) are illustrated by the following formula (Ic)

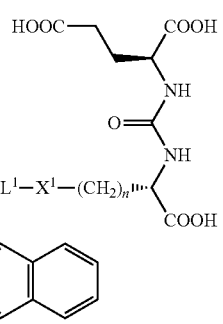

(Ic)

wherein n, $X^1$, $L^1$, $X^2$, $R^4$, $X^3$ and $R^M$ are defined as above, including their preferred embodiments, and wherein the group EDS is contained at least once and has a structure as defined above, including its preferred embodiments.

Still more preferred compounds of formula (I) are illustrated by the following formulae (Id) and (Ie):

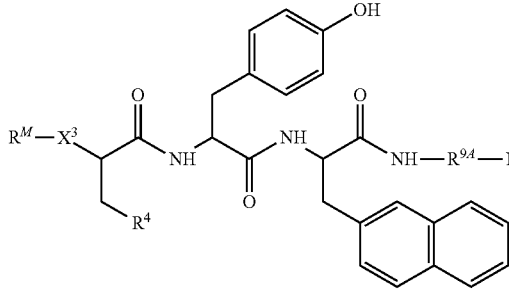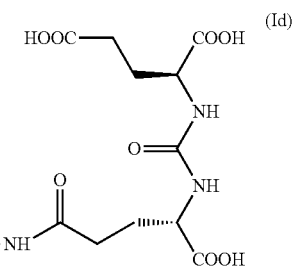

(Id)

wherein $R^{9A}$, $R^{10A}$, $R^{11A}$, $R^4$, $X^3$ and $R^M$ are defined as above, including their preferred embodiments, and wherein either (i) R4 is a group EDS with a structure as defined above, including its preferred embodiments, or (ii) $R^{10A}$ carries one group EDS with a structure as defined above, including its preferred embodiments, or both (i) and (ii) apply;

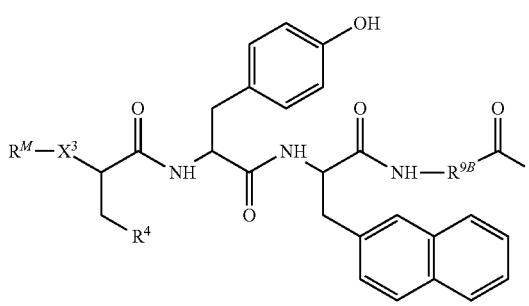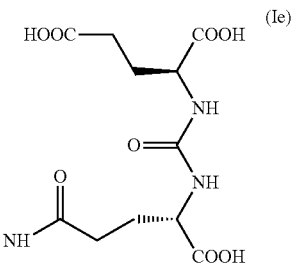

(Ie)

wherein $R^{9B}$, $R^{10B}$, $R^{11B}$, $R^4$, $X^3$ and $R^M$ are defined as above, including their preferred embodiments, and wherein $R^4$ is a group EDS with a structure as defined above, including its preferred embodiments.

Particularly preferred compounds of formula (I) are illustrated by the following formulae (If) and (Ig)

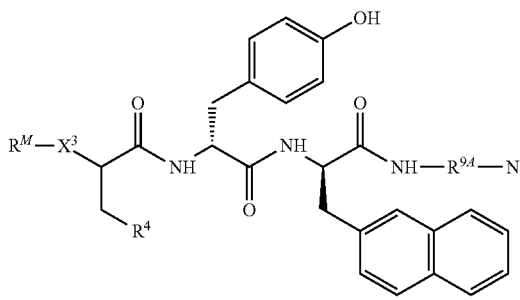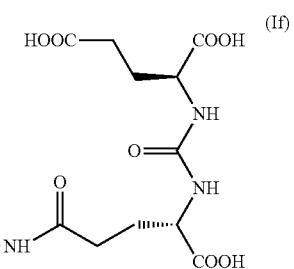

(If)

wherein $R^{9A}$, $R^{10A}$, $R^{11A}$, $R^4$, $X^3$ and $R^M$ are defined as above, including their preferred embodiments, and wherein either (i) $R^4$ is a group EDS with a structure as defined above, including its preferred embodiments, or (ii) $R^{10A}$ carries one group EDS with a structure as defined above, including its preferred embodiments, or both (i) and (ii) apply;

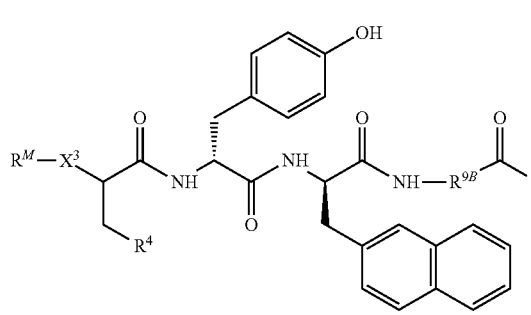
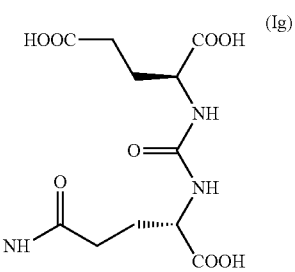

wherein $R^{9B}$, $R^{10B}$, $R^{11B}$, $R^4$, $X^3$ and $R^M$ are defined as above, including their preferred embodiments, and wherein $R^4$ is a group EDS with a structure as defined above, including its preferred embodiments.

In a preferred embodiment, said chelating group has a radionuclide bound which radionuclide emits α-radioation. Radionuclides emitting α-radiation include $^{212}$Bi, $^{213}$Bi, and $^{225}$Ac.

As noted above, the introduction of the electron deficient substituents drastically increased the internalization capacities. This feature results in higher tumor uptake and especially longer retention in the tumor tissue as demonstrated by the in vitro experiments (see examples). Since the complex of the chelator and alpha-particle emitting radionuclide is prone to decomplexation via physical recoil effect, the feature of elongated intracellular retention will reduce the probability of freely circulating radionuclides in vivo and thus increase safety and reduce unwanted radiation.

Particularly preferred compounds of the invention are the following:

DOTAGA-y(3-I)fk(L-Asu[KuE]-2,4-DNBA)
(PSMA-36)

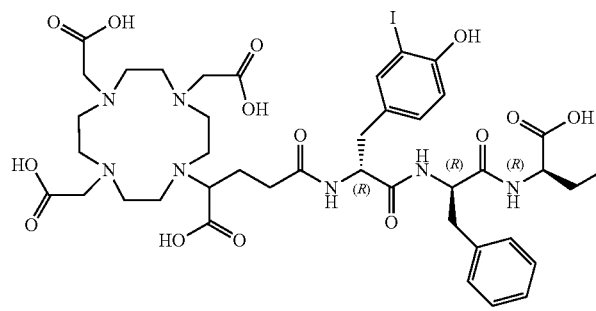
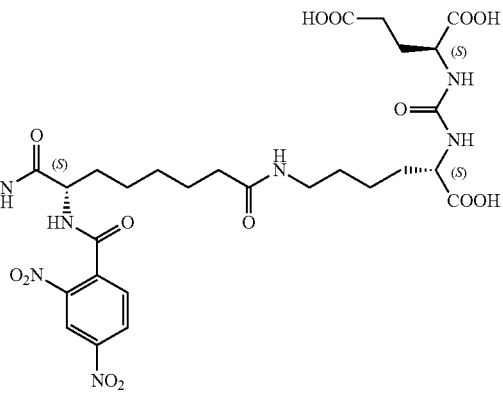

DOTAGA-F(4-NH₂)y-2-nal-k(Suc-N⁵-orn-C⁴-EuE)
(PSMA-49)
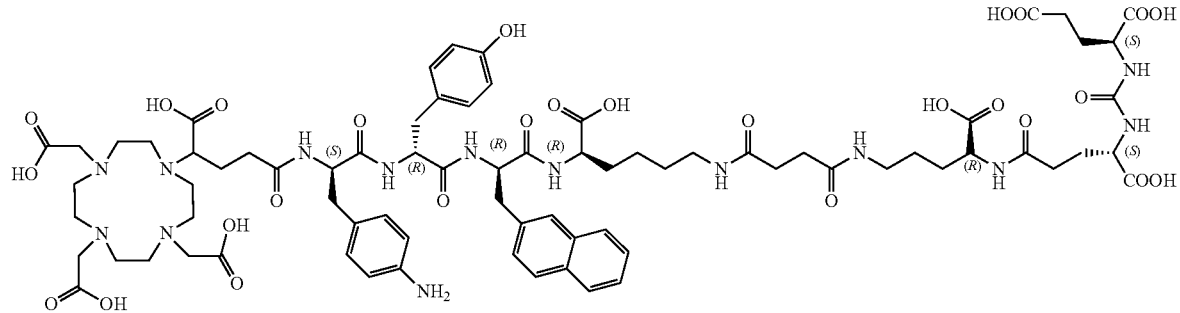
DOTAGA-F(4-NO₂)-y-2-nal-k(Suc-N⁵-orn-C⁴-EuE)
(PSMA-52)
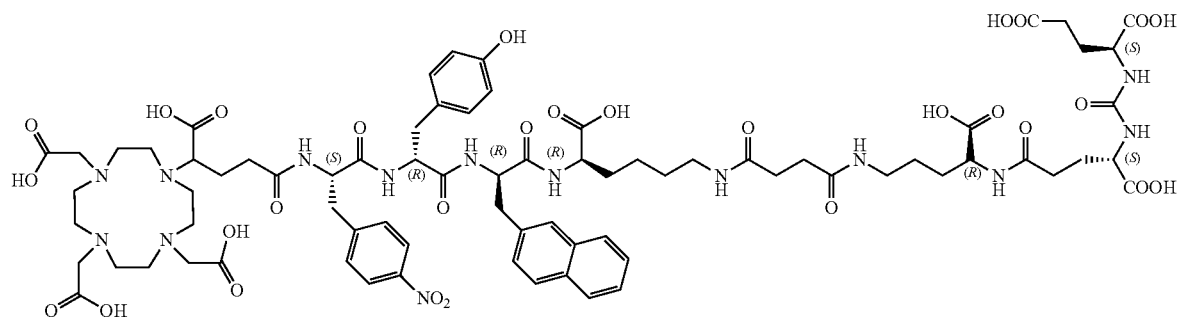
2,4-DNBA-Dap(DOTAGA)-y-2-nal-k(Suc-N⁵-orn-
C⁴-EuE) (PSMA-53)
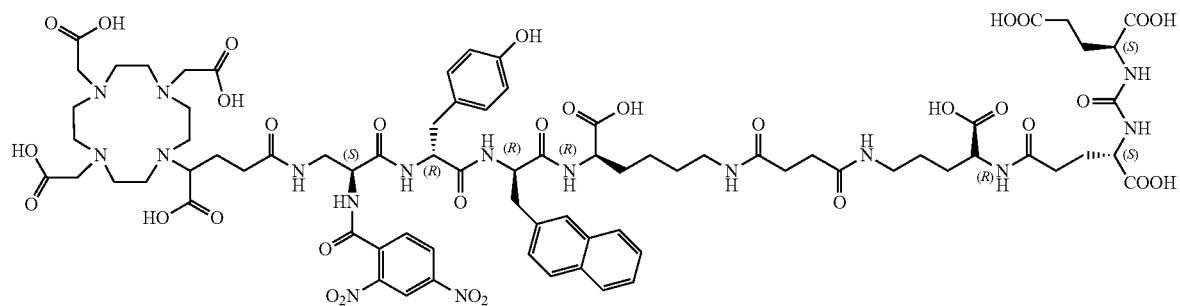

DOTAGA-F(4-NH$_2$)y-2-nal-e(Abz-N$^5$-orn-C$^4$-EuE) (PSMA-60)
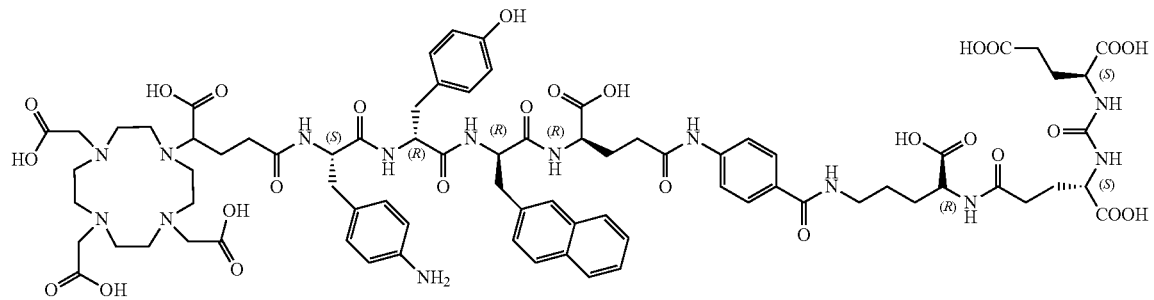
DOTAGA-F(4-NH$_2$)y-2-nal-k(d[N$^5$-orn-C$^4$-EuE]-2,4-DNBA) (PSMA-61)
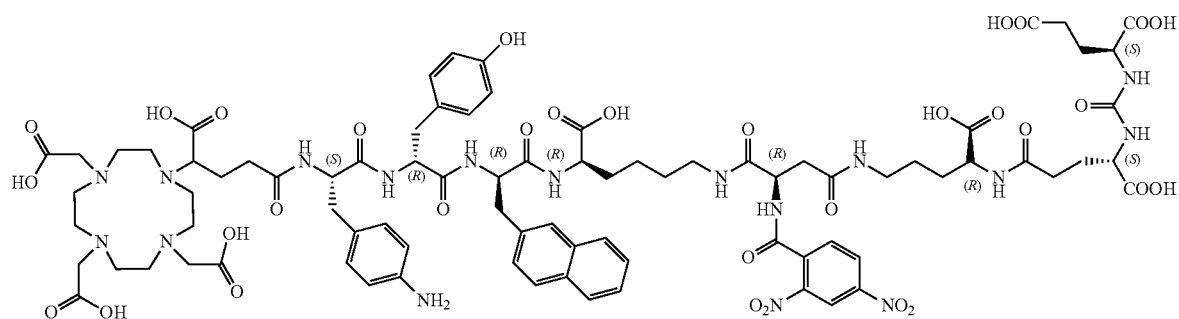
DOTAGA-F(4-NH$_2$)y-2-nal-k(d[N$^5$-orn-C$^4$-EuE]-TMA) (PSMA-62)
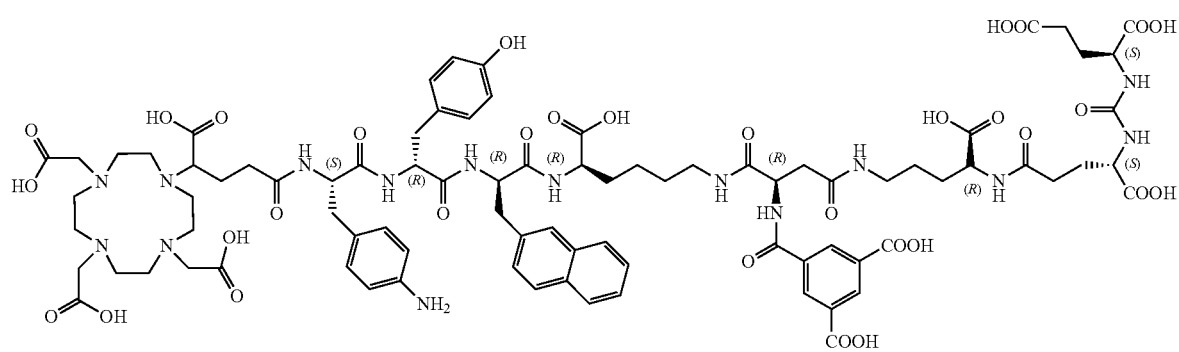

2,4-DNBA-Dap(DOTAGA)y-2-nal-e(Abz-N⁵-orn-C⁴-EuE) (PSMA-65)
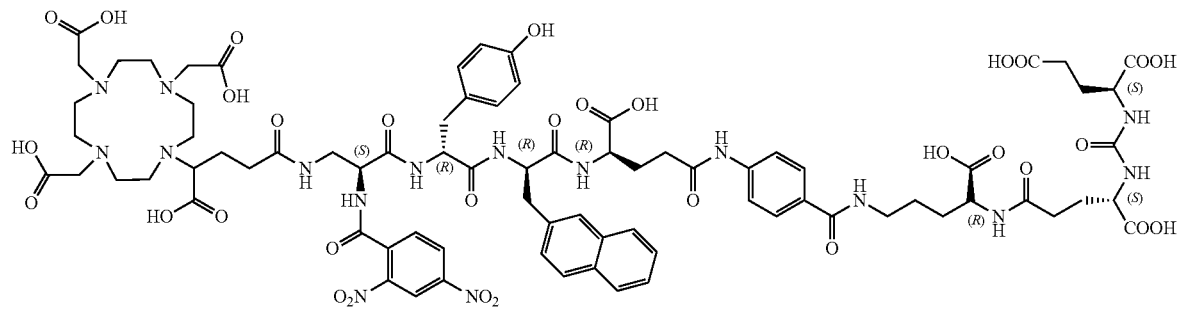
DOTAGA-Dap(TMA)y-2-nal-k(d[N⁵-orn-C⁴-EuE]-TMA) (PSMA-66)
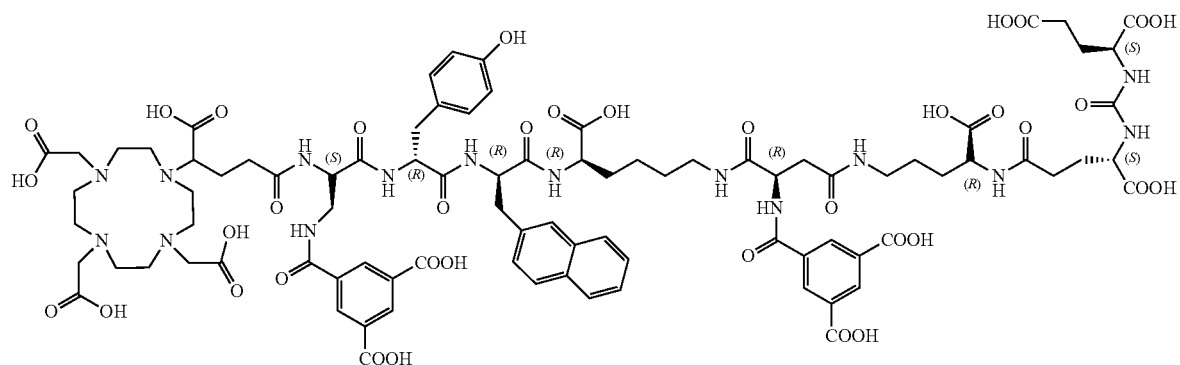
DOTAGA-2-Nal-y-2-nal-k(d[N⁵-orn-C⁴-EuE]-TMA) (PSMA-71)
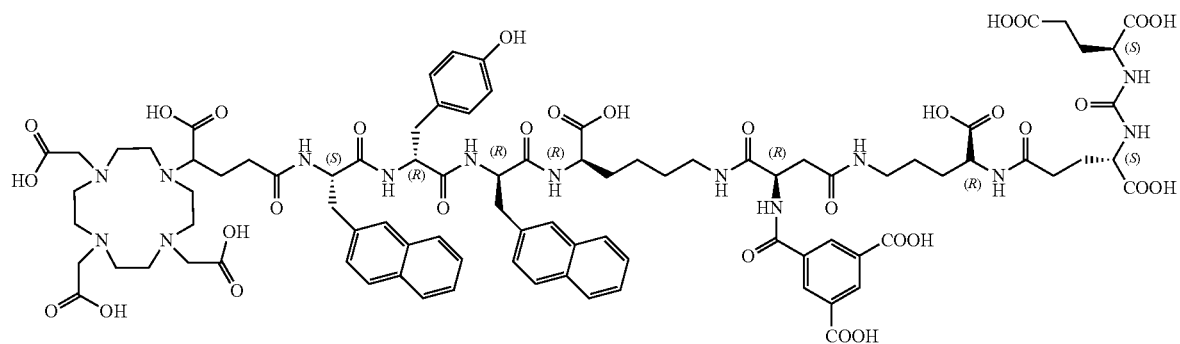

DOTAGA-F(4-NH$_2$)y-2-nal-k(d[N$^5$-orn-C$^4$-EuE]-3,5-DHBA) (PSMA-78)

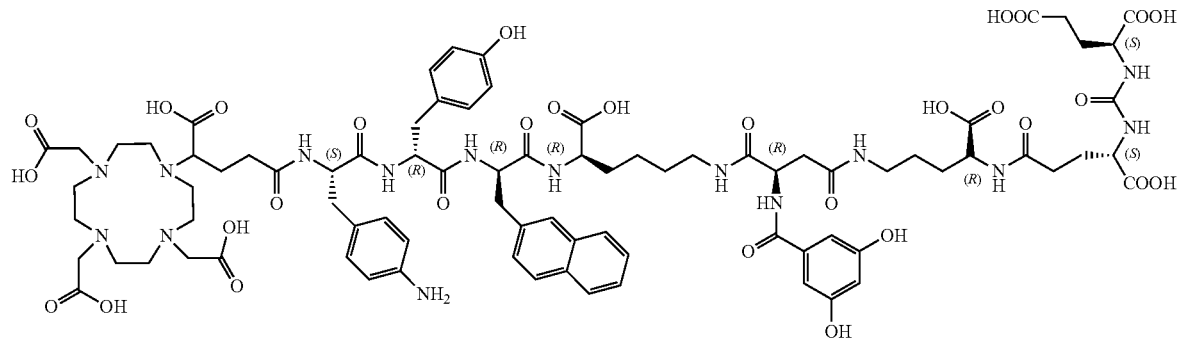

The advantageous properties of these inventive compounds can be seen from the data in Tables 1 and 2 below, which data is presented graphically in FIG. 1.

TABLE 1

Summary of all in vitro investigated parameter for the EuK-based PSMA inhibitors. E designates Glu, u urea and K designates Lys. Lower case single letters (such as "y") designate D-forms of the respective amino acid. The half maximal inhibitory concentration (IC$_{50}$) of the PSMA inhibitors was determined in a competitive binding assay using LNCaP cell (1.5 * 10$^5$ cells/well, 1 h, 4° C., HBSS + 1% BSA) and ([$^{125}$I]I-BA)KuE as radioligand. Internalized activity expressed in [%] as relative cellular uptake to ([$^{125}$I]I-BA)KuE (1.25 * 10$^5$ cells/well, PLL-coated plates, c = 0.2 nM for ([$^{125}$I]I-BA)KuE and c = 1.0 nM for $^{177}$Lu-labeled PSMA inhibitors. DMEM/F-12 + 5% BSA, 37° C., 60 min). Data are corrected for non-specific binding (10 μM 2-PMPA). IC$_{50}$ and internalization data are expressed as mean ± SD (n = 3). Lipophilicity expressed as logP (distribution coefficient in n-octanol/PBS) of radiolabeled PSMA inhibitors. Data for logP expressed as mean ± SD (n = 6). Albumin binding (HSA) expressed in [%] after logarithmic plotting and calibration (n = 1). Configuration describes simplified the N- to C-terminal structural composition of the peptide spacer and linker without the chelator.

| PSMA inhibitor | Configuration | IC$_{50}$ [nM] | Internalization [%] | logP | HSA [%] |
|---|---|---|---|---|---|
| [$^{nat/177}$Lu]PSMA I&T | -y(3-I)fk- | 7.9 ± 2.4 | 75.5 ± 1.6 | −4.12 ± 0.11 | 78.6 |
| [$^{nat/177}$Lu]PSMA-617 | | 3.8 ± 1.7 | 160.1 ± 1.5 | n.d. | 74.7 |
| [$^{nat/177}$Lu]PSMA-36 | -y(3-I)fk- ‖ -2,4-DNBA- | 5.3 ± 1.0 | 189.8 ± 37.5 | n.d. | 82.5 | n.d. = not determined.
"-II-" indicates a simplified conjugation.

TABLE 2

Summary of all in vitro investigated parameter for the EuE-based PSMA inhibitors. The half maximal inhibitory concentration (IC$_{50}$) of the PSMA inhibitors was determined in a competitive binding assay using LNCaP cell (1.5 * 10$^5$ cells/well, 1 h, 4° C., HBSS + 1% BSA) and ([$^{125}$I]I-BA)KuE as radioligand. Internalized activity expressed in [%] as relative cellular uptake to ([$^{125}$I]I-BA)KuE (1.25 * 10$^5$ cells/well, c = 0.2 nM for ([$^{125}$I]I- BA)KuE and c = 1.0 nM for $^{177}$Lu-labeled PSMA inhibitors. DMEM/F-12 + 5% BSA, 37° C., 60 min). Data are corrected for non-specific binding (10 μM 2-PMPA). IC$_{50}$ and internalization data are expressed as mean ± SD (n = 3). Lipophilicity expressed as logP (distribution coefficient in n-octanol/PBS) of radiolabeled PSMA inhibitors. Data for logP expressed as mean ± SD (n = 6). Albumin binding (HSA) expressed in [%] after logarithmic plotting and calibration (n = 1). Configuration describes simplified the N- to C-terminal structural composition of the peptide spacer and linker without the chelator.

| PSMA inhibitor | Configuration | IC$_{50}$ [nM] | Internalization [%] | logP | HSA [%] |
|---|---|---|---|---|---|
| [$^{nat/177}$Lu]PSMA I&T | -y(3-I)fk- ‖ -KuE | 7.9 ± 2.4 | 75.5 ± 1.6 | −4.12 ± 0.11 | 78.6 |
| [$^{nat/177}$Lu]PSMA-46 | -y-2-nal-k- ‖ -EuE | 3.2 ± 1.1 | 216.2 ± 9.2 | −4.21 ± 0.08 | 57.7 |
| [$^{nat/177}$Lu]PSMA-617 | | 3.8 ± 1.7 | 160.1 ± 1.5 | n.d. | 74.7 |
| [$^{nat/177}$Lu]PSMA-52 | -F(4-NO$_2$)-y-2-nal-k(Suc-N$^5$-orn-C$^4$-EuE) | 3.4 ± 0.2 | 229.9 ± 8.0 | −4.11 ± 0.07 | 95.4 |
| [$^{nat/177}$Lu]PSMA-53 | 2,4-DNBA-Dap(DOTAGA)-y-2- | 3.2 ± 0.5 | 293.6 ± 10.0 | −4.08 ± 0.04 | 95.9 |

TABLE 2-continued

Summary of all in vitro investigated parameter for the EuE-based PSMA inhibitors. The half maximal inhibitory concentration ($IC_{50}$) of the PSMA inhibitors was determined in a competitive binding assay using LNCaP cell ($1.5 * 10^5$ cells/well, 1 h, 4° C., HBSS + 1% BSA) and ($[^{125}I]I$-BA)KuE as radioligand. Internalized activity expressed in [%] as relative cellular uptake to ($[^{125}I]I$-BA)KuE ($1.25 * 10^5$ cells/well, PLL-coated plates, c = 0.2 nM for ($[^{125}I]I$- BA)KuE and c = 1.0 nM for $^{177}$Lu-labeled PSMA inhibitors. DMEM/F-12 + 5% BSA, 37° C., 60 min). Data are corrected for non-specific binding (10 μM 2-PMPA). $IC_{50}$ and internalization data are expressed as mean ± SD (n = 3). Lipophilicity expressed as logP (distribution coefficient in n-octanol/PBS) of radiolabeled PSMA inhibitors. Data for logP expressed as mean ± SD (n = 6). Albumin binding (HSA) expressed in [%] after logarithmic plotting and calibration (n = 1). Configuration describes simplified the N- to C-terminal structural composition of the peptide spacer and linker without the chelator.

| PSMA inhibitor | Configuration | $IC_{50}$ [nM] | Internalization [%] | logP | HSA [%] |
|---|---|---|---|---|---|
| $[^{nat/177}Lu]$PSMA-61 | nal-k(Suc-$N^5$-orn-$C^4$-EuE)-F(4-$NH_2$)y-2-nal-k(d[$N^5$-orn-$C^4$-EuE]-2,4-DNBA) | 4.5 ± 0.4 | 359.5 ± 22.6 | −4.07 ± 0.05 | 63.3 |
| $[^{nat/177}Lu]$PSMA-62 | -F(4-$NH_2$)y-2-nal-k(d[$N^5$-orn-$C^4$-EuE]-TMA) | 4.0 ± 0.2 | 343.9 ± 6.0 | −4.12 ± 0.05 | >91.0 |
| $[^{nat/177}Lu]$PSMA-66 | -Dap(TMA)y-2-nal-k(d[$N^5$-orn-$C^4$-EuE]-TMA) | 3.8 ± 0.3 | 297.8 ± 2.0 | −4.25 ± 0.14 | 64.4 |
| $[^{nat/177}Lu]$PSMA-71 | -2-Nal-y-2-nal-k(d[$N^5$-orn-$C^4$-EuE]-TMA) | 5.3 ± 2.0 | 206.8 ± 1.7 | −4.13 ± 0.09 | 98.2 |
| $[^{nat/177}Lu]$PSMA-49 | -F(4-$NH_2$)y-2-nal-k(Suc-$N^5$-orn-$C^4$-EuE) | 2.5 ± 0.6 | 245.0 ± 4.2 | −4.01 ± 0.11. | 74.2. |
| $[^{nat/177}Lu]$PSMA-60 | -F(4-$NH_2$)y-2-nal-e(Abz-$N^5$-orn-$C^4$-EuE) | 6.6 ± 1.5 | 267.4 ± 7.9 | −3.85 ± 0.13 n.d. | 98.5 n.d. |
| $[^{nat/177}Lu]$PSMA-78 | -F(4-$NH_2$)y-2-nal-k(d[$N^5$-orn-$C^4$-EuE]-3,5-DHBA) | 3.9 ± 0.6. | 289.0 ± 6.2 | n.d. | n.d. |
| $[^{nat/177}Lu]$PSMA-65 | 2,4-DNBA-Dap(DOTAGA)y-2-nal-e(Abz-$N^5$-orn-$C^4$-EuE) | 3.5 ± 0.3 n.d. | 340.2 ± 19.9 | −4.15 ± 0.08 n.d. | 98.7 n.d. | n.d. = not determined.
"-II-" indicates a simplified conjugation.

Preferred labeling schemes for these most preferred compounds are as defined herein above.

In a further aspect, the present invention provides a pharmaceutical composition comprising or consisting of one or more compounds or salts of the invention as disclosed herein above.

In a further aspect, the present invention provides a diagnostic composition comprising or consisting of one or more compounds or salts of the invention as disclosed herein above.

In a further aspect, the present invention provides a therapeutic composition comprising or consisting of one or more compounds or salts of the invention as disclosed herein above.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection and/or delivery, e.g., to a site in the pancreas or into a brain artery or directly into brain tissue. The compositions may also be administered directly to the target site, e.g., by biolistic delivery to an external or internal target site, like the pancreas or brain. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Pharmaceutically active matter may be present in amounts between 0.1 ng and 10 mg/kg body weight per dose; however, doses below or above this exemplary range are envisioned, especially considering the aforementioned factors.

To the extent the above disclosed pharmaceutical composition, diagnostic composition and therapeutic composition comprises one or more compounds of the invention, it is preferred that no further pharmaceutically active compounds, diagnostically active compounds or therapeutically active compounds are present. In the alternative, further therapeutically active, diagnostically active or pharmaceutically active compounds may be present, for example, anticancer agents.

Combination of a therapeutic treatment with the compounds of the present invention might have a synergistic or cumulative treatment effect, similar to the treatment of neuroendocrine tumors with [$^{177}$Lu]DOTATATE radiotherapy in combination with chemotherapy or immunotherapies. A first phase 3 study comparing the combination of $^{177}$Lu PRRT and capecitabine (Xeloda; Genentech), an oral chemotherapy agent, with [$^{177}$Lu]DOTATATE alone has been started at Erasmus M C, Rotterdam in 2017 (van Essen M, Krenning E P, Kam B L, de Herder W W, van Aken M O, Kwekkeboom D J. Report on short-term side effects of treatments with 177Lu-octreotate in combination with capecitabine in seven patients with gastroenteropancreatic neuroendocrine tumours. Eur J Nucl Med Mol Imaging. 2008; 35:743-748).

Further studies on combination therapies, named peptide receptor chemoradionuclide therapy (PRCRT), have recently been published (Kong G, Callahan J, Hofman M S, et al. High clinical and morphologic response using 90Y-DOTA-octreotate sequenced with 177Lu-DOTA-octreotate induction peptide receptor chemoradionuclide therapy (PR-CRT) for bulky neuroendocrine tumours. Eur J Nucl Med Mol Imaging. 2017; 44:476-489). Similar "combined treatment approaches" will be carried out in the near future to improve the efficiency of PSMA-targeted radioligand therapies.

In a further aspect, the present invention provides one or more compounds or salts of the invention as disclosed herein above for use in medicine.

Preferred uses in medicine are in nuclear medicine such as nuclear diagnostic imaging, also named nuclear molecular imaging, and/or targeted radiotherapy of diseases associated with an overexpression, preferably of PSMA on the diseased tissue.

In a further aspect, the present invention provides a compound or salt of the invention as defined herein above for use in a method of diagnosing and/or staging cancer, preferably prostate cancer.

Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In terms of medical indications to be subjected to therapy, especially radiotherapy, cancer is a preferred indication. Prostate cancer is a particularly preferred indication.

In a further aspect, the present invention provides a compound or salt of the invention as defined herein above for use in a method of diagnosing and/or staging cancer, preferably prostate cancer.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

In particular, the invention provides the subject matter summarized in the following items.

1. A compound of formula (I), or a pharmaceutically acceptable salt thereof,

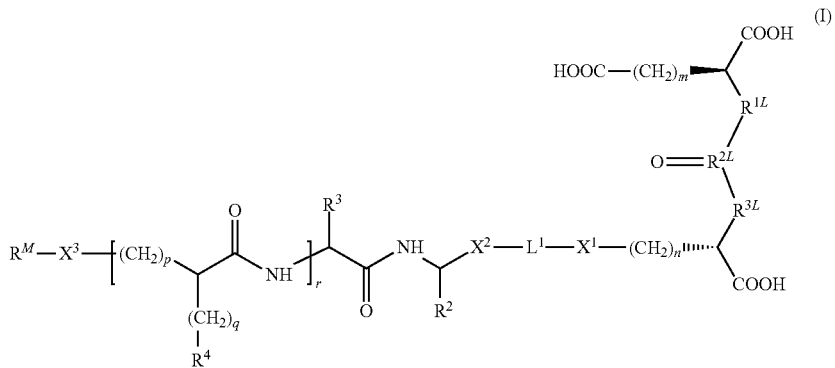

wherein
m is an integer of 2 to 6, preferably 2 to 4, more preferably 2;
n is an integer of 2 to 6, preferably 2 to 4, more preferably 2 or 4;
$R^{1L}$ is $CH_2$, NH or O, preferably NH;
$R^{2L}$ is C or P(OH), preferably C;
$R^{3L}$ is $CH_2$, NH or O, preferably NH;
$X^1$ is selected from an amide bond, an ether bond, a thioether bond, an ester bond, a thioester bond, a urea bridge, and an amine bond, and is preferably an amide bond;
$L^1$ is a divalent linking group with a structure selected from an oligoamide, an oligoether, an oligothioether, an oligoester, an oligothioester, an oligourea, an oligo (ether-amide), an oligo(thioether-amide), an oligo(ester-amide), an oligo(thioester-amide), oligo(urea-amide), an oligo(ether-thioether), an oligo(ether-ester), an oligo(ether-thioester), an oligo(ether-urea), an oligo(thioether-ester), an oligo(thioether-thioester), an oligo(thioether-urea), an oligo(ester-thioester), an oligo(ester-urea), and an oligo(thioester-urea), preferably with a structure selected from an oligoamide and an oligo(ester-amide), which linking group may carry a group EDS;

$X^2$ is selected from an amide bond, an ether bond, a thioether bond, an ester bond, a thioester bond, a urea bridge, and an amine bond, and is preferably an amide bond;

$R^2$ is an optionally substituted aryl group or an optionally substituted aralkyl group, which aryl group or aralkyl group may be substituted on its aromatic ring with one or more substituents selected from halogen, preferably I, and —OH;

$R^3$ is an optionally substituted aryl group or an optionally substituted aralkyl group, which aryl group or aralkyl group may be substituted on its aromatic ring with one or more substituents selected from halogen, preferably I, and —OH;

r is 0 or 1, preferably 1;

p is 0 or 1;

q is 0 or 1;

and preferably p+q=1;

$R^4$ is selected from an optionally substituted aryl group and a group EDS, which aryl group may be substituted on its aromatic ring with one or more substituents selected from halogen, preferably I, —OH and —NH$_2$;

$X^3$ is selected from an amide bond, an ether bond, a thioether bond, an ester bond, a thioester bond, a urea bridge, an amine bond, and a group of the formula

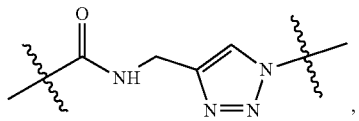 [SMILES: *C(=O)NCc1cn(*)nn1]

, wherein the marked bond at the carbonyl group attaches $X^3$ to $R^M$ and the other marked bond attaches $X^3$ to the remainder of the compound of formula (I); and is preferably an amide bond;

$R^M$ is a marker group which comprises a chelating group optionally containing a chelated non-radioactive or radioactive cation;

and wherein the group EDS is contained at least once in the compound of formula (I) and has a structure selected from (E-1A), (E-1B), (E-2A) and (E-2B):

(E-1A)

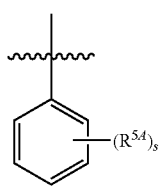

-continued (E-2A)

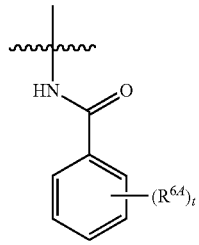

(E-1B)

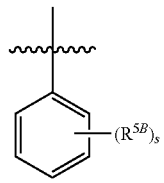

(E-2B)

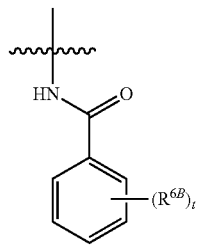

wherein

⁓⁓⁓ marks the bond which attaches the group EDS, to the remainder of the compound of formula (I);

s is 1, 2 or 3, preferably 1 or 2, and more preferably 1;

t is 1, 2 or 3, preferably 1 or 2, and more preferably 2;

$R^{5A}$ is, independently for each occurrence for s>1, an electron withdrawing substituent, which is preferably selected from —NO$_2$ and —COOH, and which is more preferably —COOH, and wherein the bond between $R^{5A}$ and the phenyl ring indicates that the s groups $R^{5A}$ replace s hydrogen atoms at any position on the phenyl ring;

$R^{5B}$ is, independently for each occurrence for s>1, a substituent carrying an electron lone pair at the atom directly attached to the phenyl ring shown in formula (E-1B), which substituent is preferably selected from —OH and —NH$_2$, and which is more preferably —NH$_2$, and wherein the bond between $R^{5B}$ and the phenyl ring indicates that the s groups $R^{5B}$ replace s hydrogen atoms at any position on the phenyl ring;

$R^{6A}$ is, independently for each occurrence for t>1, an electron withdrawing substituent, which is preferably selected from —NO$_2$ and —COOH, and which is more preferably —COOH, and wherein the bond between $R^{6A}$ and the phenyl ring indicates that the t groups $R^{6A}$ replace t hydrogen atoms at any position on the phenyl ring; and $R^{6B}$ is, independently for each occurrence for t>1, a substituent carrying an electron lone pair at the atom directly attached to the phenyl ring shown in formula (E-1B), which substituent is preferably selected from —OH and —NH$_2$, and which is more preferably —OH, and wherein the bond between $R^{6B}$ and the phenyl ring indicates that the t groups $R^{6B}$ replace t hydrogen atoms at any position on the phenyl ring.

2. The compound or salt of item 1, wherein m is 2, n is 2 or 4, $R^{1L}$ is NH, $R^{2L}$ is C, and $R^{3L}$ is NH.

3. The compound or salt of item 1 or 2, wherein n is 2.

4. The compound or salt of any of items 1 to 3, wherein $X^1$ is an amide bond.

5. The compound or salt of item 4, wherein n is 2 and $X^1$ is an amide bond with the carbon atom of the amide bond —C(O)—NH— being attached to the group —(CH$_2$)$_n$—.

6. The compound or salt of any of items 1 to 5, wherein $L^1$ is a divalent linking group with a structure selected from an oligoamide which comprises a total of 1 to 5, more preferably a total of 1 to 3, and most preferably a total of 1 or 2 amide bonds within its backbone, and an oligo (ester-amide) which comprises a total of 2 to 5, more preferably a total of 2 to 3, and most preferably a total of 2 amide and ester bonds within its backbone, which linking group may carry a group EDS.

7. The compound or salt of item 6, wherein $L^1$ represents a divalent linking group with an oligoamide structure which comprises 1 or 2 amide bonds within its backbone, which linking group may carry a group EDS.

8. The compound or salt of any of items 1 to 7, wherein the linking group $L^1$ carries one group EDS.

9. The compound or salt of any of items 1 to 8, wherein $X^2$ is an amide bond.

10. The compound or salt of item 9, wherein $X^2$ is an amide bond with the nitrogen atom of the amide bond —C(O)—NH— being attached to $L^1$.

11. The compound or salt of any of items 1 to 10, wherein the moiety —$X^2$-$L^1$-$X^1$— in formula (I) has a structure selected from:

$$*-C(O)-NH-R^7-NH-C(O)-R^8-C(O)-NH— \quad (L-1),$$

$$*-C(O)-NH-R^{9A}-NH-C(O)-R^{10A}-C(O)-NH-R^{11A}-NH-C(O)— \quad (L-2A), \text{ and}$$

$$*-C(O)-NH-R^{9B}-C(O)-NH-R^{10B}-C(O)-NH-R^{11B}-NH-C(O)— \quad (L-2B);$$

wherein the amide bond marked with * is attached to the carbon atom carrying $R^2$ in formula (I), and wherein $R^7$, $R^8$, $R^{9A}$, $R^{9B}$, $R^{11A}$ and $R^{11B}$ are independently selected from optionally substituted C2 to C10 alkanediyl, preferably optionally substituted linear C2 to C10 alkanediyl, which alkanediyl groups may each be substituted by one or more substituents independently selected from —OH, —OCH$_3$, —COOH, —COOCH$_3$, —NH$_2$, —NHC(NH)NH$_2$, and a group EDS, and $R^{10A}$ and $R^{10B}$ are selected from optionally substituted C2 to C10 alkanediyl, preferably optionally substituted linear C2 to C10 alkanediyl, and optionally substituted C6 to C10 arenediyl, preferably phenylene, which alkanediyl and arenediyl group may each be substituted by one or more substitutents independently selected from —OH, —OCH$_3$, —COOH, —COOCH$_3$, —NH$_2$, —NHC(NH)NH$_2$, and a group EDS. $R^{10A}$ is preferably optionally substituted C2 to C10 alkanediyl, more preferably optionally substituted linear C2 to C10 alkanediyl as defined above. $R^{10B}$ is preferably optionally substituted C6 to C10 arenediyl as defined above, more preferably a phenylene group, e.g. para-phenylene group.

12. The compound or salt of item 11, wherein the total number of carbon atoms in $R^7$ and $R^8$ of formula (L-1) is 6 to 20, more preferably 6 to 16, without carbon atoms contained in optional substituents, that the total number of carbon atoms in $R^{9A}$, $R^{10A}$ and $R^{11A}$ of formula (L-2A) is 6 to 20, more preferably 6 to 16, without carbon atoms contained in optional substituents, and that the total number of carbon atoms in $R^{9B}$$R^{10B}$ and $R^{11B}$ of formula (L-2B) is 6 to 20, more preferably 6 to 16, without carbon atoms contained in optional substituents.

13. The compound or salt of item 11 or 12, wherein
the moiety —$X^2$-$L^1$-$X^1$— has a structure (L-1) and $R^8$ carries a group EDS as at least one substituent, or
the moiety —$X^2$-$L^1$-$X^1$— has a structure (L-2A) and $R^{10A}$ carries a group EDS as at least one substituent.

14. The compound or salt of item 7, wherein the moiety —$X^2$-$L^1$-$X^1$— has a structure selected from:

$$*-C(O)-NH-CH(COOH)-R^{12}-NH-C(O)-R^{13}-C(O)-NH— \quad (L-3),$$

$$*-C(O)-NH-CH(COOH)-R^{14}-NH-C(O)-R^{15}-C(O)-NH-R^{16}-CH(COOH)-NH-C(O)— \quad (L-4), \text{ and}$$

$$*-C(O)-NH-CH(COOH)-R^{17}-C(O)-NH-R^{18}-C(O)-NH-R^{19}-CH(COOH)-NH-C(O)— \quad (L-5);$$

wherein the bond marked with * is attached to the carbon atom carrying $R^2$ in formula (I),
$R^{12}$ and $R^{14}$ are independently selected from linear C2 to C6 alkanediyl, preferably from linear C3 to C6 alkanediyl,
$R^{13}$ is a linear C2 to C10 alkanediyl, preferably a linear C4 to C8 alkanediyl,
$R^{15}$ and $R^{16}$ are independently selected from linear C2 to C6 alkanediyl, preferably from linear C2 to C4 alkanediyl,
and wherein each of $R^{13}$ and $R^{15}$ may carry one group EDS as a substituent, and more preferably each of $R^{13}$ and $R^{15}$ carries one group EDS as a substituent,
$R^{17}$ is a linear C2 to C6 alkanediyl, preferably a linear C2 to C4 alkanediyl,
$R^{18}$ is a phenylene group, e.g. a para-phenylene group, and
$R^{19}$ is a linear C2 to C6 alkanediyl, preferably a linear C2 to C4 alkanediyl.

15. The compound or salt of item 14, wherein the total number of carbon atoms in $R^{12}$ and $R^{13}$ in formula (L-3), without carbon atoms contained in the group EDS as substituent, is 6 to 16, more preferably 6 to 14, and the total number of carbon atoms in $R^{14}$, $R^{15}$ and $R^{16}$ in formula (L-4), without carbon atoms contained in the group EDS as substituent, is 6 to 16, more preferably 6 to 14.

16. The compound or salt of any of items 1 to 15, wherein $R^2$ is an optionally substituted aralkyl group selected from optionally substituted —CH$_2$-phenyl and optionally substituted —CH$_2$-naphtyl, more preferably optionally substituted —CH$_2$-(2-naphtyl), wherein the phenyl and the naphtyl group are optionally substituted with a substituent selected from halogen, preferably I, and —OH.

17. The compound or salt of item 16, wherein $R^2$ is an aralkyl group of the formula —CH$_2$-naphthyl, more preferably —CH$_2$-(2-naphtyl).

18. The compound or salt of any of items 1 to 17, wherein $R^3$ is an optionally substituted aralkyl group selected from optionally substituted —CH$_2$-phenyl and optionally substituted —CH$_2$-naphtyl, more preferably optionally substituted —CH$_2$-phenyl, wherein the phenyl and the naphtyl group are optionally substituted with a substituent selected from halogen, preferably I, and —OH.

19. The compound or salt of item 18, wherein $R^3$ is an aralkyl group of the formula —CH$_2$-phenyl, wherein the phenyl ring is substituted with with one substituent which is —OH, or with a combination of one substituent —OH and one substituent —I.

20. The compound or salt of any of items 1 to 15, wherein R² is a group of the formula

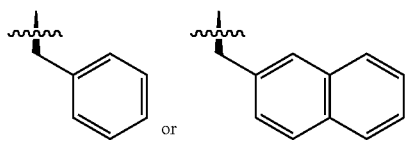

and R³ is a group of the formula

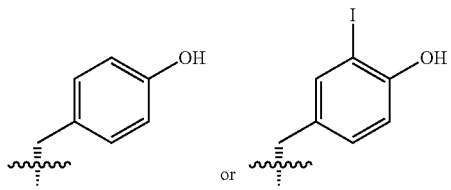

wherein ⌇⌇⌇ marks the bond which attaches R² and R³, respectively, to the remainder of the compound of formula (I).

21. The compound or salt of item 20, wherein R² is a group of the formula

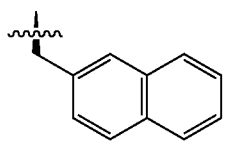

and R³ is a group of the formula

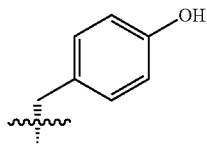

wherein ⌇⌇⌇ marks the bond which attaches R² and R³, respectively, to the remainder of the molecule.

22. The compound or salt of any of items 1 to 21, wherein r is 1.

23. The compound or salt of any of items 1 to 22, wherein p is 0 and q is 1.

24. The compound or salt of any of items 1 to 23, wherein R⁴ is selected from phenyl, optionally naphtyl, and a group EDS.

25. The compound or salt of any of item 24, wherein R⁴ is selected from naphtyl, more preferably 2-naphthyl and a group EDS.

26. The compound or salt of any of items 1 to 25, wherein X³ is an amide bond or a group of the formula

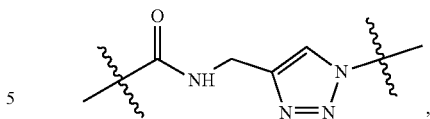

wherein the marked bond at the carbonyl group attaches X³ to R$^M$ and the other marked bond attaches X³ to the remainder of the molecule.

27. The compound or salt of item 26, wherein X³ is an amide bond —C(O)—NH— with the carbon atom being attached to R$^M$.

28. The compound or salt of any of items 1 to 27, wherein R$^M$ is a chelating group optionally containing a chelated non-radioactive or radioactive cation.

29. The compound or salt of any of items 1 to 28, wherein the chelating group comprises at least one of
 (i) a macrocyclic ring structure with 8 to 20 ring atoms of which 2 or more, preferably 3 or more, are selected from oxygen atoms, sulfur atoms and nitrogen atoms; and
 (ii) an acyclic, open chain chelating structure with 8 to 20 main chain atoms of which 2 or more, preferably 3 or more are heteroatoms selected from oxygen atoms, sulfur atoms and nitrogen atoms.

30. The compound or salt of any of items 1 to 29, wherein the chelating group is a residue of a chelating agent selected from bis(carboxymethyl)-1,4,8,11-tetraazabicyclo[6.6.2]hexadecane (CBTE2a), cyclohexyl-1,2-diaminetetraacetic acid (CDTA), 4-(1,4,8,11-tetraazacyclotetradec-1-yl)-methylbenzoic acid (CPTA), N'-[5-[acetyl(hydroxy)amino]pentyl]-N-[5-[[4-[5-aminopentyl-(hydroxy)amino]-4-oxobutanoyl]amino]pentyl]-N-hydroxybutandiamide (DFO), 4,11-bis(carboxymethyl)-1,4,8,11-tetraazabicycle[6.6.2]hexadecan (DO2A) 1,4,7,10-tetraazacyclododecan-N,N',N'',N'''-tetraacetic acid (DOTA), 2-[1,4,7,10-tetraazacyclododecane-4,7,10-triacetic acid]-pentanedioic acid (DOTAGA), N,N'-dipyridoxylethylendiamine-N,N'-diacetate-5,5'-bis(phosphat) (DPDP), diethylenetriaminepentaacetic acid (DTPA), ethylenediamine-N,N'-tetraacetic acid (EDTA), ethyleneglykol-O,O-bis(2-aminoethyl)-N,N,N',N'-tetraacetic acid (EGTA), N,N-bis(hydroxybenzyl)-ethylenediamine-N,N'-diacetic acid (HBED), hydroxyethyldiaminetriacetic acid (HEDTA), 1-(p-nitrobenzyl)-1,4,7,10-tetraazacyclodecan-4,7,10-triacetate (HP-DOA3), 6-hydrazinyl-N-methylpyridine-3-carboxamide (HYNIC), 1,4,7-triazacyclononan-1-succinic acid-4,7-diacetic acid (NODASA), 1-(1-carboxy-3-carboxypropyl)-4,7-(carbooxy)-1,4,7-triazacyclononane (NODAGA), 1,4,7-triazacyclononanetriacetic acid (NOTA), 4,11-bis(carboxymethyl)-1,4,8,11-tetraazabicyclo[6.6.2]hexadecane (TE2A), 1,4,8,11-tetraazacyclododecane-1,4,8,11-tetraacetic acid (TETA), terpyridin-bis(methyleneamintetraacetic acid (TMT), 1,4,7,10-tetraazacyclotridecan-N,N',N'',N'''-tetraacetic acid (TRITA), and triethylenetetraaminehexaacetic acid (TTHA), N,N'-bis[(6-carboxy-2-pyridil)methyl]-4,13-diaza-18-crown-6 (H₂macropa) and 4-amino-4-{2-[(3-hydroxy-1,6-dimethyl-4-oxo-1,4-dihydro-pyridin-2-ylmethyl)-carbamoyl]-ethyl}heptanedioic acid bis-[(3-hydroxy-1,6-dimethyl-4-oxo-1,4-dihydro-pyridin-2-ylmethyl)-amide] (THP);
 which residue is provided by covalently binding a carboxyl group contained in the chelating agent to the remainder of the compound via an ester or an amide bond, more preferably an amide bond.

31. The compound or salt of item 30, wherein the chelating agent is selected from DOTA and DOTAGA.
32. The compound or salt of item 30 or 31, wherein $X^3$ is the amide bond attaching the chelating group to the remainder of the molecule.
33. The compound or salt of item 32, wherein $R^M$—$X^3$— is a group of the formula

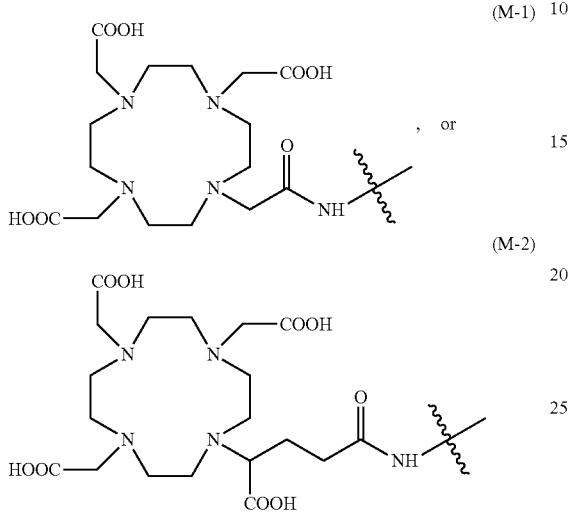

wherein the bond marked with ⌇⌇⌇ is attached to the remainder of the compound of formula (I), and wherein the chelating group may contain a chelated non-radioactive or radioactive cation.

34. The compound or salt of any of items 1 to 33, wherein the chelating group comprises a chelated cation, preferably a chelated radioactive cation selected from the cations of $^{44}$Sc, $^{47}$Sc, $^{51}$Cr, $^{52m}$Mn, $^{58}$Co, $^{52}$Fe, $^{56}$Ni, $^{57}$Ni, $^{62}$Cu, $^{64}$Cu, $^{67}$Cu, $^{66}$Ga, $^{68}$Ga, $^{67}$Ga, $^{89}$Zr, $^{90}$Y, $^{89}$Y, $^{94m}$Tc, $^{99m}$Tc, $^{97}$Ru, $^{105}$Rh, $^{109}$Pd, $^{111}$Ag, $^{110m}$In, $^{111}$In, $^{113m}$In, $^{114m}$In, $^{117m}$Sn, $^{121}$Sn, $^{127}$Te, $^{142}$Pr, $^{143}$Pr, $^{149}$Pm, $^{151}$Pm, $^{149}$Tb, $^{153}$Sm, $^{157}$Gd, $^{161}$Tb, $^{166}$Ho, $^{165}$Dy, $^{169}$Er, $^{169}$Yb, $^{175}$Yb, $^{172}$Tm, $^{177}$Lu, $^{186}$Re, $^{188}$Re, $^{191}$Pt, $^{197}$Hg, $^{198}$Au, $^{199}$Au, $^{212}$Pb, $^{203}$Pb, $^{211}$At, $^{212}$Bi, $^{213}$Bi, $^{223}$Ra, $^{225}$Ac, and $^{227}$Th, or a cationic molecule comprising $^{18}$F, such as $^{18}$F—[AlF]$^{2+}$.
35. The compound or salt of item 34, wherein the chelating group comprises a chelated cation selected from the cations of $^{44}$Sc, $^{47}$Sc, $^{64}$Cu, $^{67}$Cu, $^{68}$Ga, $^{90}$Y, $^{111}$In, $^{161}$Tb, $^{166}$Ho, $^{177}$Lu, $^{188}$Re, $^{212}$Pb, $^{212}$Bi, $^{213}$Bi, $^{225}$Ac, and $^{227}$Th or a cationic molecule comprising $^{18}$F.
36. The compound or salt of any of items 1 to 35, wherein the compound of formula (I) contains one or two groups EDS.
37. The compound or salt of item 36, wherein the compound of formula (I) either contains one group EDS which is carried by the linking group $L^1$, or contains two groups EDS, one being represented by $R^4$ and one being carried by $L^1$.
38. The compound or salt of any of items 1 to 37, wherein, in the group EDS (E-1A), the substituents $R^{5A}$ are the same for s>1 and are selected from —NO$_2$ and —COOH; and wherein, in the group EDS (E-2A), the substituents $R^{6A}$ are the same for t>1 and are selected from —NO$_2$ and —COOH.
39. The compound or salt of any of items 1 to 38, wherein, in the group EDS (E-1B), the substituents $R^{5B}$ are the same for s>1 and are selected from —OH and —NH$_2$; in the group EDS (E-2B), the substituents $R^{6B}$ are the same for t>1 and are selected from —OH and —NH$_2$.
40. The compound or salt of any of items 1 to 39, which contains a group EDS which has the formula (E-2A):

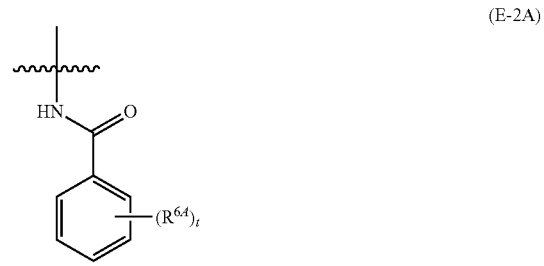

wherein ⌇⌇⌇ marks the bond which attaches the group EDS to the remainder of the compound of formula (I); and
t is 1 or 2, and $R^{6A}$ is selected from —NO$_2$ and —COOH.

41. The compound of any of items 1 to 38, wherein the group EDS has the formula (E-3)

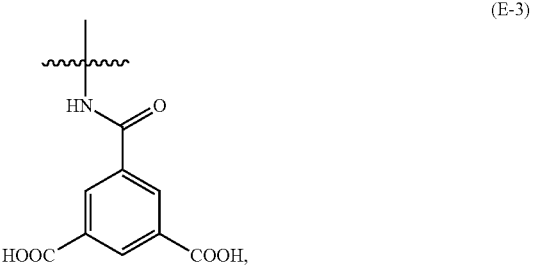 [SMILES: *NC(=O)c1cc(C(=O)O)cc(C(=O)O)c1]

wherein ⌇⌇⌇ marks the bond which attaches the group EDS to the remainder of the compound of formula (I).

42. The compound of any of items 1 to 41, which has the following formula (Ia), or a pharmaceutically acceptable salt thereof:

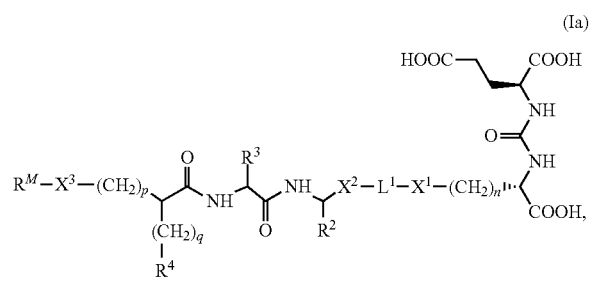

wherein n, $X^1$, $L^1$, $X^2$, $R^2$, $R^3$, $R^4$, q, p, $X^3$ and $R^M$ are defined as in the preceding items, and wherein the group EDS is contained at least once and has a structure as defined in the preceding items.

43. The compound of item 42, which has the following formula (Ib), or a pharmaceutically acceptable salt thereof:

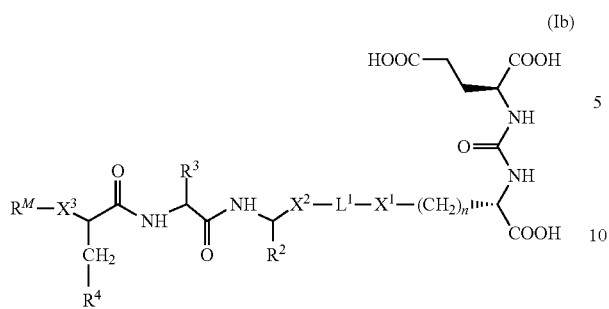

(Ib)

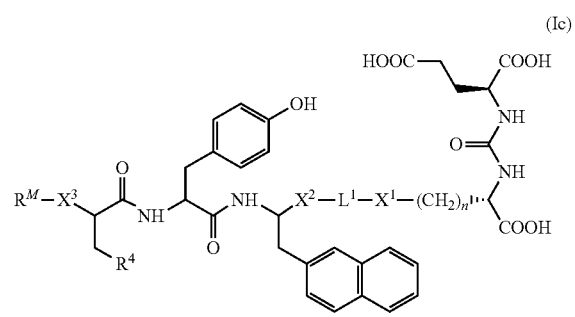

(Ic)

wherein n, $X^1$, $L^1$, $X^2$, $R^2$, $R^3$, $R^4$, $X^3$ and $R^M$ are defined as in the preceding items, and wherein the group EDS is contained at least once and has a structure as defined in the preceding items.

44. The compound of any of item 43, which has the following formula (Ic), or a pharmaceutically acceptable salt thereof:

wherein n, $X^1$, $L^1$, $X^2$, $R^4$, $X^3$ and $R^M$ are defined as in the preceding items, and wherein the group EDS is contained at least once and has a structure as defined in the preceding items.

45. The compound of item 44, which has the following formula (Id) or (Ie), or a pharmaceutically acceptable salt thereof:

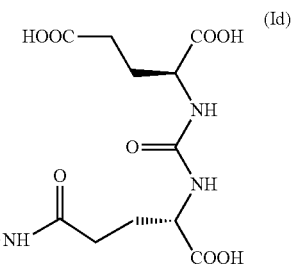

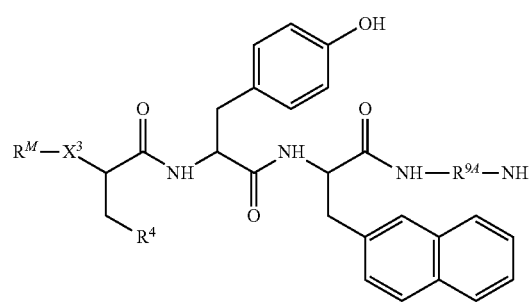

(Id)

wherein $R^{9A}$, $R^{10A}$, $R^{11A}$, $R^4$, $X^3$ and $R^M$ are defined as in the preceding items, and wherein either (i) R4 is a group EDS with a structure as defined in the preceding items, or (ii) $R^{10A}$ carries one group EDS with a structure as defined in the preceding items, or both (i) and (ii) apply;

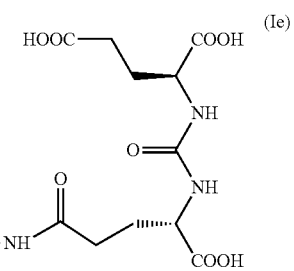

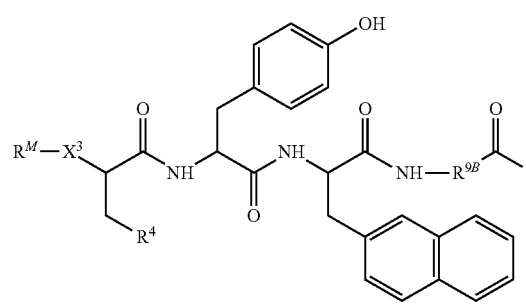

(Ie)

wherein $R^{9B}$, $R^{10B}$, $R^{11B}$, $R^4$, $X^3$ and $R^M$ are defined in the preceding items, and wherein $R^4$ is a group EDS with a structure as defined in the preceding items.

46. The compound of item 45, which has the following formula (If) or (Ig), or a pharmaceutically acceptable salt thereof:

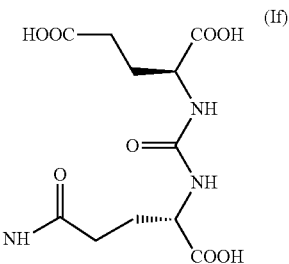
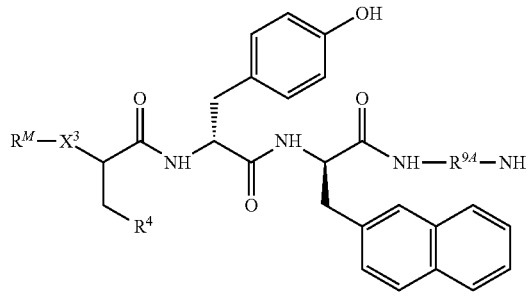

wherein $R^{9A}$, $R^{10A}$, $R^{11A}$, $R^4$, $X^3$ and $R^M$ are defined as in the preceding items, and wherein either (i) R4 is a group EDS with a structure as defined in the preceding items, or (ii) $R^{10A}$ carries one group EDS with a structure as defined in the preceding items, or both (i) and (ii) apply;

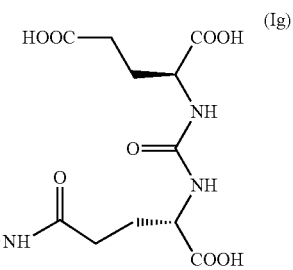
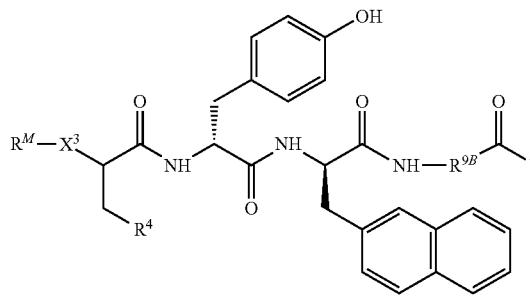

wherein $R^{9B}$, $R^{10B}$, $R^{11B}$, $R^4$, $X^3$ and $R^M$ are defined as in the preceding items, and wherein $R^4$ is a group EDS with a structure as defined in the preceding items.

47. The compound or salt thereof of any item 1, wherein said compound or salt has one of the following formulae:

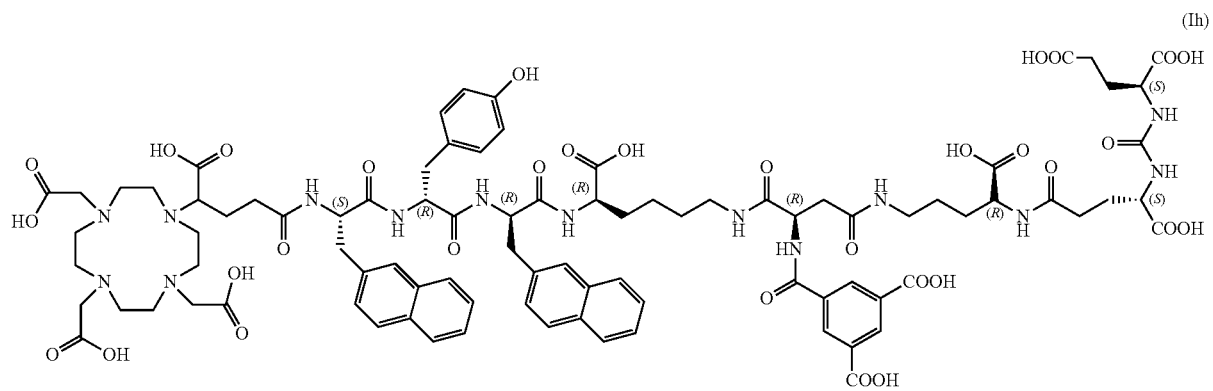

-continued
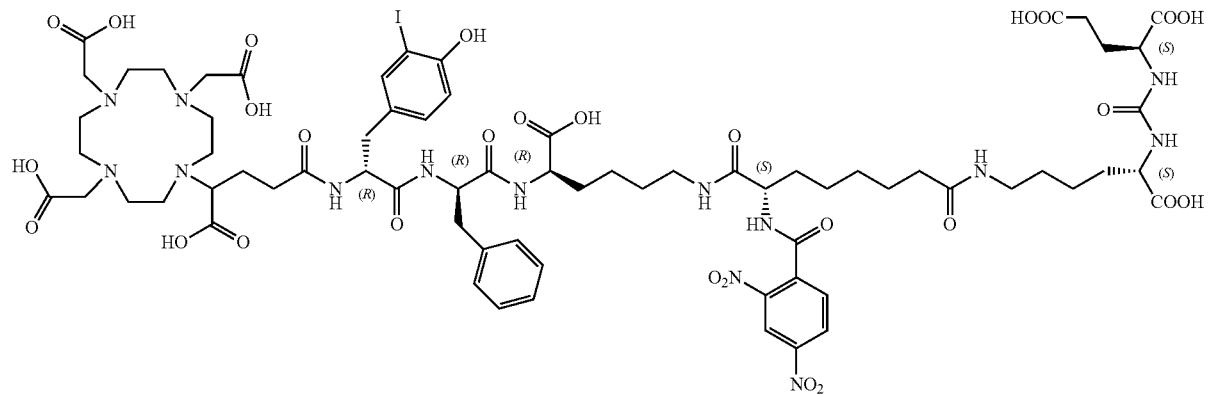
(Ii)
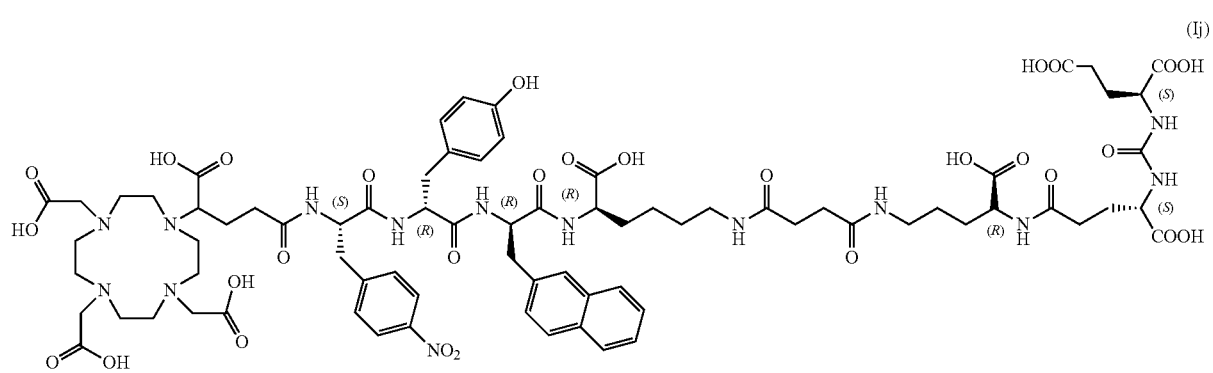
(Ij)
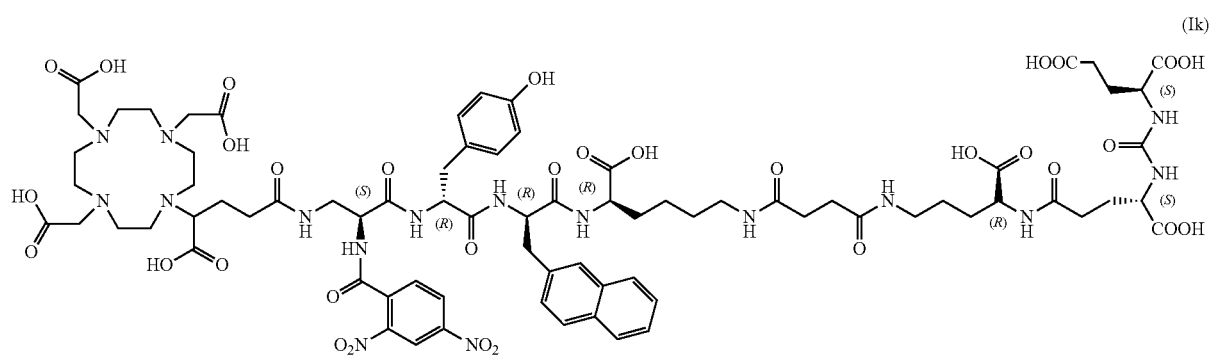
(Ik)
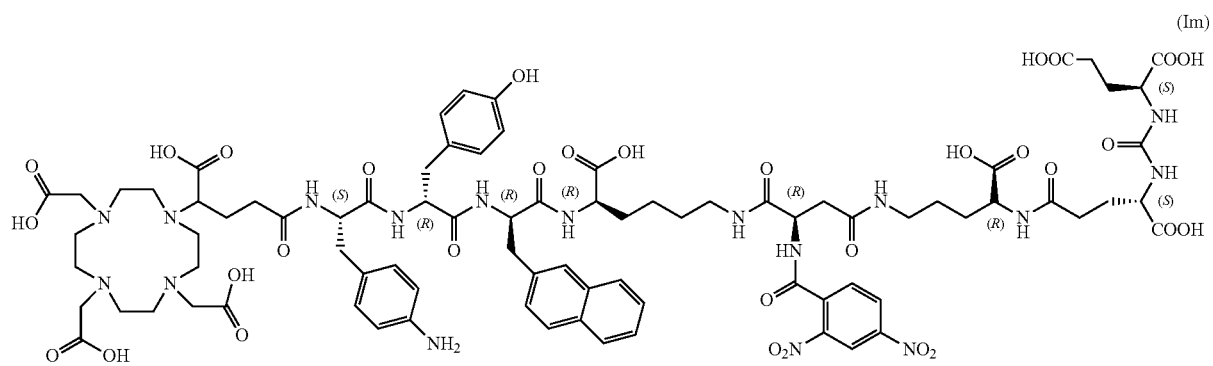
(Im)

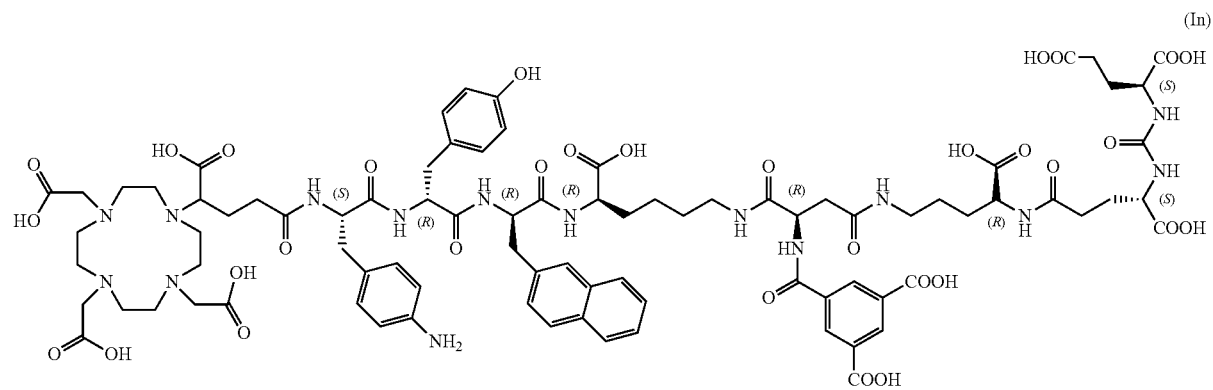
(In)
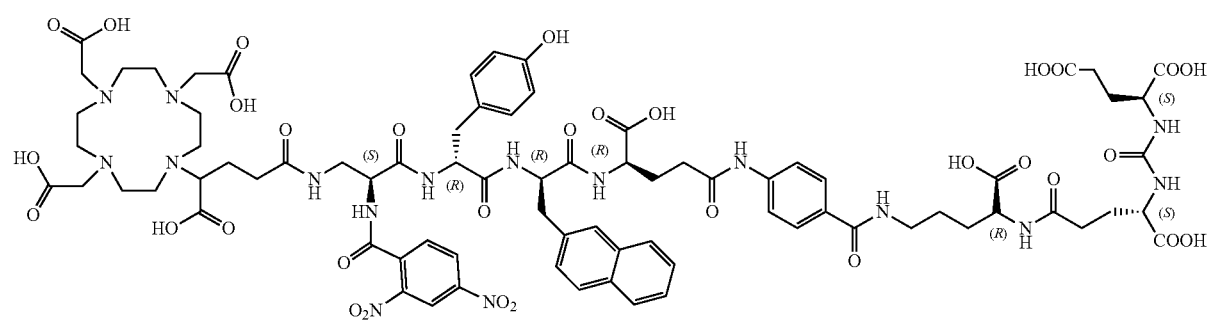
(Io)
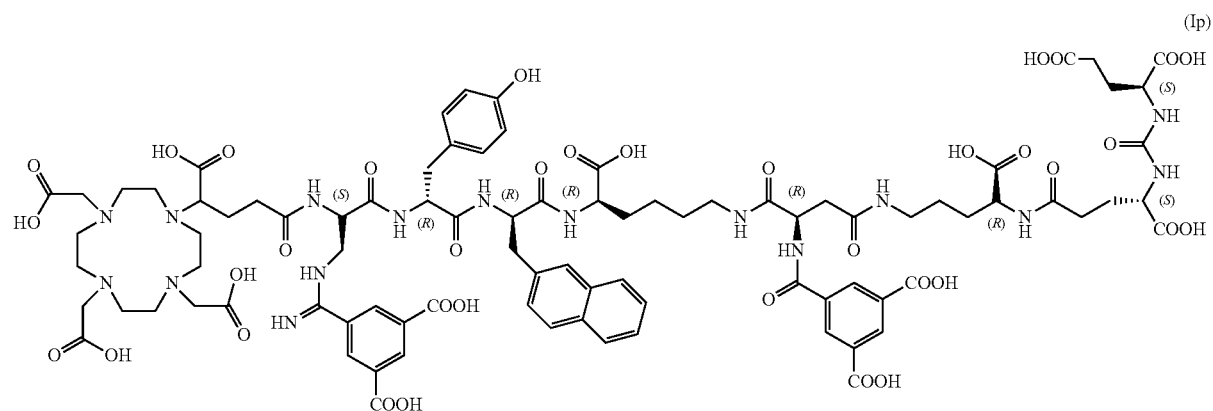
(Ip)
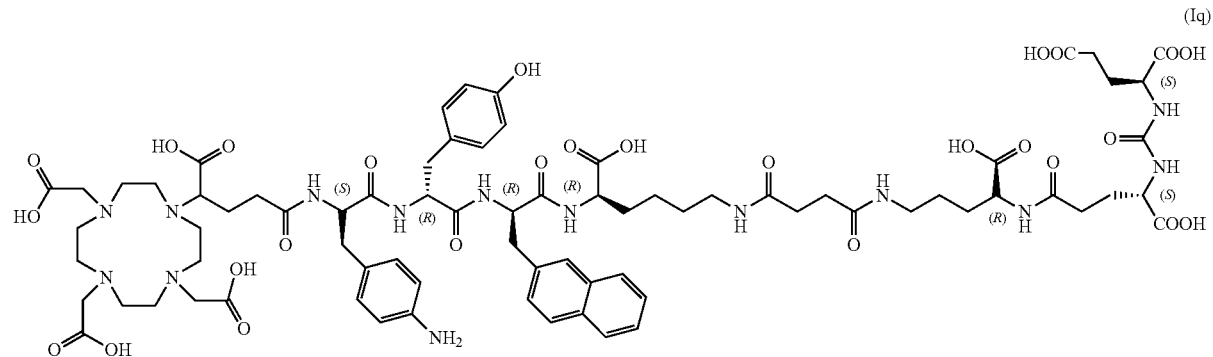
(Iq)

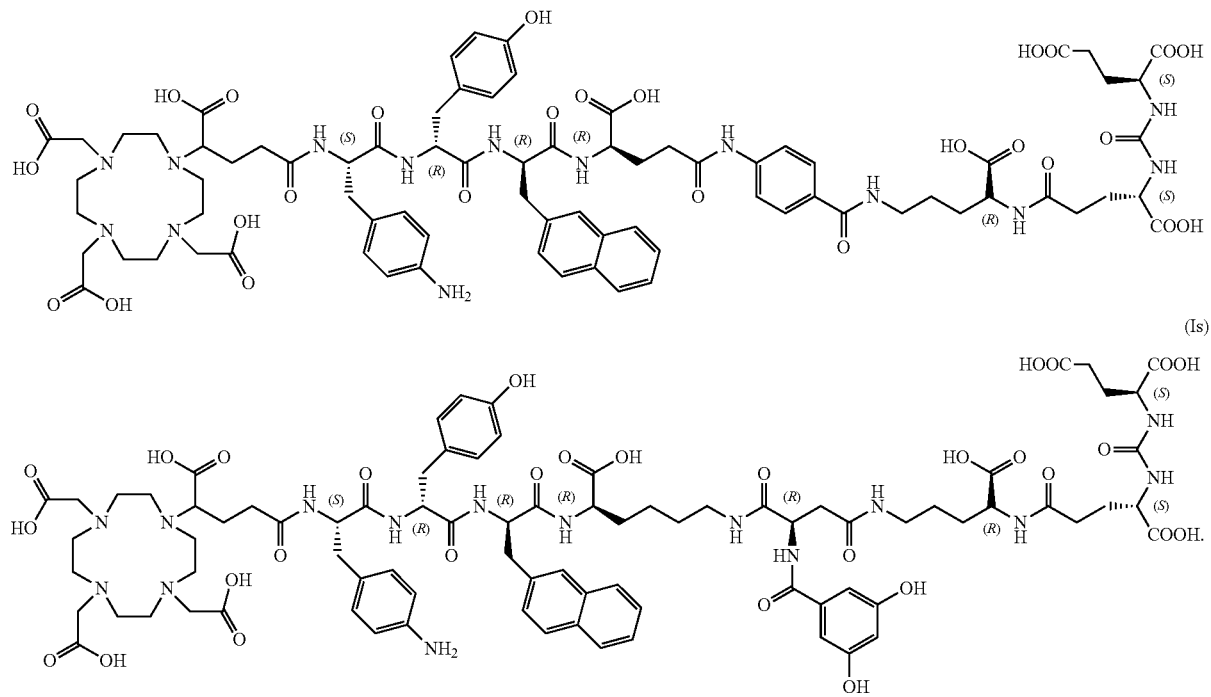

48. A pharmaceutical or diagnostic composition comprising or consisting of one or more compounds or salts in accordance with any one of items 1 to 47.
49. A compound or salt in accordance with any one of items 1 to 47 for use in a method of diagnosing and/or treating
    (a) cancer including prostate cancer; or
    (b) neoangiogenesis/angiogenesis.

The figures show:

FIG. 1: Web chart of characteristics for [$^{nat/177}$Lu]PSMA I&T and [$^{nat/177}$Lu]PSMA-62 and [$^{nat/177}$Lu]PSMA-66.

Figure 2:
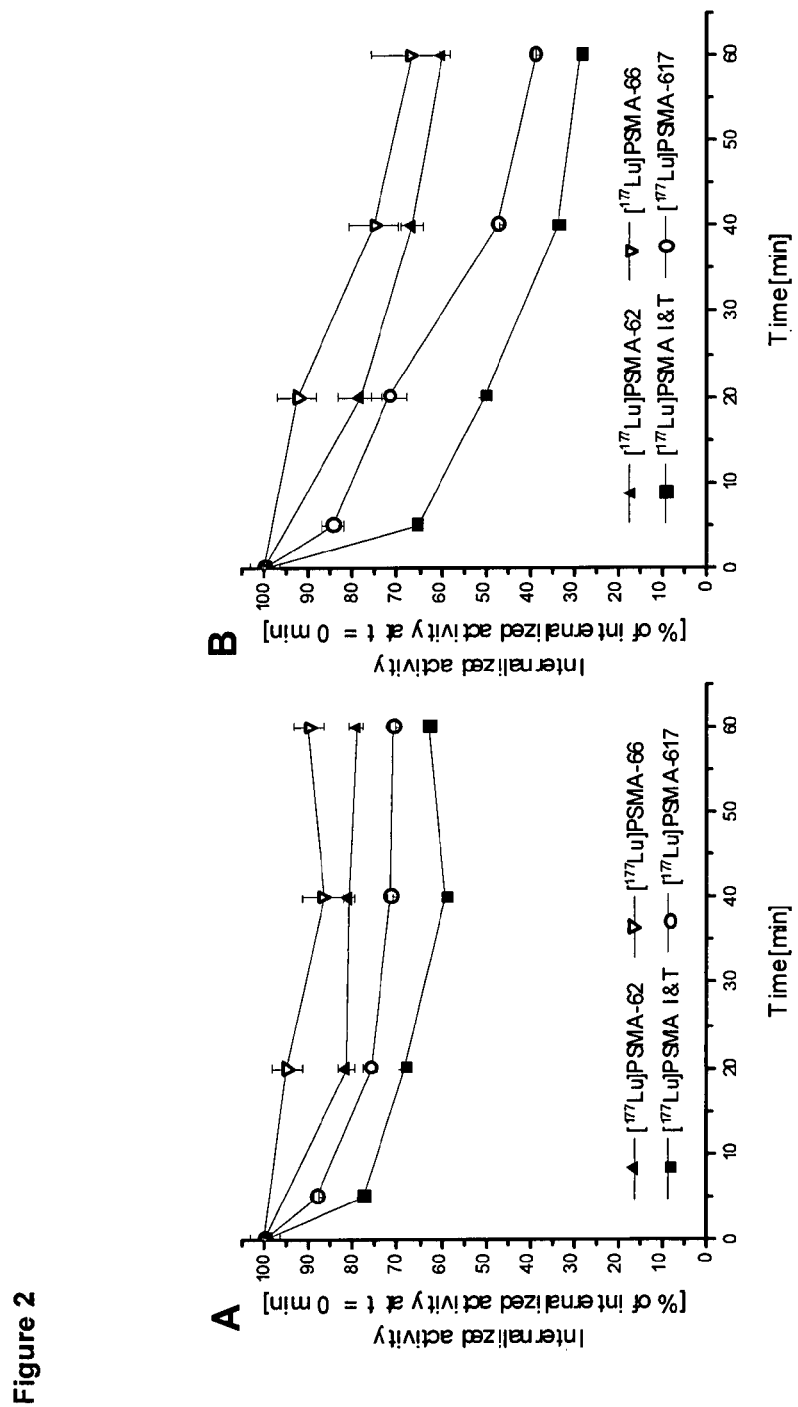

FIG. 2: Externalization kinetics of selected $^{177}$Lu-labeled PSMA inhibitors from LNCaP cells. 1.25*10$^5$ cells/well were incubated 1 h with the respective radioligand (c=1.0 nm) at 37° C. in DMEM-solution (5% BSA). Then, the supernatant was removed and once washed with DMEM-solution (5% BSA, 37° C.). Afterwards, either A) only DMEM-solution (5% BSA) or B) blockade DMEM-solution (5% BSA, 10 μm 2-PMPA) were added for replacement. The total cellular internalized activity at t=0 min was corrected for non-specific binding (10 μm 2-PMPA) and normalized to 100%. All data are expressed as mean±SD (n=3).

Figure 3:
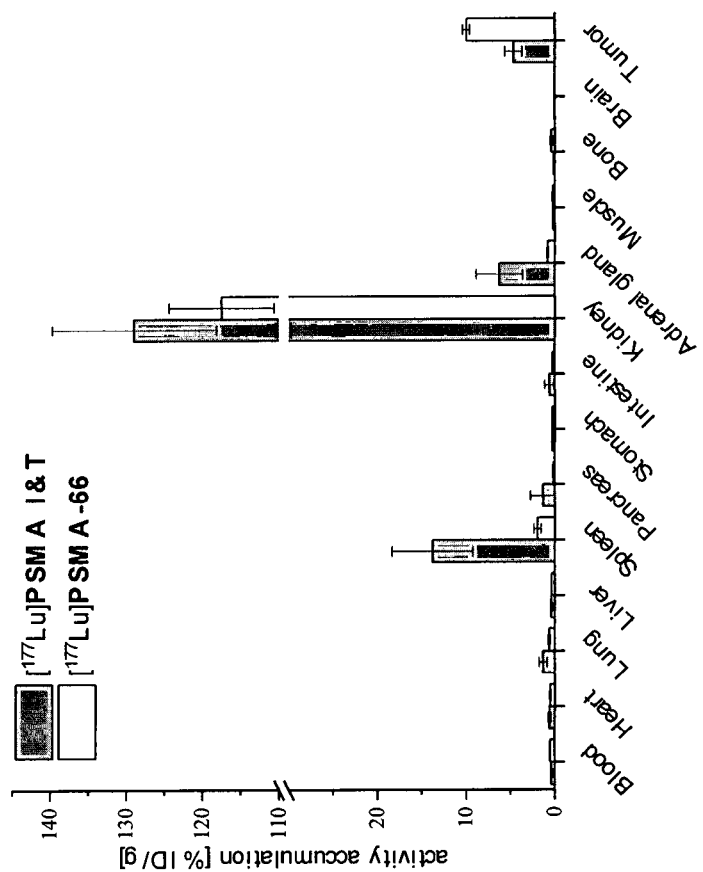

FIG. 3: Biodistribution (in % ID/g) of 2.5 to 3.0 MBq (0.15 to 0.25 nmol) of [$^{177}$Lu]PSMA-66 and [$^{177}$Lu]PSMA I&T in LNCaP-tumor bearing CB-17 SCID mice (n=4, respectively).

Figure 4:
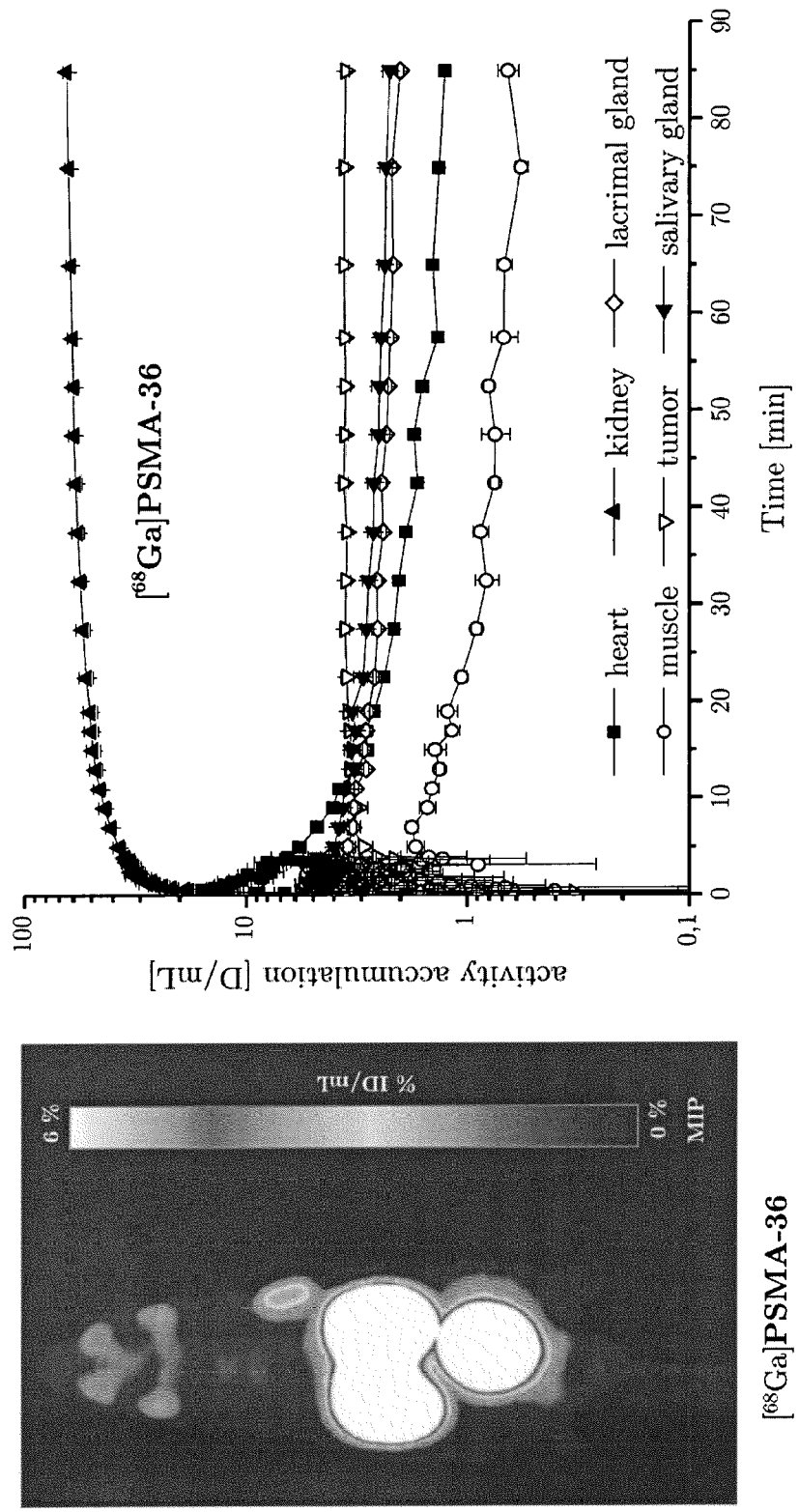

FIG. 4: Maximum intensity projection (MIP) of a μPET scan in LNCaP-tumor bearing CB-17 SCID mice after injection of approx. 10.3 MBq (0.19 nmol tracer) of [$^{68}$Ga]PSMA-36 (dynamic scan, summed up frames 1 to 1.5 h p.i.) (top left). TACs (logarithmic plot) in % ID/mL of [$^{68}$Ga]PSMA-36 derived from dynamic PET data (90 min acquisition time, OSEM 3D reconstruction) in a LNCaP-tumor bearing CB-17 SCID mouse of blood pool (heart), kidney, tumor, muscle, lacrimal- and salivary gland.

Figure 5:
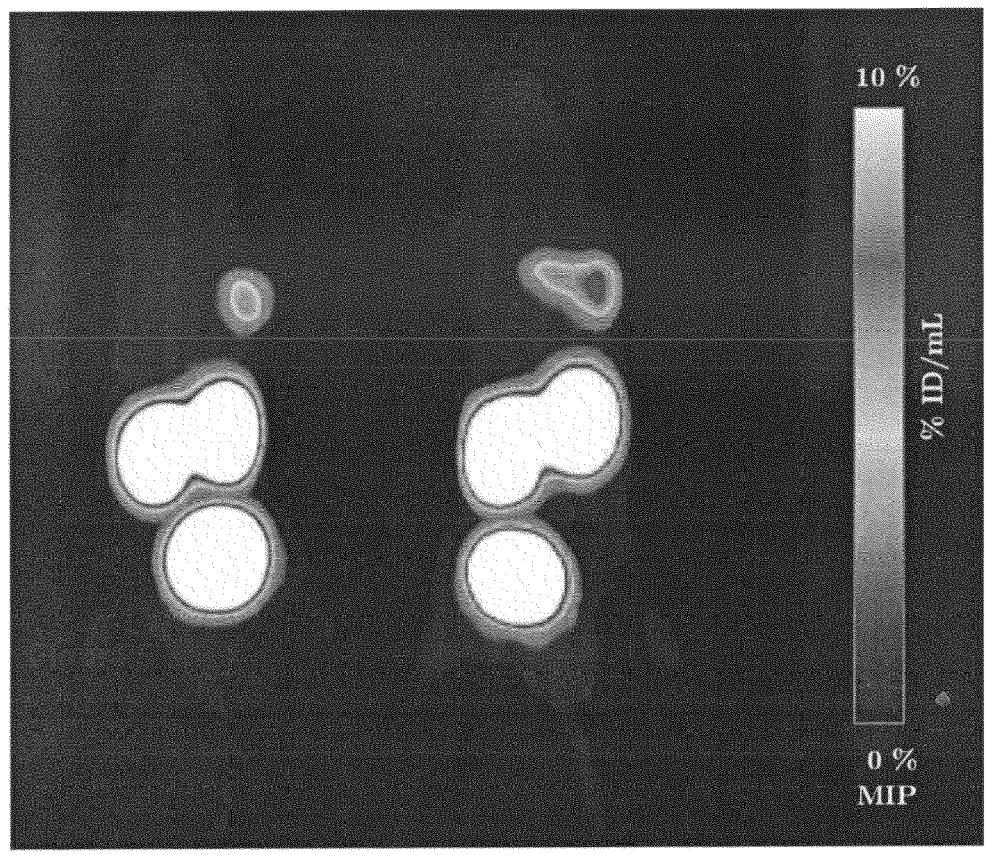
Figure 5:
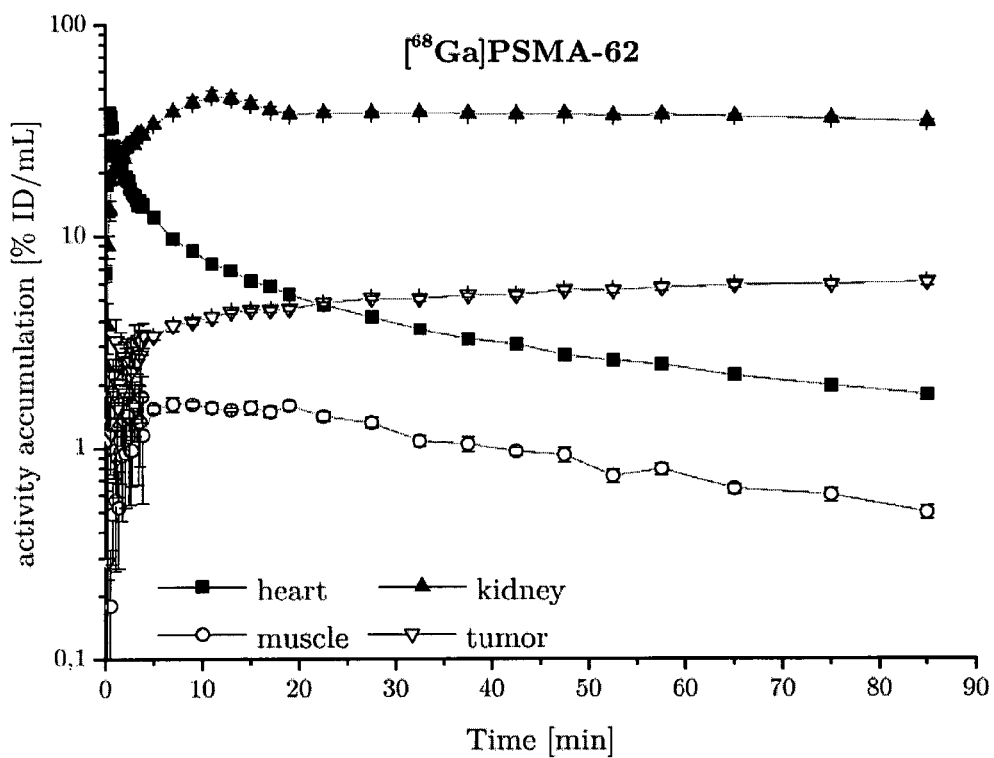
Figure 5:
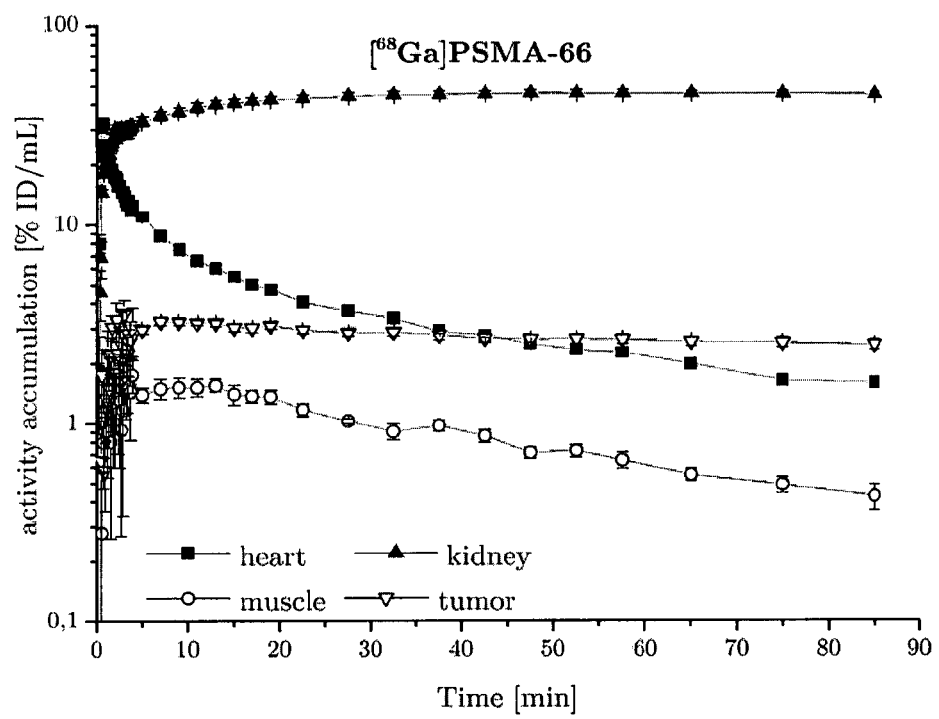

FIG. 5: Maximum intensity projection (MIP) of μPET scans in LNCaP-tumor bearing CB-17 SCID mice after injection of approx. 11 and 13 MBq (0.15 to 0.25 nmol tracer) of the $^{68}$Ga-labeled PSMA inhibitor PSMA-62 and PSMA-66, respectively (dynamic scan, summed up frames 1 to 1.5 h p.i.) (top left). TACs (logarithmic plot) in % ID/mL of the respective $^{68}$Ga-labeled PSMA inhibitor derived from dynamic PET data (90 min acquisition time, OSEM 3D reconstruction) in LNCaP-tumor bearing CB-17 SCID mice of blood pool (heart), kidney, tumor and muscle for both $^{68}$Ga-labeled tracer.

Figure 6:
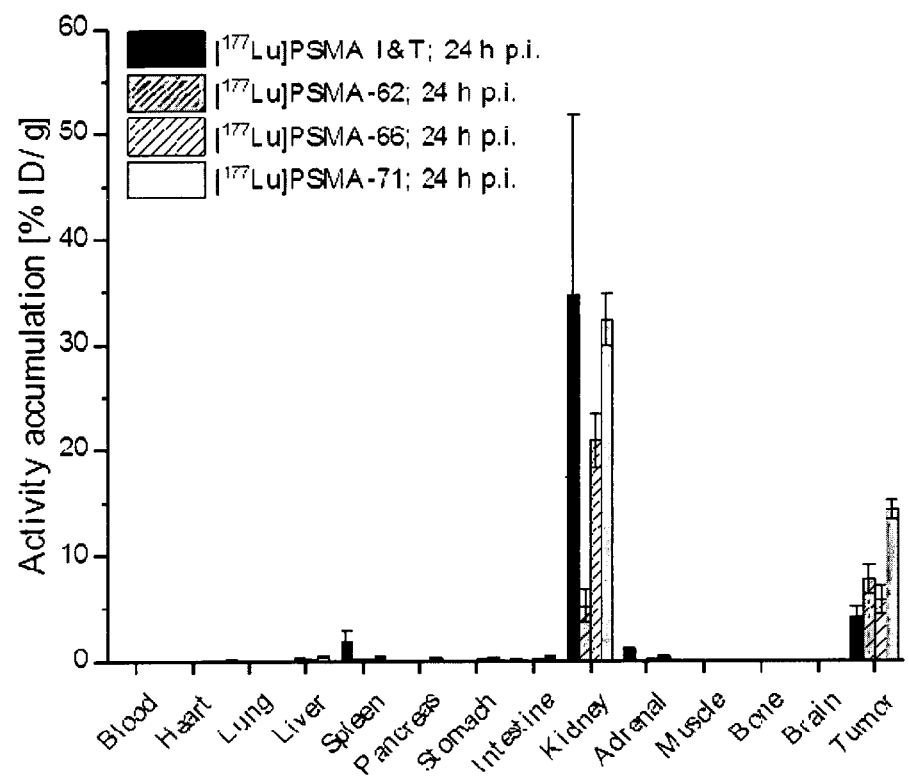

FIG. 6: Biodistribution (in % ID/g) of 2.5 to 6.0 MBq (0.15 to 0.25 nmol) of [$^{177}$Lu]PSMA-62, [$^{177}$Lu]PSMA-66, [$^{177}$Lu]PSMA-71 and [$^{177}$Lu]PSMA I&T in LNCaP-tumor bearing CB-17 SCID mice (n=4, respectively).

The examples illustrate the invention.

EXAMPLE 1: MATERIALS AND METHODS

1. General Information

The Fmoc-(9-fluorenylmethoxycarbonyl-) and all other protected amino acid analogs were purchased from Bachem (Bubendorf, Switzerland) or Iris Biotech (Marktredwitz, Germany). The 2-chlorotrityl chloride (2-CTC) resin was obtained from PepChem (Tübingen, Germany). Chematech (Dijon, France) delivered the chelator DOTAGA-anhydride. PSMA-DKFZ-617 was purchased from ABX advanced chemical compounds (Radeberg, Germany). All necessary solvents and other organic reagents were purchased from either Alfa Aesar (Karlsruhe, Germany), Sigma-Aldrich (Munich, Germany) or VWR (Darmstadt, Germany). Solid phase synthesis of the peptides was carried out by manual operation using an Intelli-Mixer syringe shaker (Neolab, Heidelberg, Germany). Analytical reversed-phase high performance liquid chromatography (RP-HPLC) was performed on a Nucleosil 100 C18 column (5 μm, 125×4.0 mm, CS GmbH, Langerwehe, Germany) using a Shimadzu gradient RP-HPLC System (Shimadzu Deutschland GmbH, Neufahrn, Germany). Analysis of the peptides was performed by applying different gradients of 0.1% (v/v) trifluoroacetic acid (TFA) in $H_2O$ (solvent A) and 0.1% TFA together with (v/v) in acetonitrile (MeCN) (solvent B) with a constant flow of 1 mL/min (specific gradients are cited in the text). The Shimadzu SPD 20 A prominence UV/VIS detector (Shimadzu Deutschland GmbH) was used at λ=220 nm and 254 nm. HSA binding was determined using a Chiralpak HSA (5 μm, 50×3 mm) analytical column connected to a Chiralpak HSA (5 μm, 10×3 mm) guard cartridge (Daicel Chemical Industries) purchased from Chiral Technologies Europe (Illkirch, France). Non-linear regression for the HSA binding was performed using OriginPro 2016G (Northampron, USA). Retention times $t_R$ as well as the capacity factors K' are cited in the text. Preparative RP-HPLC of the peptides was achieved on a Shimadzu RP-HPLC system using a Multospher 100 RP 18-5 column (250×20 mm, CS GmbH) with a constant flow of 5 mL/min. Analytical and preparative Radio RP-HPLC of the radioiodinated reference ligand was performed using a Nucleosil 100 C18 column (5 μm, 125×4.0 mm). Radioactivity was detected through connection of the outlet of the UV-photometer to a NaI(TI) well-type scintillation counter from EG&G Ortec (Munich, Germany). The $^{68}$Ga- and $^{177}$Lu-labeled compounds were analyzed as published previously [1, 2]. Electrospray ionization mass spectrometry (ESI-MS) spectra were acquired on an expression$^L$ CMS mass spectrometer (Advion Ltd., Harlow, UK) and on a Varian 500-MS IT mass spectrometer (Agilent Technologies, Santa Clara, USA). For the Bradford-Assay a V-630 UV-Vis spectrophotometer from JASCO Germany GmbH (Gross-Umstadt, Germany) was used and centrifugation of the S9-fractions was performed in an Avanti JXN-26 centrifuge from Beckman Coulter GmbH (Krefeld, Germany). The centrifugation of the radioactive S9-metabolite assays was performed using a Heraeus PICO 17 centrifuge from Thermo Fisher Scientific Messtechnik GmbH (Munich, Germany). NMR Data were obtained applying 300 K using an AV 300 (300 MHz) or an AV 400 (400 MHz) from Bruker (Billerica, USA). The incubation of the S9-fractions for ex vivo metabolite analysis was performed in a Biometra UNO Thermoblock (Biometra, Göttingen, Deutschland).

2. Synthesis Protocols (SP)

SP-1:

2-CTC-resin loading: 2-CTC-resin (1.6 mmol/g) is loaded with Fmoc-AA-OH (1.5 eq.) in anhydrous dichloromethane (DCM) with N,N-Diisopropylethylamine (DIPEA) (4.5 eq.) at room temperature (RT) for 2 h. The remaining tritylchloride is capped by addition of 2 mL/g methanol (MeOH) for 15 min. After that, the resin is filtered and thoroughly washed with DCM ($2^x$), with dimethylformamide (DMF) ($2^x$) and MeOH ($2^x$), respectively and stored under vacuum overnight. The loading is determined using the weight differences:

$$\frac{(m_{total} - m_{net\,weight}) \times 1000}{(M_{As} - M_{HCl}) \times m_{Weight\,of\,resin}} = mmol/g.$$  Formula 1

Determination of resin-loading $m_{total}$: mass
of loaded resin (Fmoc-AA-OH and HCl);

$M_{As}$: molar mass of amino acid;

$m_{net}$ weight: mass of used resin;

$M_{HCl}$: molar mass of hydrochloric acid

SP-2:

Peptide synthesis via TBTU/HOBt coupling: A solution of Fmoc-AA-OH (2.0 eq.), N,N,N',N'Tetramethyl-O-(benzotriazol-1-yl)uronium tetrafluoroborate (TBTU) (2.0 eq.), N-Hydroxybenzotriazole (HOBt) (2.0 eq.), DIPEA (4.5 eq.) in DMF (8 ml/g resin) was added to the resin-bound free amine peptide and shaken for 2 h at RT and washed with DMF ($6^x$). The coupling with secondary or aromatic amines was performed employing a different protocol. Fmoc-AA-OH (3.0 eq.) was dissolved in DMF (8 mL/g resin) together with 1-[Bis(dimethylamino)methylene]-1H-1,2,3-triazolo[4,5-b]pyridinium 3-oxid hexafluoro-phosphate (HATU) (3.0 eq.), 1-Hydroxy-7-azabenzotriazol (HOAt) (3.0 eq.) and DIPEA (6.0 eq.) and stirred for 15 min. The pre-activated solution was added to the resin bound peptide and shaken for 2 h at RT. After completion of the reaction, the resin was washed with DMF ($6^x$). In general, all peptidic scaffolds were synthesized as previously described (Weineisen, M.; Schottelius, M.; Simecek, J.; Eiber, M.; Schwaiger, M.; Wester, H. Development and first in human evaluation of PSMA I&T-A ligand for diagnostic imaging and endoradiotherapy of prostate cancer. *Journal of Nuclear Medicine* 2014, 55, 1083-1083; Weineisen, M.; Simecek, J.; Schottelius, M.; Schwaiger, M.; Wester, H.-J. Synthesis and preclinical evaluation of DOTAGA-conjugated PSMA ligands for functional imaging and endoradiotherapy of prostate cancer. *EJNMMI research* 2014, 4, 1.).

SP-3:

On-resin Fmoc-deprotection: The resin-bound Fmoc-protected peptide was treated with 20% piperidine in DMF (v/v) for 5 min and a second time for 15 min. Afterwards, the resin was washed thoroughly with DMF ($8^x$).

SP-4:

On-resin Dde-deprotection: The N-(1-(4,4-dimethyl-2,6-dioxocyclohexylidene)-ethyl) (Dde) protected peptide (1.0 eq.) was dissolved in a solution of 2.0% hydrazine monohydrate ($N_2H_4 \cdot H_2O$) in DMF (v/v). After 15 min, the deprotected peptide, if bound to resin, was washed with DMF ($6^x$) or precipitated in diethyl ether ($Et_2O$) to give the crude product. If Fmoc- and Dde-protecting groups were present and only Dde-deprotection was necessary, the resin-loaded peptide was treated with a solution containing $NH_2OH \cdot HCl$ (630 mg), imidazole (460 mg), DCM (0.5 mL), DMF (0.5 mL) and N-methyl-2-pyrrolidone (NMP) (2.5 mL) for 3 h at RT. Afterwards, the resin-loaded peptide was washed with DMF ($6^x$).

SP-5:

On-resin Alloc/Allyl-deprotection: The Alloc/Allyl-protecting group was removed from the resin-bound peptide using a solution of DCM (6.0 mL) containing triisopropylsilane (TIPS) (50.0 eq.) and (triphenyl)palladium(0) (Pd($PPh_3$)$_4$) (0.3 eq.). The resin was treated with this solution for 1.5 h at RT. Finally, the resin was washed with DCM ($3^x$) to remove the Pd($PPh_3$)$_4$.

SP-6:

tBu/Boc deprotection: Removal of the tert-butyl (tBu)/tert-butyloxycarbonyl (Boc)-protecting groups was carried out by dissolving the crude product in TFA (approx. 500 μL) and stirring for 40 min at RT. Afterwards, the TFA was almost completely removed using nitrogen stream. After precipitation in $Et_2O$, the crude product was centrifuged and the supernatant removed. The dried pellet was further used for the following synthesis-steps.

SP-7.1: A) Peptide Cleavage from the Resin with Preservation of Side-Chain Protecting Groups:

The fully protected, resin-bound peptide was dissolved in a mixture of DCM/trifluoroethanol (TFE)/acetic acid (AcOH) (6/3/1; v/v/v) and shaken for 30 min. The solution was filtered off and the resin was dissolved in another cleavage solution for another 30 min. The fractions were combined and the solvent was concentrated under reduced pressure. The filtrate was redissolved in toluene and concentrated under reduced pressure to remove the AcOH. Precipitation in water or $Et_2O$ resulted in the crude, side chain protected peptide.

SP-7.2: B) Peptide Cleavage from the Resin with Concurrent Deprotection of all Acid Labile Protecting Groups:

The fully protected, resin-bound peptide was dissolved in a mixture of TFA/TIPS/water (95/2.5/2.5; v/v/v) and shaken for 30 min. The solution was filtered off and the resin was treated in the same way for another 30 min. Afterwards, the fractions were combined and the solvent was concentrated under a constant flow of nitrogen. The crude peptide was precipitated in $Et_2O$ and left to dry overnight.

SP-8:

Deacetylation of carbohydrate-moieties: Deacetylation was accomplished by dissolving the PSMA inhibitor in MeOH containing KCN (0.5 eq.) (Herzig, J.; Nudelman, A.; Gottlieb, H. E.; Fischer, B. Studies in sugar chemistry. 2. A simple method for 0-deacylation of polyacylated sugars. *The Journal of Organic Chemistry* 1986, 51, 727-730.) with concomitant stirring overnight at RT. The final product was purified by RP-HPLC.

SP-9: Preparation of Non-Radioactive Metal-Complexed PSMA Inhibitors:

Sp-9.1: $^{Nat}Ga$-Compounds:

For the preparation of the $^{nat}Ga^{III}$-complexes, a 2.0 mm aqueous (aq.) solution of the PSMA inhibitor (50 μL) and a 2.0 mm aq. solution of $Ga(NO_3)_3$ (50 μL) were mixed and heated at 40° C. for 30 min. The chelate formation was assessed using RP-HPLC and ESI-MS. The resulting 1.0 mm solution was diluted and used for in vitro $IC_{50}$ determination and HSA binding.

Sp-9.2: $^{Nat}Lu$-Compounds:

The corresponding $^{nat}Lu^{III}$-complexes were prepared from a 2.0 mm aqueous solution of the PSMA inhibitor with a 2.5 molar excess of $LuCl_3$ (20 mm aq. solution) and heated to 95° C. for 30 min. After cooling, the $^{nat}Lu^{III}$-chelate formation was confirmed using RP-HPLC and ESI-MS. The resulting 1.0 mm aqueous solutions of the respective $^{nat}Lu$-complexes were then diluted and used in the in vitro $IC_{50}$ studies without further processing.

3. Building Blocks for PSMA-36 and the EuE Based PSMA Inhibitors

Di-tert-butyl(((s)-6-amino-1-(tert-butoxy)-1-oxo-hexan-2-yl)carbamoyl)-L-glutamate

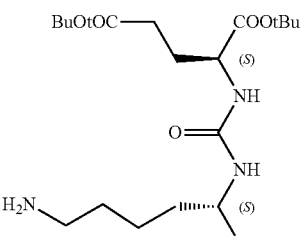

Chemical Formula: $C_{24}H_{45}N_3O_7$
Molecular Weight: 487,64

$((OtBu)KuE(OtBu)_2)$ (1)

The synthesis of the tert-butyl-protected Lys-urea-Glu binding motif (EuK) was synthesized as previously described by solution phase synthesis [3]. In short, a solution of DCM containing L-di-tert-butyl-glutamate HCl (2.0 g, 7.71 mmol, 1.0 eq.) was cooled on ice for 30 min and afterwards treated with trimethylamine (TEA) (2.69 mL, 19.28 mmol, 2.5 eq.) and 4-(dimethylamino)pyridine (DMAP) (3.3 mg, 0.3 mmol, 0.04 eq.). After additional stirring for 5.0 min, 1,1'-carbonyldiimidazole (CDI) (1.38 g, 8.84 mmol, 1.1 eq.) was dissolved in DCM and slowly added over a period of 30 min. The reaction mixture was further stirred overnight and enabled to warm to RT. The reaction was stopped using saturated (sat.) $NaHCO_3$ solution (8 mL) with concomitant washing steps of water ($2^x$) and brine ($2^x$) and dried over sat. $Na_2SO_4$ solution. The remaining solvent was removed in vacuo and the crude product (s)-Di-tert-butyl 2-(1H-imidazole-1-carboxamido)pentanedioate used without further purification. RP-HPLC (10 to 90% B in 15 min): $t_R$=12.2 min; K'=5.8. Calculated monoisotopic mass ($C_{17}H_{27}N_3O_5$): 353.4; found: m/z=376.1 $[M+Na]^+$. The crude product (s)-Di-tert-butyl 2-(1H-imidazole-1-carboxamido)pentanedioate (2.72 g, 7.71 mmol, 1.0 eq.) was dissolved in 1,2-dichloroethane (DCE) and cooled on ice for 30 min. To this solution was added TEA (2.15 mL, 15.42 mmol, 2.0 eq.) and H-Lys(Cbz)-OtBu.HCl (2.87 g, 7.71 mmol, 1.0 eq.) and the solution stirred overnight at 40° C. The remaining solvent was evaporated and the crude product purified using silica gel flash-chromatography with an eluent mixture containing ethyl acetate (EtOAc)/hexane/TEA (500/500/0.8; v/v/v). After removal of the solvent, (9R,13s)-tri-tert-butyl-3,11-dioxo-1-phenyl-2-oxa-4,10, 12-triazapentadecane-9,13,15-tricarboxylate was obtained as colorless oil. RP-HPLC (40 to 100% B in 15 min): $t_R$=14.5 min; K'=6.25. Calculated monoisotopic mass ($C_{32}H_{51}N_3O_9$)=621.8; found: m/z=622.3 $[M+H]^+$. To synthesize $(OtBu)KuE(OtBu)_2$ (1), (9R,13s)-tri-tert-butyl-3,11-dioxo-1-phenyl-2-oxa-4,10, 12-triazapentadecane-9,13,15-tricarboxylate (3.4 g, 5.47 mmol, 1.0 eq.) was dissolved in ethanol (EtOH) (75 mL) and palladium on activated charcoal (0.34 g, 0.57 mmol, 0.1 eq.) (10%) was given to this solution. The reaction mixture containing flask was initially purged with hydrogen stream and the solution allowed to stir overnight at RT under light hydrogen-pressure (balloon). The crude product was purified through celite and the solvent evaporated in vacuo. The desired product 1 was obtained as a waxy solid (1.9 g, 3.89 mmol, 71.6% yield). RP-HPLC (10 to 90% B in 15 min): $t_R$=12.6 min; K'=6.4. Calculated monoisotopic mass $(C_{24}H_{45}N_3O_7)$=487.6; found: m/z=488.3 [M+H]$^+$, 510.3 [M+Na]$^+$.

(s)-5-(tert-butoxy)-4-(3-((s)-1,5-di-tert-butoxy-1,5-dioxopentan-2-yl)ureido)-5-oxopentanoic acid ((OtBu)EuE(OtBu)$_2$) (2)

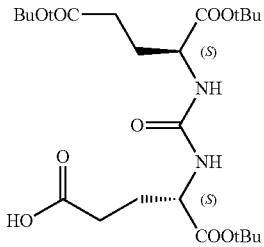

Chemical Formula: C$_{23}$H$_{40}$N$_2$O$_9$
Molecular Weight: 488,58

The synthesis of the tert-butyl-protected Glu-urea-Glu binding motif (EuE) was similarly synthesized as described for 1 [3] using H-L-Glu(OBzl)-OtBu.HCl instead of H-L-Lys(Cbz)-OtBu.HCl. The desired product was obtained as waxy and strongly hygroscopic solid (4.10 g, 8.39 mmol, 84% yield). RP-HPLC (10 to 90% B in 15 min): $t_R$=11.3 min; K'=7.69. Calculated monoisotopic mass $(C_{23}H_{49}N_2O_9)$=488.3; found: m/z=489.4 [M+H]$^+$, 516.4 [M+Na]$^+$.

(s)-NHFmoc-Asu(OtBu)—OBzl (5)

To a solution of (s)-Fmoc-Asu(OtBu)—OH (50 mg, 107.0 μmol, 1.0 eq.) in DMF was added HOAt (21.8 mg, 0.16 mmol, 1.5 eq.), HATU (61.0 mg, 161.0 μmol, 1.5 eq.) and DIPEA (73.2 μL, 0.48 mmol, 4.5 eq.). After 15 min of stirring at RT, benzyl alcohol (22.2 μL, 0.32 mmol, 3.0 eq.) was further added and the solution stirred overnight. Finally, the solvent was removed in vacuo. Completion of reaction of 5 was analyzed by RP-HPLC (10 to 90% B in 15 min): $t_R$=17.1 min; K'=7.55. Calculated monoisotopic mass for 5 $(C_{34}H_{39}NO_6)$=557.28; found: m/z=580.7 [M+Na]$^+$.

(s)-NHFmoc-Asu-OBzl (6)

tBu deprotection of the crude product 5 was performed with a stirring mixture (v/v) of TFA (95%) and DCM (5%) at RT for 45 min. After evaporation of the solvent, the crude product 6 was purified using preparative RP-HPLC (60 to 80% B in 15 min): $t_R$=9.3 min; K'=8.9. Calculated monoisotopic mass for 6 $(C_{30}H_{31}NO_6)$=501.22; found m/z=524.5 [M+Na]$^+$.

OBzl-(s)-Fmoc-Asu[(OtBu)KuE(OtBu)$_2$] (7)

To a solution of 6 (51.8 mg, 10.3 μmol, 1.0 eq.) in DMF was added HOBt (20.9 mg, 0.15 mmol, 1.5 eq.), TBTU (36.3 mg, 15.5 μmol, 1.5 eq.) and DIPEA (79.4 μL, 59.7 mg, 0.46 mmol, 4.5 eq.). After 15 min stirring, 1 (75.6 mg, 15.5 μmol, 1.5 eq.) was added and further stirred for 20 h at RT. The crude product 7 was purified using preparative RP-HPLC (70 to 80% B in 15 min): $t_R$=8.9 min; K'=1.97. Calculated monoisotopic mass for 7 $(C_{54}H_{74}N_4O_{12})$=970.53; found: m/z=971.8 [M+H]$^+$.

(s)-Fmoc-Asu[(OtBu)KuE(OtBu)$_2$] (8)

For benzyl alcohol (Bzl) deprotection, of 7 (57.2 mg, 65.0 μmol, 1.0 eq.) was dissolved in EtOH (2.0 mL) and palladium on activated charcoal (10%) (5.72 mg, 9.0 μmol, 0.1 eq.) was added. The flask was purged beforehand with hydrogen stream and the solution stirred under light hydrogen-pressure (balloon). After 70 min stirring, the crude product was filtered through celite, the EtOH evaporated in vacuo and the product purified using preparative RP-HPLC (70 to 70.5% B in 15 min): $t_R$=6.5 min; K'=0.54. Calculated monoisotopic mass for 5 $(C_{47}H_{68}N_4O_{12})$=880.48; found: m/z=881.8 [M+H]$^+$.

OPfp-(s)-Fmoc-Asu[(OtBu)KuE(OtBu)$_2$] (9)

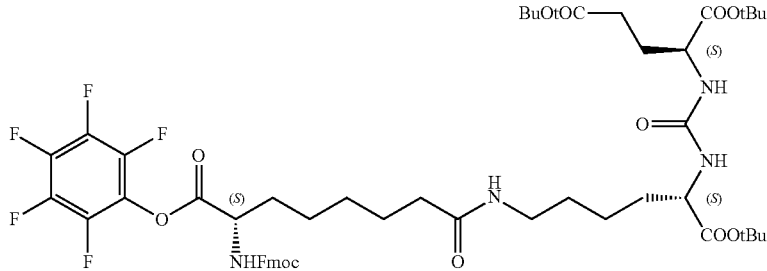

Chemical Formula: C$_{53}$H$_{67}$F$_5$N$_4$O$_{12}$
Molecular Weight: 1047,13

To a solution of 8 (13.6 mg, 15.4 μmol, 1.0 eq.) in dry DMF was added DIC (4.77 μL, 1.94 mg, 30.8 μmol, 2.0 eq.) and PfpOH (5.67 mg, 30.8 μmol, 2.0 eq.). After 5 min stirring, pyridine (2.49 μL, 31.0 μmol, 2.0 eq.) was added and the solution was allowed to stir overnight at RT. Completion of reaction of 9 was analyzed by RP-HPLC (10 to 90% B in 15 min): $t_R$=17.2 min; K'=7.6. Calculated monoisotopic mass for 9 $(C_{53}H_{67}F_5N_4O_{12})$=1046.47; found: m/z=1069.8 [M+Na]$^+$.

NHS-2,4-dinitrobenzoate (NHS-DNBA) (27)

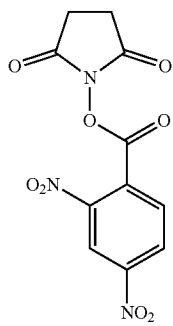

Chemical Formula: $C_{11}H_7N_3O_8$
Molecular Weight: 309,19

To a solution of 2,4-dinitrobenzoic acid (DNBA) (10.0 mg, 47.1 µmol, 1.0 eq.) in dry THF was given N,N'-dicyclohexylcarbodiimide (DCC) (9.7 mg, 47.1 µmol, 1.0 eq.) and N-hydroxysuccinimide (NHS) (10.8 mg, 94.3 µmol, 2.0 eq.) and the reaction mixture was allowed to stir overnight. The crude product was purified using RP-HPLC. RP-HPLC (10 to 90% B in 15 min): $t_R$=10.21 min K'=4.1. Calculated monoisotopic mass $(C_{11}H_7N_3O_8)$=309.02; found: not detectable in ESI-MS

DOTAGA-3-iodo-D-Tyr-D-Phe-D-Lys-OH (DOTAGA-y(3-I)fk) (30)

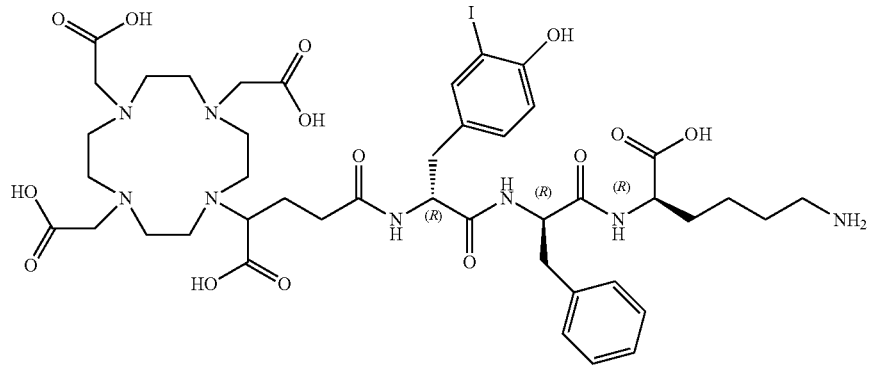

Chemical Formula: $C_{43}H_{61}IN_8O_{14}$
Molecular Weight: 1040,91

The synthesis of 30 was accomplished via solid phase strategy as previously described [2, 3]. In short: The initial starting point was the 2-CTC resin loading according to SP-1 of Fmoc-D-Lys(Boc)-OH. After conjugation of lysine, Fmoc was deprotected according to SP-3 and Fmoc-D-phenylalanine coupled applying SP-2. The same procedure was used to couple Fmoc-D-Tyr(3-I)-OH. After completion of reaction, the Fmoc protecting group was cleaved according to SP-3 and the resin bound peptide condensed with the chelator using DOTAGA-anhydride (2.0 eq.) and DIPEA (2.0 eq.) in DMF. The reaction was allowed to stir for 48 h at RT. Finally, the crude product was cleaved from the resin according to SP-7.2 and precipitated in Et$_2$O and centrifuged. The supernatant was removed and 30 purified using RP-HPLC. RP-HPLC (10 to 90% B in 15 min): $t_R$=6.2 min K'=2.1. Calculated monoisotopic mass $(C_{43}H_{61}IN_8O_{14})$=1,040.34; found: m/z=1,040.5 [M+H]$^+$, m/z=521.3 [M+2H]$^{2+}$, m/z=1,063.4=[M+Na]$^+$.

DOTAGA-y(3-I)fk(L-Asu[KuE]) (PSMA-8)

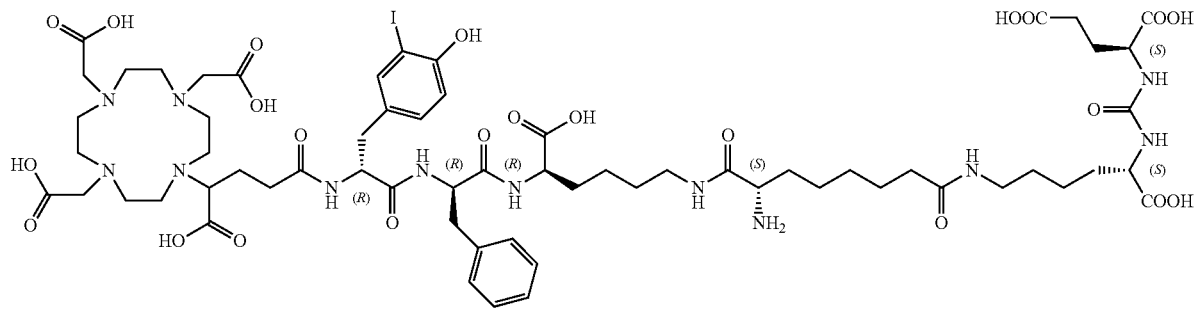

Chemical Formula: $C_{63}H_{93}IN_{12}O_{23}$
Molecular Weight: 1513,40

To a solution of DMF containing 30 (5.0 mg, 4.8 µmol, 1.0 eq.), 9 (7.5 mg, 7.2 µmol, 1.5 eq.) and DIPEA (3.3 µL, 21.6 µmol, 4.0 eq.) were added. The reaction solution was allowed to stir overnight at RT. After completion of reaction, the solvent was removed in vacuo and the crude product treated with a mixture of piperidine in DMF (20/80; v/v) for 15 min to achieve Fmoc-deprotection. The solvent was reduced to approx. 300 µL via evaporation in vacuo, precipitated in $Et_2O$ and centrifuged. With the resulting pellet was processed according to SP-6 for tBu-removal. The final product was purified via RP-HPLC (10 to 90% B in 15 min): $t_R$=6.09 min K'=2.05. Calculated monoisotopic mass $(C_{63}H_{93}IN_{12}O_{23})$=1,512.55; found: m/z=1,513.9 $[M+H]^+$, 757.8 $[M+2H]^{2+}$.

DOTAGA-y(3-I)fk(L-Asu[KuE]-2,4-DNBA) (PSMA-36)

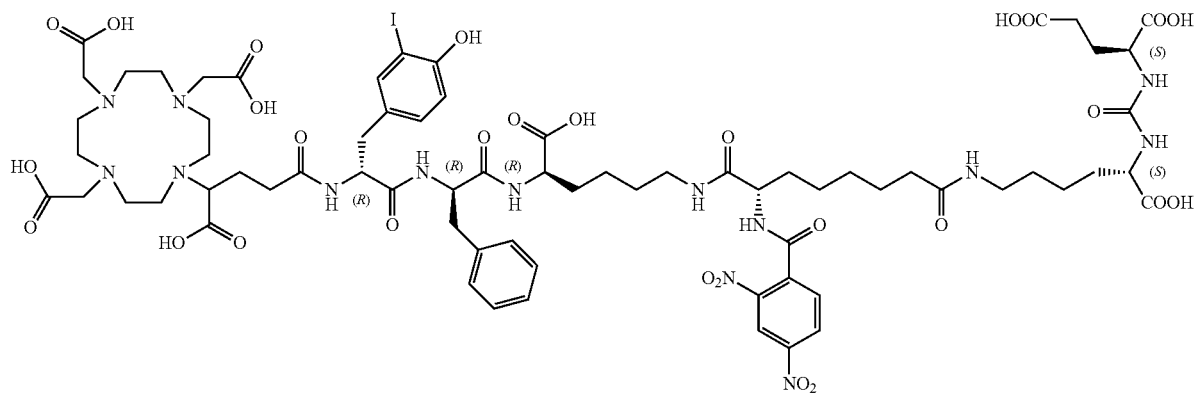

Chemical Formula: $C_{70}H_{95}IN_{14}O_{28}$
Molecular Weight: 1707,50

The synthesis of PSMA-36 was achieved by dissolving PSMA-8 (3.0 mg, 3.3 µmol, 1.0 eq.) in DMF and addition of 27 (4.1 mg, 13.2 µmol, 4.0 eq.) and DIPEA (2.3 µL, 13.2 µmol, 4.0 eq.). The solution was stirred for 10 h at RT and the final product purified by RP-HPLC (10 to 50% B in 15 min): $t_R$=12.12 min K'=5.06. Calculated monoisotopic mass $(C_{70}H_{95}IN_{14}O_{28})$=1,706.55; found: m/z=1,707.8 $[M+H]^+$, 854.7 $[M+2H]^{2+}$.

[$^{nat}$Lu]DOTAGA-y(3-I)fk(L-Asu[KuE]-2,4-DNBA) ([$^{nat}$Lu]PSMA-36)

RP-HPLC (10 to 60% B in 15 min): $t_R$=9.81 min K'=3.91. Calculated monoisotopic mass $(C_{70}H_{92}IN_{14}O_{28}Lu)$=1,878.47; found: m/z=1,879.9 $[M+H]^+$.

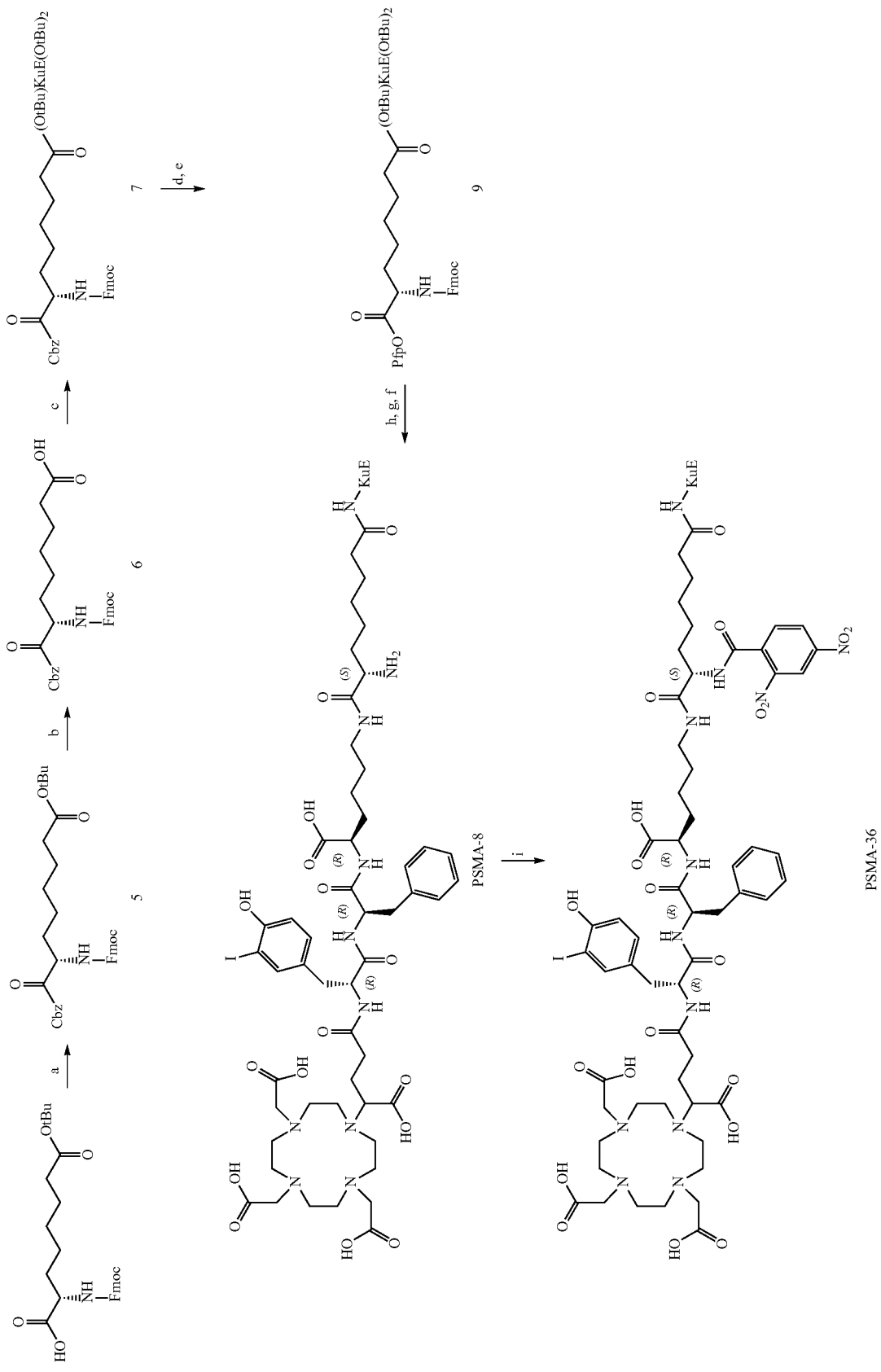

Schematic illustration of the synthesis of PSMA-36. (a) HOAt, HATU, DIPEA, benzyl-alcohol, [DMF]; (b) 95% TFA, 5% DCM; (c) 1, HOBt, TBTU, DIPEA, [DMF]; (d) Pd/C (10%), H₂, [EtOH]; (e) DIC, PFP, pyridine, [DMF]; (f) 30, DIPEA, [DMF]; (g) 20% piperidine in DMF, [DMF]; (h) TFA; (i) 27, DIPEA [DMF].

4. Synthesis of EuE-Based PSMA Inhibitors PSMA-52 and PSMA-53

DOTAGA-F(4-NO$_2$)-y-2-nal-k(Suc-N$^5$-orn-C$^4$-EuE) (PSMA-52)

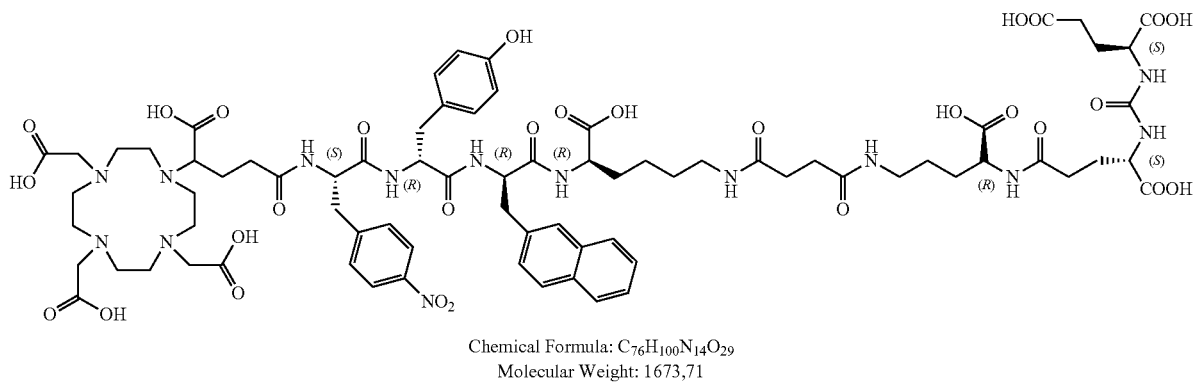

Chemical Formula: C$_{76}$H$_{100}$N$_{14}$O$_{29}$
Molecular Weight: 1673,71

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with succinic anhydride (4.0 eq.) and DIPEA (1.5 eq.) dissolved in DMF. The reaction mixture was allowed to react overnight at RT. Next, Fmoc-D-Lys-OtBu.HCl (1.5 eq.) was coupled according to SP-2 and Fmoc-deprotected as described in SP-3. The following conjugations with the Fmoc-protected amino acids Fmoc-D-2-Nal-OH, Fmoc-D-Tyr(OtBu)—OH and Fmoc-L-Phe(4-NO$_2$)—OH were conducted as described in SP-2. The N-terminal Fmoc-deprotected amino acid was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in Et$_2$O, centrifuged and the supernatant removed. The final product was purified via RP-HPLC. RP-HPLC (10 to 60% B in 15 min): t$_R$=9.71 min K'=3.86. Calculated monoisotopic mass (C$_{76}$H$_{100}$N$_{14}$O$_{29}$)=1,672.68; found: m/z=1,673.0 [M+H]$^+$.

[$^{nat}$Lu]DOTAGA-F(4-NO$_2$)-y-2-nal-k(Suc-N$^5$-orn-C$^4$-EuE) ([$^{nat}$Lu]PSMA-52)

RP-HPLC (10 to 60% B in 15 min): t$_R$=9.4 min K'=3.7. Calculated monoisotopic mass (C$_{76}$H$_{97}$N$_{14}$O$_{29}$Lu)=1,844.6; found: m/z=1,846.0 [M+H]$^+$.

2,4-DNBA-Dap(DOTAGA)-y-2-nal-k(Suc-N$^5$-orn-C$^4$-EuE) (PSMA-53)

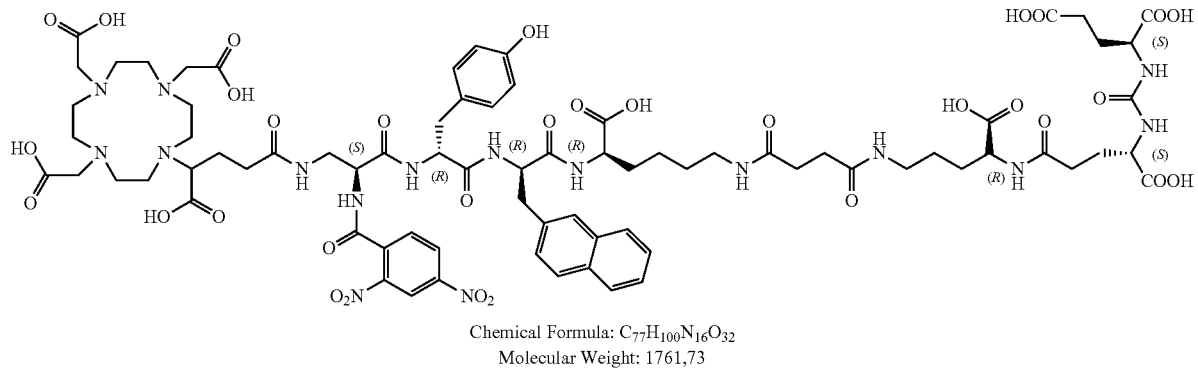

Chemical Formula: C$_{77}$H$_{100}$N$_{16}$O$_{32}$
Molecular Weight: 1761,73

The initial resin loading with Fmoc-D-Orn(NHDde)-OH was performed as described in SP-1. After Fmoc-deprotection according to SP-3, 2 (1.5 eq.) was coupled to D-Orn(NHDde) according to SP-2. In the next step, the Dde-protecting group was cleaved according to SP-4 and the free amino group treated with succinic anhydride (4.0 eq.) and DIPEA (1.5 eq.) dissolved in DMF. The reaction mixture was allowed to react overnight at RT. Next, Fmoc-D-Lys-OtBu-HCl (1.5 eq.) was coupled according to SP-2 and Fmoc-deprotected as described in SP-3. The following conjugations with the Fmoc-protected amino acids Fmoc-D-2-Nal-OH, Fmoc-D-Tyr(OtBu)—OH and of Fmoc-L-Dap(NHDde)-OH were conducted as described in SP-2. After coupling of Fmoc-L-Dap(NHDde)-OH, Fmoc-deprotection was achieved as described in SP-3. Next, the free amino group was conjugated to 2,4-dintrobenzoic acid (2,4-DNBA) using 2,4-DNBA (2.0 eq.), HOBt (2.0 eq.), TBTU (2.0 eq.) and DIPEA (4.0 eq.) in DMF. After completion of reaction, Dde-deprotection was achieved using SP-5. The N-terminal free amino acid L-Dap was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in $Et_2O$, centrifuged and the supernatant removed. The final product was purified via RP-HPLC.

RP-HPLC (10 to 60% B in 15 min): $t_R$=11.71 min K'=4.86. Calculated monoisotopic mass ($C_{77}H_{100}N_{16}O_{32}$)= 1,760.67; found: m/z=1,762.1 $[M+H]^+$.

[$^{nat}$Lu]2,4-DNBA-Dap(DOTAGA)-y-2-nal-k(Suc-$N^5$-orn-$C^4$-EuE) ([$^{nat}$Lu]PSMA-53)

RP-HPLC (10 to 60% B in 15 min): $t_R$=8.3 min K'=3.15. Calculated monoisotopic mass ($C_{77}H_{97}N_{16}O_{32}Lu$)=1,932.59; found: m/z=1,933.7 $[M+H]^+$.

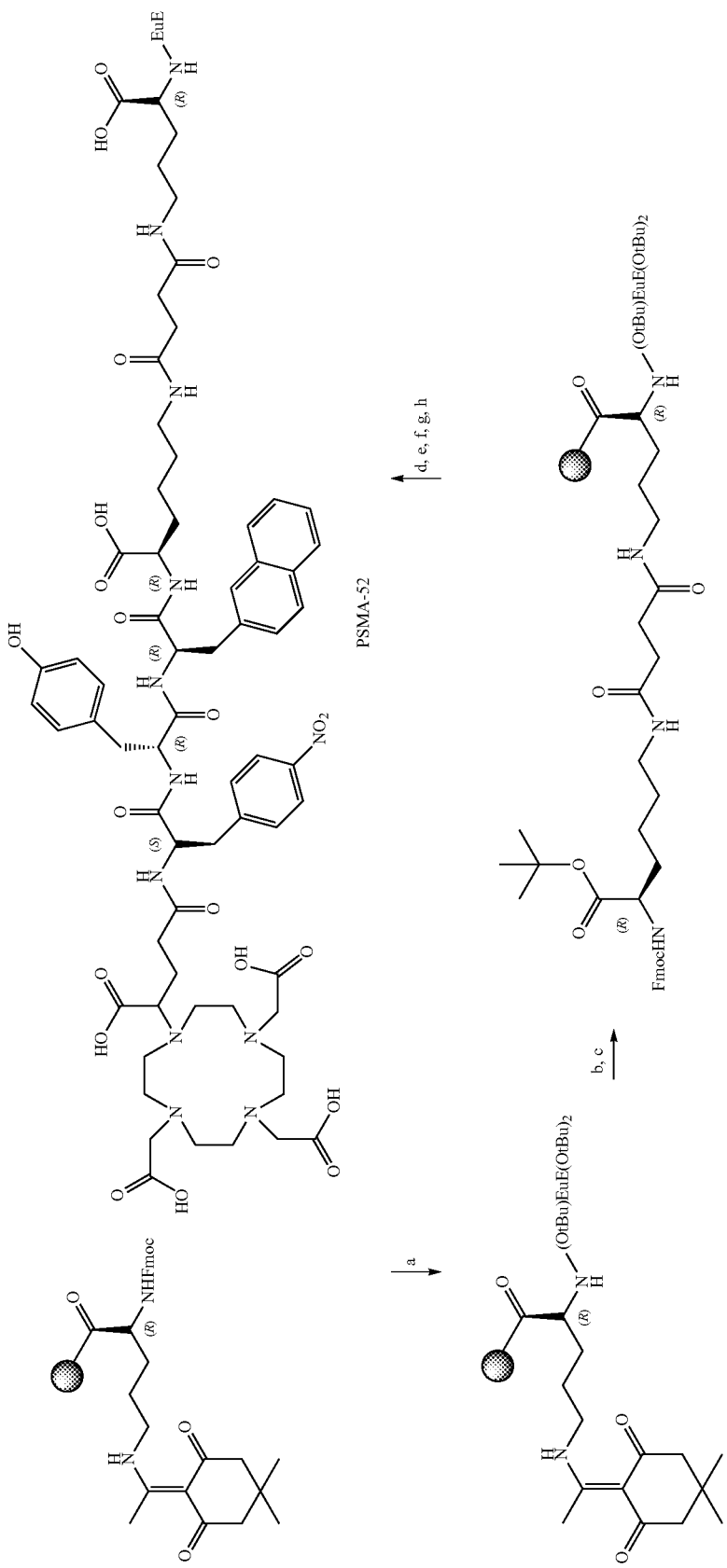

Schematic illustration of the gerenal synthesis procedure of EuE-based PSMA inhibitors PSMA-52 and PSMA-53 exemplified by PSMA-52. (a) 20% piperidine in DMF, 2, HOBt, TBTU, DIPEA [DMF]; (b) succinic anhydride, DIPEA [DMF]; (c) Fmoc—D/L-Lys-OAll·HCl, HOBt, TBTU, DIPEA [DMF]; (d) 20% piperidine in DMF, Fmoc—D-2-Nal—OH, HOBt, TBTU, DIPEA [DMF]; (e) 20% piperidine in DMF, Fmoc---D-Tyr(OBu)—OH, HOBt, TBTU, DIPEA [DMF]; (f) 20% piperidine in DMF, Fmoc—D-Phe(4-NH$_2$)—OH, HOBt, TBTU, DIPEA [DMF]; (g) DOTAGA-anhydride, DIPEA [DMF]; (h) TFA;

5. Synthesis of PSMA-61 and PSMA-62

DOTAGA-F(4-NH$_2$)y-2-nal-k(d[N$^5$-orn-C$^4$-EuE]-2,4-DNBA) (PSMA-61)

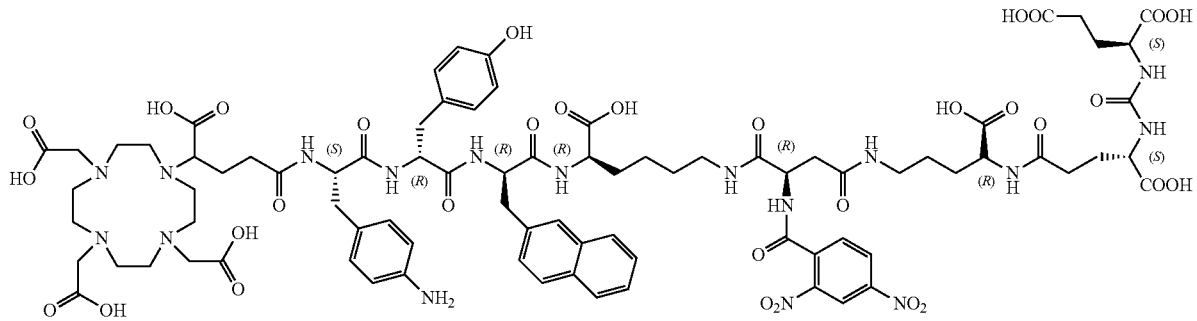

Chemical Formula: C$_{83}$H$_{105}$N$_{17}$O$_{32}$
Molecular Weight: 1852,84

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with Fmoc-D-Asp-OAII.HCl (1.5 eq.) according to SP-2. The amino group of Fmoc-D-Asp-OAII.HCl was deprotected according to SP-3 and conjugated to 2,4-DNBA using 2,4-DNBA (1.5 eq.), HOBt (2.0 eq.), TBTU (2.0 eq.) and DIPEA (4.0 eq.) in DMF. After completion of reaction, Allyl-deprotection was achieved according to SP-5. The next steps included the repetitive conjugation with Fmoc-D-Lys-OtBu.HCl (1.5 eq.), Fmoc-D-2-Nal-OH, Fmoc-D-Tyr(OtBu)—OH and Fmoc-L-Phe(4-NHBoc)-OH according to SP-2. The N-terminal Fmoc-deprotected amino acid L-Phe(4-NHBoc)-OH was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in Et$_2$O, centrifuged and the supernatant removed. The final product was purified via RP-HPLC.

RP-HPLC (10 to 90% B in 15 min): t$_R$=6.40 min K'=2.2. Calculated monoisotopic mass (C$_{83}$H$_{105}$N$_{17}$O$_{32}$)=1,851.71; found: m/z=1,852.5 [M+H]$^+$, 926.7 [M+2H]$^{2+}$.

[$^{nat}$Lu]DOTAGA-F(4-NH$_2$)y-2-nal-k(d[N$^5$-orn-C$^4$-EuE]-2,4-DNBA) ([$^{nat}$Lu]PSMA-61)

RP-HPLC (10 to 90% B in 15 min): t$_R$=8.22 min K'=3.11. Calculated monoisotopic mass (C$_{83}$H$_{102}$N$_{17}$O$_{32}$Lu)=2,023.63; found: m/z=1,013.1 [M+2H]$^{2+}$.

DOTAGA-F(4-NH$_2$)y-2-nal-k(d[N$^5$-orn-C$^4$-EuE]-TMA) (PSMA-62)

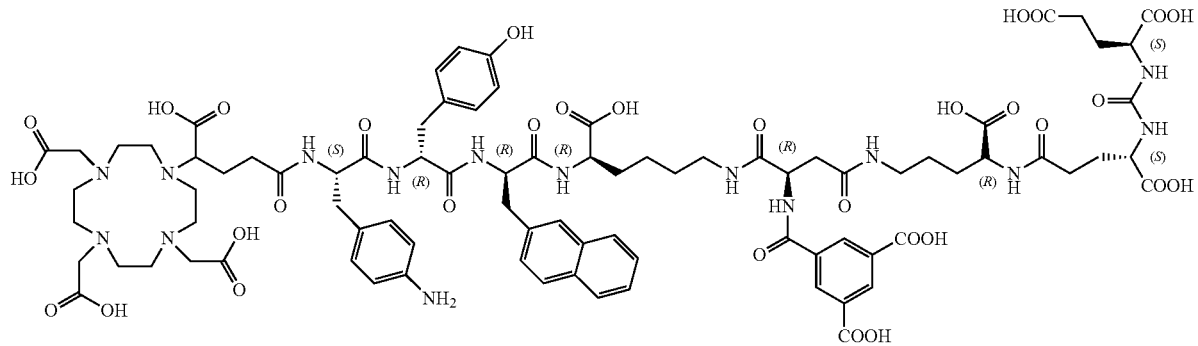

Chemical Formula: C$_{85}$H$_{107}$N$_{15}$O$_{32}$
Molecular Weight: 1850,86

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with Fmoc-D-Asp-OAII.HCl (1.5 eq.) according to SP-2. The amino group of Fmoc-D-Asp-OAII.HCl was Fmoc-deprotected according to SP-3 and protected with Dde-OH (2.0 eq.) and DIPEA (4.0 eq.) in DMF at RT. The reaction was allowed to stir overnight. Afterwards, Allyl-deprotection of D-Asp was achieved applying SP-5. The next steps included the repetitive conjugation with Fmoc-D-Lys-OtBu.HCl (1.5 eq.), Fmoc-D-2-Nal-OH, Fmoc-D-Tyr(OtBu)—OH and Fmoc-L-Phe(4-NH-Boc)-OH according to SP-2. In order to conjugate TMA to D-Asp, selective Dde-deprotection was achieved applying SP-4 to afford the free amino group. TMA was coupled using TMA (2.0 eq.), HOBt (1.5 eq.), TBTU (1.5 eq.) and DIPEA (10 eq.) in DMF. The reaction was allowed to stir for 8 h at RT. After conjugation of TMA, Fmoc-deprotection of Fmoc-L-Phe(4-NHBoc)-OH was achieved using SP-3. The N-terminal Fmoc-deprotected amino acid L-Phe(4-NHBoc)-OH was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in Et$_2$O, centrifuged and the supernatant removed. The final product was purified via RP-HPLC. RP-HPLC (10 to 70% B in 15 min): $t_R$=7.48 min K'=2.74. Calculated monoisotopic mass $(C_{85}H_{107}N_{15}O_{32})$=1,849.72; found: m/z=1,850.5 [M+H]$^+$, 925.7 [M+2H]$^{2+}$.

[$^{nat}$Lu] DOTAGA-F(4-N H$_2$)y-2-nal-k(d[N$^5$-orn-C$^4$-EuE]-TMA) ([$^{nat}$Lu]PSMA-62)

RP-HPLC (10 to 70% B in 15 min): $t_R$=7.27 min K'=2.64. Calculated monoisotopic mass $(C_{85}H_{104}N_{15}O_{32}Lu)$=2,021.64; found: m/z=1,012.3 [M+2H]$^{2+}$.

6. Synthesis of PSMA-65, PSMA-66 and PSMA-71

2,4-DNBA-Dap(DOTAGA)y-2-nal-e(Abz-N$^5$-orn-C$^4$-EuE) (PSMA-65)

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with Fmoc-4-Abz-OH (1.5 eq.), HOAt (1.5 eq.), HATU (1.5 eq.) and DIPEA (4.0 eq.) in DMF. The reaction was allowed to stir overnight at RT. In the next step, the Abz-residue was Fmoc-deprotected according to SP-3. The next steps included the repetitive conjugation with Fmoc-D-Glu-OtBu, Fmoc-D-2-Nal-OH, Fmoc-D-Tyr (OtBu)—OH and Fmoc-L-Dap(Dde)-OH according to SP-2. After Fmoc-deprotection of Fmoc-L-Dap(Dde)-OH according to SP-3, 2,4-DNBA was coupled using 2,4-DNBA (1.5 eq.), HOBt (2.0 eq.), TBTU (2.0 eq.) and DIPEA (4.0 eq.) in DMF. After completion of reaction, the L-Dap(Dde)-residue was Dde-deprotected according to SP-4 and conjugated to the chelator using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in Et$_2$O, centrifuged and the supernatant removed. The final product was purified via RP-HPLC. RP-HPLC (10 to 60% B in 15 min): $t_R$=10.2 min K'=4.1. Calculated monoisotopic mass $(C_{79}H_{96}N_{16}O_{32})$=1,780.64; found: m/z=1,781.3 [M+H]$^+$.

[$^{nat}$Lu]2,4-DNBA-Dap(DOTAGA)y-2-nal-e(Abz-N$^5$-orn-C$^4$-EuE) ([$^{nat}$Lu]PSMA-65)

RP-HPLC (10 to 60% B in 15 min): $t_R$=9.8 min K'=3.9. Calculated monoisotopic mass $(C_{79}H_{93}N_{16}O_{32}Lu)$=1,952.56; found: m/z=1,954.0 [M+H]$^+$.

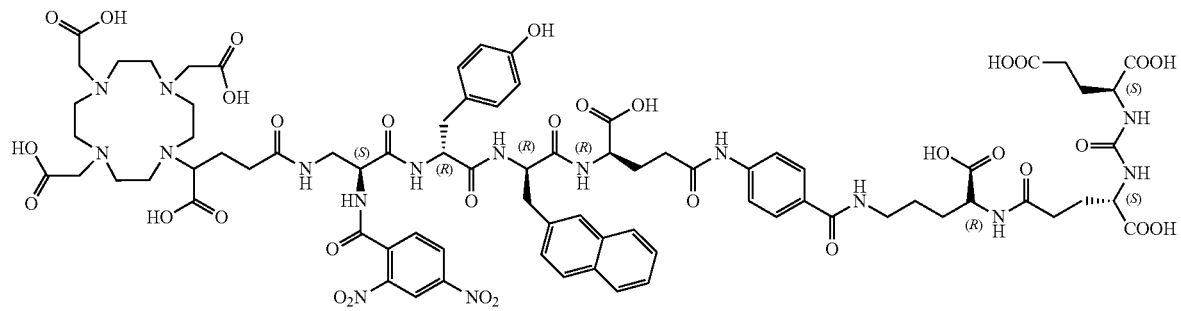

Chemical Formula: $C_{79}H_{96}N_{16}O_{32}$
Molecular Weight: 1781,72

DOTAGA-Dap(TMA)y-2-nal-k(d[N⁵-orn-C⁴-EuE]-TMA) (PSMA-66)

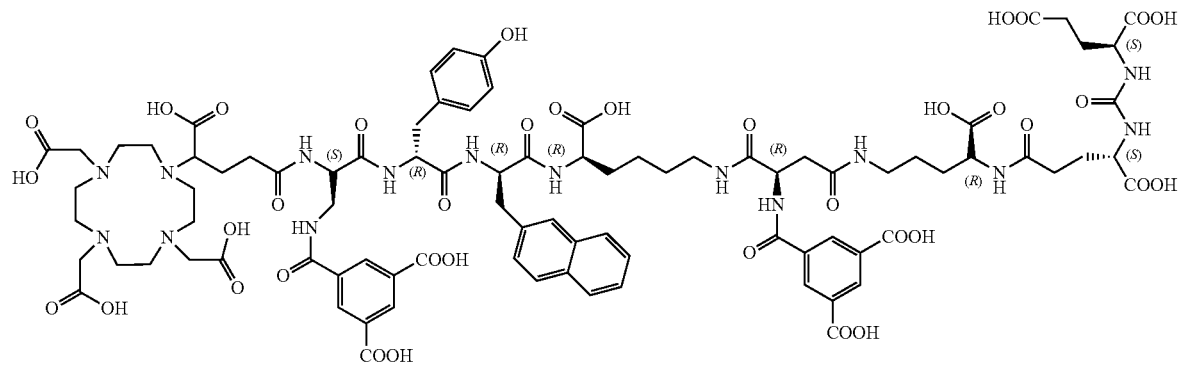

Chemical Formula: $C_{88}H_{107}N_{15}O_{37}$
Molecular Weight: 1966,89

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with Fmoc-D-Asp-OAll.HCl (1.5 eq.) according to SP-2. The amino group of Fmoc-D-Asp-OAll.HCl was Fmoc-deprotected according to SP-3 and protected with 2.0 eq. Dde-OH and 4.0 eq. DIPEA in DMF. The reaction was allowed to stir overnight. Afterwards, Allyl-deprotection of D-Asp was achieved applying SP-5. The next steps included the repetitive conjugation with Fmoc-D-Lys-OtBu-HCl (1.5 eq.), Fmoc-D-2-Nal-OH, Fmoc-D-Tyr(OtBu)—OH and Fmoc-L-Dap(Dde)-OH according to SP-2. In order to conjugate TMA to D-Asp and L-Dap, selective Dde-deprotection was achieved applying SP-4 to afford the free amino groups. TMA was coupled using TMA (4.0 eq.), HOBt (3.0 eq.), TBTU (3.0 eq.) and DIPEA (20 eq.) in DMF. The reaction was allowed to stir for 8 h at RT. After conjugation of TMA, Fmoc-deprotection of Fmoc-L-Dap(TMA)-OH was achieved using SP-3. The N-terminal Fmoc-deprotected amino acid L-Dap was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in Et₂O, centrifuged and the supernatant removed. The final product was purified via RP-HPLC. RP-HPLC (10 to 70% B in 15 min): $t_R$=7.48 min K'=2.74. Calculated monoisotopic mass ($C_{88}H_{107}N_{15}O_{37}$)=1,965.70; found: m/z=1,966.4 [M+H]⁺, 984.1 [M+2H]²⁺.

[$^{nat}$Lu]DOTAGA-Dap(TMA)y-2-nal-k(d[N⁵-orn-C⁴-EuE]-TMA) (PSMA-66)

RP-HPLC (10 to 70% B in 15 min): $t_R$=7.46 min K'=2.73. Calculated monoisotopic mass ($C_{88}H_{108}N_{15}O_{37}$Lu)=2,137.62; found: m/z=1,070.4 [M+2H]²⁺.

DOTAGA-2-Nal-y-2-nal-k(d[N⁵-orn-C⁴-EuE]-TMA) (PSMA-71)

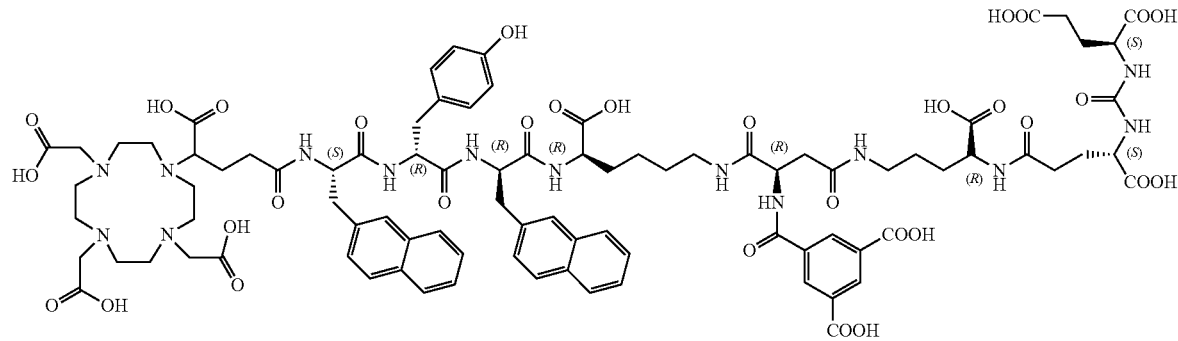

The initial resin loading with Fmoc-D-Orn(NHDde)-OH was performed as described in SP-1. After Fmoc-deprotection according to SP-3, 2 (1.5 eq.) was coupled to D-Orn (NHDde) according to SP-2. In the next step, the Dde-protecting group was cleaved according to SP-4 and the free amino group treated with Fmoc-D-Asp-OAII.HCl (1.5 eq.) according to SP-2. The amino group of Fmoc-D-Asp-OAII.HCl was Fmoc-deprotected according to SP-3 and protected with Dde-OH (2.0 eq.) and DIPEA (4.0 eq.) in DMF at RT. The reaction was allowed to stir overnight. Afterwards, Allyl-deprotection of D-Asp was achieved applying SP-5. The next steps included the repetitive conjugation with Fmoc-D-Lys-OtBu-HCl (1.5 eq.), Fmoc-D-2-Nal-OH, Fmoc-D-Tyr(OtBu)—OH and Fmoc-L-2-Nal-OH according to SP-2. In order to conjugate TMA to D-Asp, selective Dde-deprotection was achieved applying SP-4 to afford the free amino group. TMA was coupled using TMA (2.0 eq.), HOBt (1.5 eq.), TBTU (1.5 eq.) and DIPEA (10 eq.) in DMF. The reaction was allowed to stir for 8 h at RT. After conjugation of TMA, Fmoc-deprotection of Fmoc-L-2-Nal-OH was achieved using SP-3. The N-terminal Fmoc-deprotected amino acid L-2-Nal-OH was conjugated with the chelator in the final step using DOTAGA-anhydride (2.0 eq.) and DIPEA (2.0 eq.). The reaction was allowed to stir for 48 h at RT. After completion of reaction with DOTAGA-anhydride, the peptide was cleaved from the resin according to SP-7.2, the crude product precipitated in $Et_2O$, centrifuged and the supernatant removed. The final product was purified via RP-HPLC. RP-HPLC (10 to 80% B in 15 min): $t_R$=7.57 min K'=2.79. Calculated monoisotopic mass $(C_{89}H_{108}N_{14}O_{32})$=1,884.73; found: m/z=1,886.1 $[M+H]^+$, 943.5 $[M+2H]^{2+}$.

[$^{nat}$Lu]DOTAGA-2-Nal-y-2-nal-k(d[$N^5$-orn-C4-EuE]-TMA) ([$^{nat}$Lu]PSMA-67)

RP-HPLC (10 to 90% B in 15 min): $t_R$=7.81 min K'=2.91. Calculated monoisotopic mass $(C_{89}H_{105}N_{14}O_{32}Lu)$=2,056.64; found: m/z=1,029.7 $[M+2H]^{2+}$.

7. Radiolabeling $^{68}$Ga-labeling:
The $^{68}$Ge/$^{68}$Ga generator was eluted with aq. HCl (1.0 M), from which a fraction of 1.25 mL, containing approximately 80% of the activity (600 to 800 MBq), was transferred into a reaction vial (ALLTECH, 5 mL). The vial was beforehand loaded with the respective compound (5.0 nmol) and an aq. 2-(4-(2-hydroxyethyl)-1-piperazinyl)-ethanesulfonic acid (HEPES) solution (950 µL, 2.7 M). The reaction vial was heated for 5 min at 95° C. with subsequent fixation of the radiolabeled compound on a preconditioned SPE cartridge (C8 light, SepPak). After purging the cartridge with water (10 mL) in advance, the elution of the radiolabeled PSMA inhibitor from the cartridge was achieved with a mixture of EtOH and water (1/1; v/v), phosphate buffered saline (PBS) (1.0 mL) and again water (1.0 mL). At the end of radiolabeling, the EtOH was evaporated in vacuo and the tracer used without any further purification. Radiochemical purity was controlled using Radio-TLC (1.0 M sodium citrate buffer and 0.06 M $NH_4OAc$/MeOH buffer (1/1; v/v)).

$^{177}$Lu-labeling:
The $^{177}$Lu-labeled compounds were prepared as previously described [5] with minor modifications and used without further purification. In short, to $NH_4OAc$-buffer (10 µL, 1.0 M, pH=5.9) was added the respective tracer (0.75 to 1.0 nmol, 7.5 to 10 µL), $^{177}LuCl_3$ (10 to 40 MBq; $A_S$>3000 GBq/mg, 740 MBq/mL, 0.04 M HCl, ITG, Garching, Germany) and finally filled with trace-pure water (up to 100 µL) (Merck, Darmstadt, Germany). The reaction mixture was heated for 40 min at 95° C. and the radiochemical purity was determined using radio-TLC.

$^{125}$I-Labeling:
Briefly, the stannylated precursor $(SnBu_3$-BA)(OtBu)KuE $(OtBu)_2$ (PSMA-45) (approx. 0.1 mg) was dissolved in a solution containing peracetic acid (20 µL), [$^{125}$I]NaI (5.0 µL, approx. 21.0 MBq) (74 TBq/mmol, 3.1 GBq/mL, 40 mM NaOH, Hartmann Analytic, Braunschweig, Germany), MeCN (20 µL) and AcOH (10 µL). The reaction solution was incubated for 10 min at RT, loaded on a cartridge (C18 Sep Pak Plus, preconditioned with 10 mL MeOH and 10 mL water) and rinsed with water (10 mL). After elution with a 1/1 mix (v/v) of EtOH and MeCN (2.0 mL), the solution was evaporated to dryness under a gentle nitrogen stream and treated with TFA (200 µL) for 30 min with subsequent evaporation of TFA. The crude product of ([$^{125}$I]I-BA)KuE was purified by radio-RP-HPLC (20 to 40% B in 20 min): $t_R$=13.0 min; K'=6.2.

8. Determination of HSA Binding

HSA binding experiments were performed as previously described [6]. The mobile phase consisted of a binary gradient system with a constant total flow rate of 0.5 mL/min. Mobile phase A was a 50 mm pH 6.9 $NH_4OAc$-solution, mobile phase B was 2-Propanol (RP-HPLC grade, VWR, Germany). The gradient of mobile phase A was 100% from 0 to 3 min and from 3 min to the end of each run mobile phase B was set 20%. At each experimental day, the column was calibrated with nine reference substances to confirm the performance and to establish the non-linear regression. PSMA inhibitors were dissolved in a 0.5 mg/mL concentration in a mixture of 2-Propanol and $NH_4OAc$-buffer (50 mm pH 6.9) (1/1; v/v). For each run, 10 µL of the solution containing the inhibitor was injected into the RP-HPLC system and the retention time measured. The literature HSA binding [%] was obtained from Valko et. al. or Yamazaki et al. [6, 7]. Non-linear regression was established with OriginPro 2016G.

9. Determination of Lipophilicity

Lipophilicity:
The radiolabeled PSMA inhibitor (0.5 to 1.0 MBq) dissolved in PBS (500 µL, pH=7.4), was added to n-octanol (500 µL) in a reaction vial (1.5 mL), which was rigorously vortexed for 3 min (n=6). For quantitative phase separation, the mixture was centrifuged at 6,000 g for 5 min (Biofuge 15, Heraus Sepatech, Osterode, Germany). The activity from samples of each phase (100 µL) were measured in a γ-counter to obtain the log $P_{(o/w)}$ value.

10. Cell Experiments

Cell Culture:
PSMA-positive LNCAP cells (300265; Cell Lines Service GmbH) were cultivated in Dulbecco modified Eagle medium/Nutrition Mixture F-12 (1/1) (DMEM-F12, Biochrom) supplemented with fetal calf serum (FCS) (10%, Biochrom) and kept at 37° C. in a humidified $CO_2$ atmosphere (5%). One day (24 h±2 h) prior to all experiments with LNCaP cells, the cultivated cells were harvested using a mixture of trypsin/ethylendiaminetetraacetate (0.05%/0.02%) and PBS and centrifuged. After centrifugation, the supernatant was disposed and the cell pellet resuspended in culture medium. Afterwards, cells were counted with a hemocytometer (Neubauer) and seeded in 24-well plates. $IC_{50}$ values were determined transferring 150,000 cells/mL per well into 24-well plates, whereas internalization rates were obtained by transferring 125,000 cells/mL per well into 24-well PLL-coated plates.

11. Affinity ($IC_{50}$)

After removal of the culture medium, the cells were treated once with HBSS (500 μL, Hank's balanced salt solution, Biochrom, Berlin, Germany, with addition of 1% BSA) and left 15 min on ice for equilibration in HBSS (200 μL, 1% BSA). Next, solutions (25 μL per well) containing either HBSS (1% BSA, control) or the respective ligand in increasing concentration ($10^{-10}$ to $10^{-4}$ m in HBSS (1% BSA)) were added with subsequent addition of ($[^{125}I]$I-BA) KuE (25 μL, 2.0 nm) in HBSS (1% BSA). All experiments were performed at least three times for each concentration. After 60 min incubation on ice, the experiment was terminated by removal of the medium and consecutive rinsing with HBSS (200 μL). The media of both steps were combined in one fraction and represent the amount of free radioligand. Afterwards, the cells were lysed with NaOH (250 μL, 1.0 m) and united with the HBSS (200 μL) of the following washing step. Quantification of bound and free radioligand was accomplished in a γ-counter.

12. Internalization

Subsequent to the removal of the culture medium, the cells were washed once with DMEM-F12-solution (500 μL, 5% BSA) and left to equilibrate for at least 15 min at 37° C. in DMEM-F12-solution (200 μL, 5% BSA). Afterwards, each well was treated with either DMEM-F12-solution (25 μL, 5% BSA) or 2-PMPA-solution (25 μL, 100 μm) for blockade. Next, the respective $^{68}$Ga- or $^{177}$Lu-labeled PSMA inhibitor (25 μL; 2.0 nm and 10 nm, respectively) was added and the cells incubated at 37° C. for 5, 15, 30 and 60 min, respectively. The experiment was terminated by placing the 24-well plate on ice for 3 min and the consecutive removal of the medium. Each well was rinsed with HBSS (250 μL) and the fractions from these first two steps combined, representing the amount of free radioligand. Removal of surface bound activity was accomplished by incubation of the cells with ice-cold 2-PMPA-solution (250 μL, 10 μm in PBS) for 5 min and subsequent rinsing with ice-cold PBS (250 μL). The internalized activity was determined through incubation of the cells in NaOH (250 μL, 1.0 m) and the combination with the fraction of the subsequent washing step with again NaOH (250 μL, 1.0 m). Each experiment (control and blockade) was performed in triplicate for each time point. Free, surface bound and internalized activity was quantified in a γ-counter.

13. Externalization

Externalization kinetics of the radiolabeled PSMA inhibitors were determined using LNCaP cells, which were similarly prepared as described for the internalization assay. After an initial cell-washing step with DMEM-F12-solution (5% BSA), the cells were left to recondition for at least 15 min at 37° C. Subsequently, the LNCaP cells were incubated with the respective radiolabeled peptide (25 μL, 10.0 nm) at 37° C. for 60 min in a total volume of 250 μL in each well. After 60 min, the supernatant with the unbound free fraction was removed and measured in a γ-counter for the calculation of total added radioactivity. An acid wash step was avoided to warrant enzyme integrity during the following externalization and recycling study. To determine the recycling rate, fresh DMEM-F12-solution (250 μL, 5% BSA) was given to the cells to allow re-internalization. In contrast, re-internalization was inhibited by addition of DMEM-F12-solution containing 2-PMPA (225 μL DMEM-F12 (5% BSA) and 25 μL of 100 μm 2-PMPA-solution (PBS)). The cells were then incubated for 0, 20, 40 and 60 min at 37° C. Consequently, the supernatant was removed and the cells were washed with ice-cold HBSS (250 μL). The combination of the supernatant and the volume of the concomitant washing step with HBSS (200 μL) account for externalized radioligand at the investigated time point. Further, the cells were then washed with ice-cold 2-PMPA HBSS solution (250 μL, 10 μm) twice, combined and thus represented the fraction of membrane-bound radioligand. The determination of the internalized fraction was achieved by lysis as described for the internalization assay with NaOH (250 μL, 1.0 m). The activities of free, externalized, membrane-bound and internalized radioligand were quantified in a γ-counter.

14. Animal Experiments

All animal experiments were carried out in accordance with the general animal welfare regulations in Germany (Deutsches Tierschutzgesetz, approval #55.2-1-54-2532-71-13). For the tumor model, LNCaP cells (approx. $10^7$ cells) were suspended in serum-free DMEM-F12 medium and Matrigel (1/1; v/v) (BD Biosciences, Germany) and inoculated onto the right shoulder of male, 6 to 8 weeks old CB-17 SCID mice (Charles River Laboratories, Sulzfeld, Germany). Animals were used after the tumor size reached 4 to 8 mm in diameter for experiments.

15. PET

Imaging experiments were conducted using a Siemens Inveon small animal PET and the data analyzed by the associated Inveon Research Workplace software. Mice were anaesthetized with isoflurane and approx. 4.0 to 17 MBq of the $^{68}$Ga-labeled compounds were injected via tail vein (approx. 150 to 300 μL). Dynamic imaging was carried out after on-bed injection for 90 min. The static blockade image was obtained after 1 h p.i. with 15 min acquisition time. PSMA-blockade was achieved by coinjection of 8 mg/kg of 2-PMPA-solution (PBS). All images were reconstructed using an OSEM3D algorithm without scanner and attenuation correction.

16. Biodistribution

Approximately 4.0 to 12.0 MBq (approx. 150 to 300 μL) of the respective $^{68}$Ga- or $^{177}$Lu-labeled PSMA inhibitors were injected into the tail vein of LNCaP tumor-bearing male CB-17 SCID mice, which were sacrificed after a specific timeframe (n=4, respectively). Selected organs were removed, weighted and measured in a γ-counter.

17. References in Example 1

1. Šimeček, J., et al., *A Monoreactive Bifunctional Triazacyclononane Phosphinate Chelator with High Selectivity for Gallium-68*. ChemMedChem, 2012. 7(8): p. 1375-1378.

2. Weineisen, M., et al., *Development and first in human evaluation of PSMA I&T-A ligand for diagnostic imaging and endoradiotherapy of prostate cancer*. Journal of Nuclear Medicine, 2014. 55(supplement 1): p. 1083-1083.
3. Weineisen, M., et al., *Synthesis and preclinical evaluation of DOTAGA-conjugated PSMA ligands for functional imaging and endoradiotherapy of prostate cancer*. EJNMMI research, 2014. 4(1): p. 1.
4. Weineisen, M., et al., *68Ga-and 177Lu-Labeled PSMA I&T: Optimization of a PSMA-Targeted Theranostic Concept and First Proof-of-Concept Human Studies*. Journal of Nuclear Medicine, 2015. 56(8): p. 1169-1176.
5. Sosabowski, J. K. and S. J. Mather, *Conjugation of DOTA-like chelating agents to peptides and radiolabeling with trivalent metallic isotopes*. Nat. Protocols, 2006. 1(2): p. 972-976.
6. Valko, K., et al., *Fast gradient HPLC method to determine compounds binding to human serum albumin. Relationships with octanol/water and immobilized artificial membrane lipophilicity*. Journal of pharmaceutical sciences, 2003. 92(11): p. 2236-2248.
7. Yamazaki, K. and M. Kanaoka, *Computational prediction of the plasma protein-binding percent of diverse pharmaceutical compounds*. Journal of pharmaceutical sciences, 2004. 93(6): p. 1480-1494.

EXAMPLE 2: Results

1. Effect of the Introduction of 2,4-Dinitrobenzoic Acid into the Linker Area of PSMA I&T DOTAGA-y(3-I)fk(Sub-KuE) (PSMA I&T)

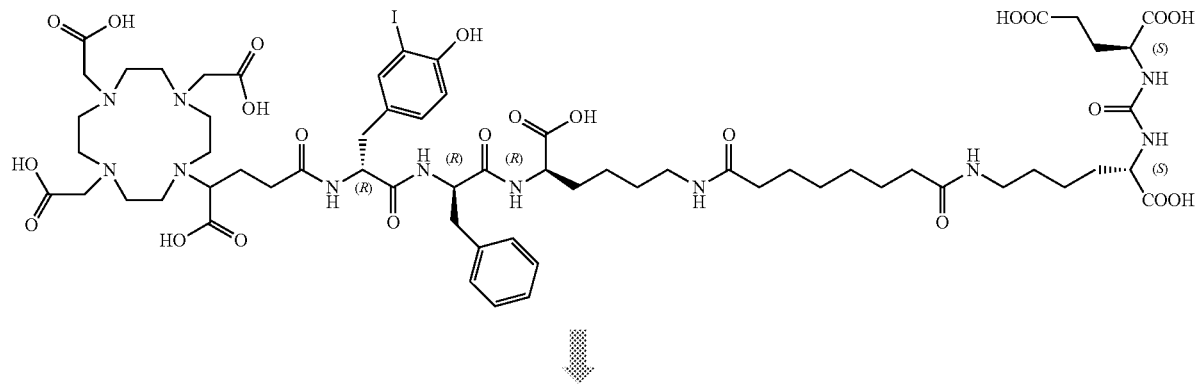

DOTAGA-y(3-I)fk(L-Asu[KuE]-2,4-DNBA) (PSMA-36)

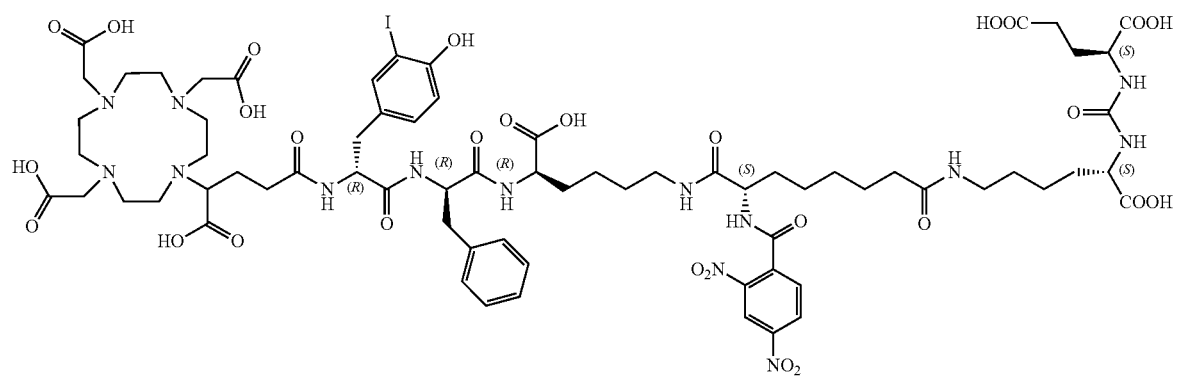

TABLE 3

| PSMA Inhibitor | Configuration | IC$_{50}$ [nM] | Internalization [%] | logP | HSA [%] |
|---|---|---|---|---|---|
| [$^{nat/177}$Lu]PSMA I&T | — | 7.9 ± 2.4* | 75.5 ± 1.6* | −4.12 ± 0.11* | 78.6 |
| [$^{nat/177}$Lu]PSMA-36 | 2,4-DNBA- | 5.3 ± 1.0 | 189.8 ± 37.5 | n.d. | 82.5 |

→ Slightly higher affinity and increase of internalization by 251%.

2. The Binding Motif was Changed from EuK to EuE and the Peptide Spacer from -y(3-I)Fk- to -y-2-Nal-k-

DOTAGA-y(3-I)fk(Sub-KuE) (PSMA I&T)

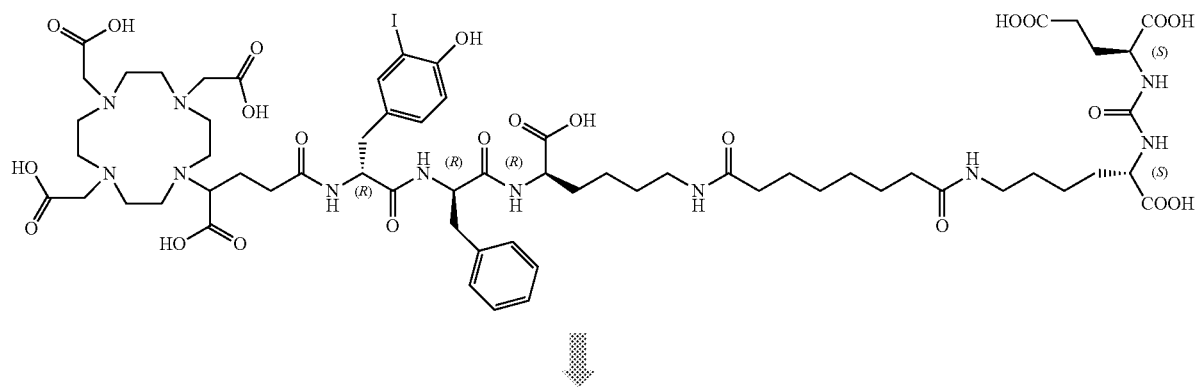

DOTAGA-y-2-nal-k(Suc-N⁵-orn-C⁴-EuE) (PSMA-46)

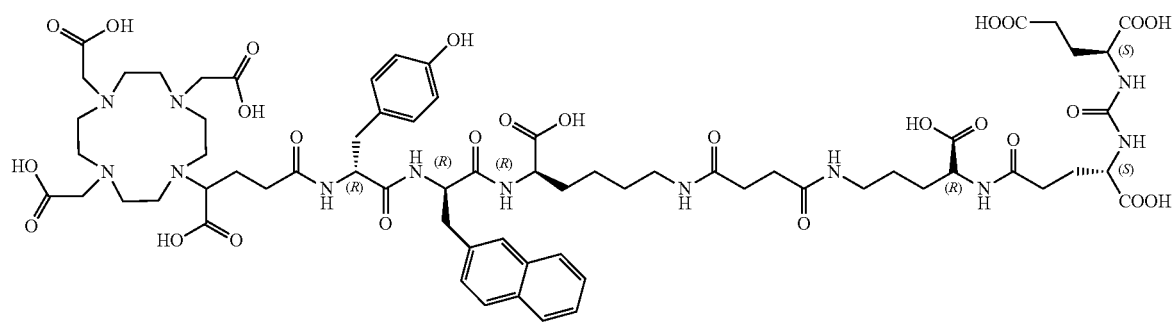

TABLE 4

| PSMA inhibitor | Configuration | IC$_{50}$ [nM] | Internalization [%] | logP | HSA [%] |
|---|---|---|---|---|---|
| [$^{nat/177}$Lu]PSMA I&T | -y(3-I)fk- ∥ -KuE | 7.9 ± 2.4 | 75.5 ± 1.6 | −4.12 ± 0.11 | 78.6 |
| [$^{nat/177}$Lu]PSMA-46 | -y-2-nal-k- ∥ -EuE | 3.2 ± 1.1 | 216.2 ± 9.2 | −4.21 ± 0.08 | 57.7 |

→ Compared to the reference PSMA I&T, the improved reference compound PSMA-46 showed higher internalization and exhibited improved affinity. Thus, based on the structure PSMA-46, electron deficient aromatic residues were introduced in a further development step.

3. 4-Nitrophenylalanine and 2,4-DNBA were Introduced into the Peptide Spacer of PSMA-46
DOTAGA-y-2-nal-k(Suc-N⁵-orn-C⁴-EuE) (PSMA-46)
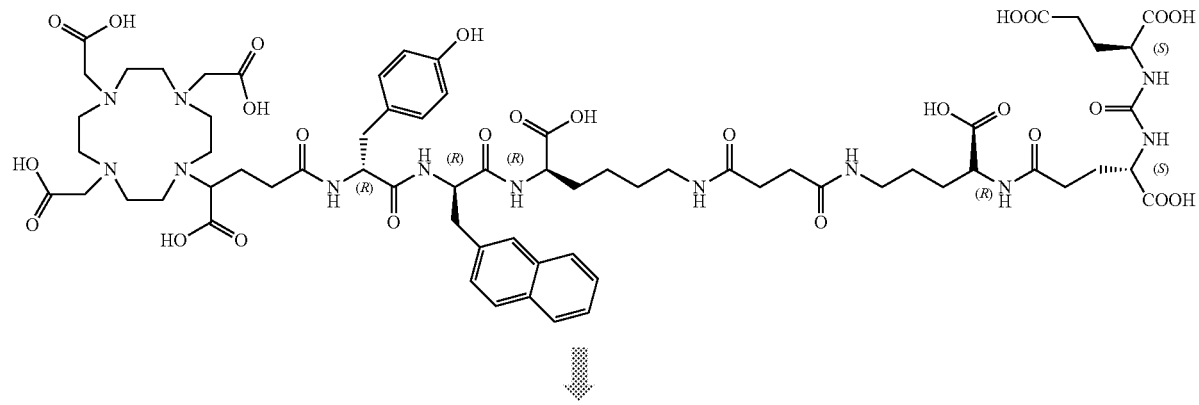
DOTAGA-F(4-NO₂)-y-2-nal-k(Suc-N⁵-orn-C⁴-EuE) (PSMA-52)
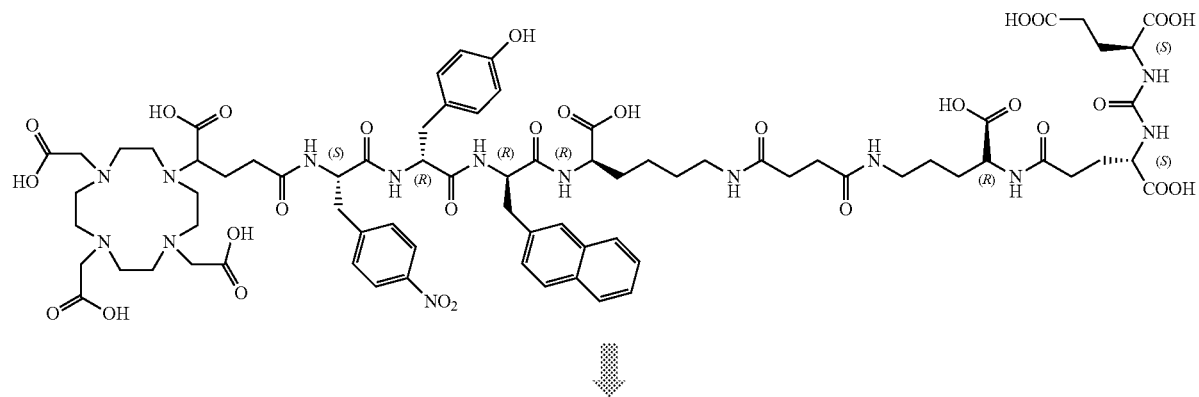
2,4-DNBA-Dap(DOTAGA)-y-2-nal-k(Suc-N⁵-orn-C⁴-EuE)(PSMA-53)
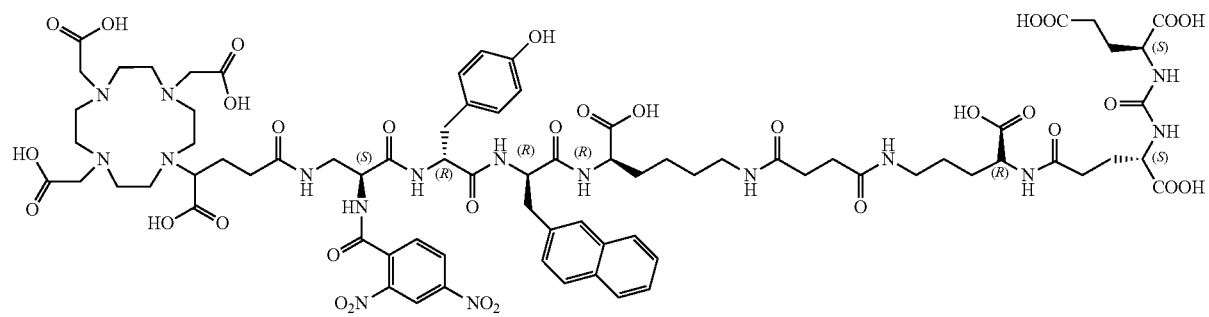

TABLE 5

| PSMA inhibitor | Configuration | IC$_{50}$ [nM] | Internalization [%] | logP | HSA [%] |
|---|---|---|---|---|---|
| [$^{nat/177}$Lu]PSMA-46 | -y-2-nal-k- ‖ -EuE | 3.2 ± 1.1 | 216.2 ± 9.2 | −4.21 ± 0.08 | 57.7 |
| [$^{nat/177}$Lu]PSMA-52 | -F(4-NO$_2$)y-2-nal-k- | 3.4 ± 0.2 | 229.9 ± 8.0 | −4.11 ± 0.07 | 95.4 |
| [$^{nat/177}$Lu]PSMA-53 | 2,4 DNBA-Dap-y-2-nal-k- | 3.2 ± 0.5 | 293.6 ± 10.0 | −4.08 ± 0.04 | 95.9 |

→ While the affinity remained similar, the introduction of 4-nitrophenylalanine increased slightly the internalization, however, by introduction of a further nitro group through 2,4-DNBA, a significant increase of internalization was possible.

→ Two electron withdrawing groups are preferred in order to increase the internalization.

4. Introduction of 4-Amino-Phenylalanine

DOTAGA-F(4-NH$_2$)y-2-nal-k(Suc-N$^5$-orn-C$^4$-EuE) (PSMA-49)

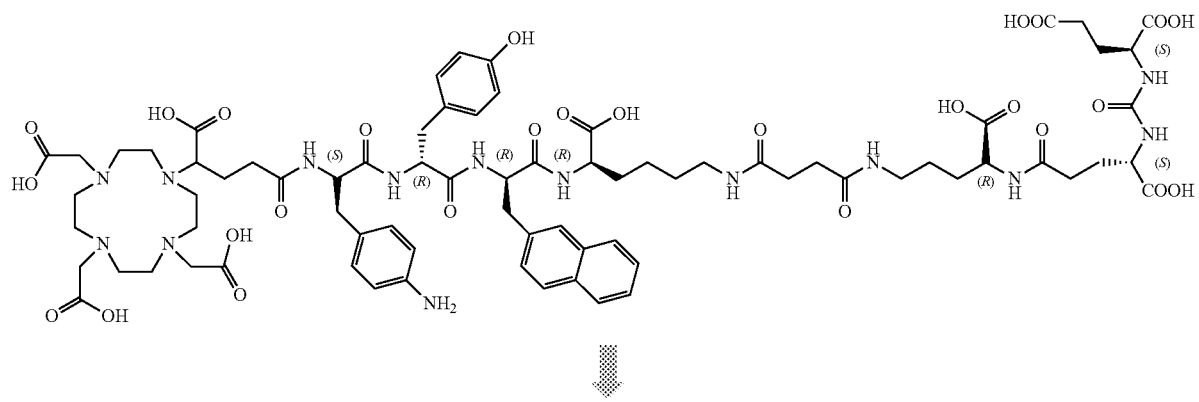

DOTAGA-F(4-NH$_2$)y-2-nal-k(d[N$^5$-orn-C$^4$-EuE]-2,4-DNBA) (PSMA-61)

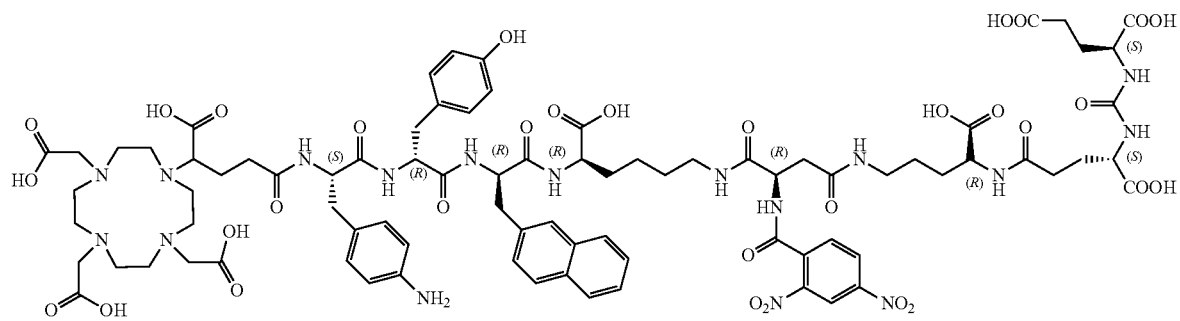

DOTAGA-F(4-NH$_2$)y-2-nal-k(d[N$^5$-orn-C$^4$-EuE]-TMA) (PSMA-62)

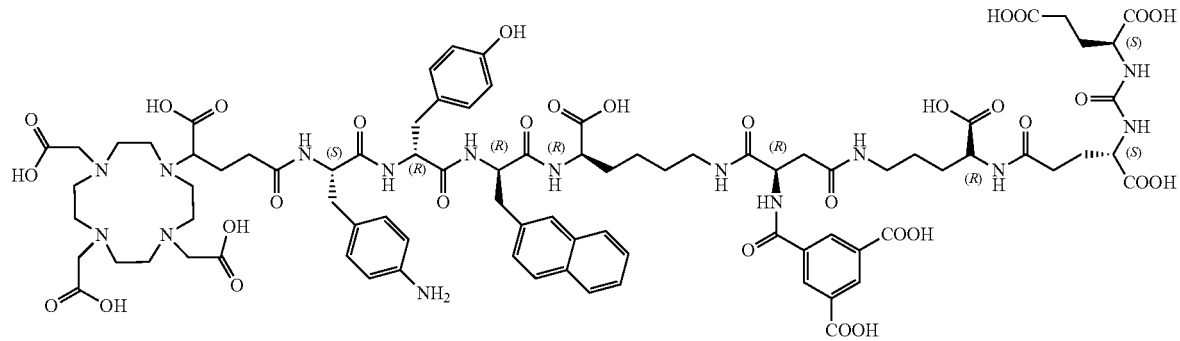

TABLE 6

| PSMA inhibitor | Configuration | IC$_{50}$ [nM] | Internalization [%] | logP | HSA [%] |
|---|---|---|---|---|---|
| [$^{nat/177}$Lu]PSMA I&T | -k(Sub-ε-KuE) | 7.9 ± 2.4 | 75.5 ± 1.6 | −4.12 ± 0.11 | 78.6 |
| [$^{nat/177}$Lu]PSMA-49 | -k(Suc-δ-orn(γ-EuE)) | 2.5 ± 0.6 | 245.0 ± 4.2 | −4.01 ± 0.11 | 74.2 |
| [$^{nat/177}$Lu]PSMA-61 | -k((2,4-DNBA)-d-δ-orn(γ-EuE)) | 4.5 ± 0.4 | 359.5 ± 22.6 | −4.07 ± 0.05 | 63.3 |
| [$^{nat/177}$Lu]PSMA-62 | -k((TMA)-d-δ-orn(γ-EuE)) | 4.0 ± 0.2 | 343.9 ± 6.0 | −4.12 ± 0.05 | >91.0 |

→ Both modifications, 2,4-DNBA and Trimesic acid, were able to further increase the internalization.

5. Introduction of an Electron Deficient Group in the Peptide Spacer

DOTAGA-F(4-NH$_2$)y-2-nal-e(Abz-N$^5$-orn-C$^4$-EuE) (PSMA-60)

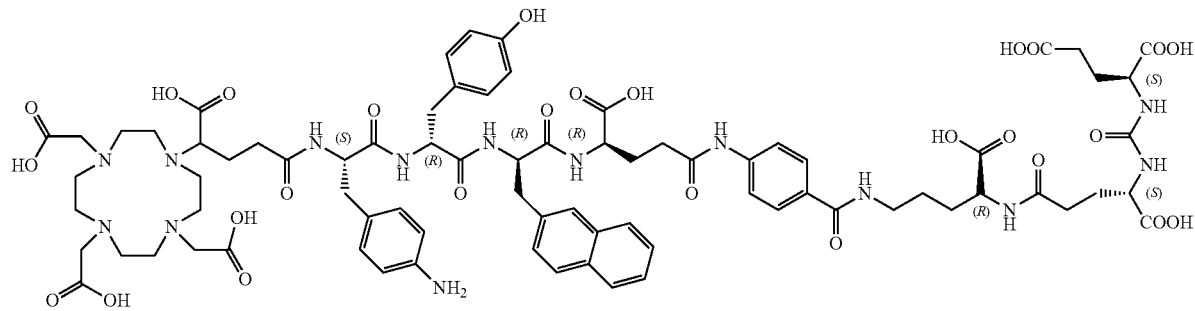

Chemical Formula: C$_{78}$H$_{98}$N$_{14}$O$_{27}$
Molecular Weight: 1663.71

2,4-DNBA-Dap(DOTAGA)y-2-nal-e(Abz-N⁵-orn-C⁴-EuE) (PSMA-65)

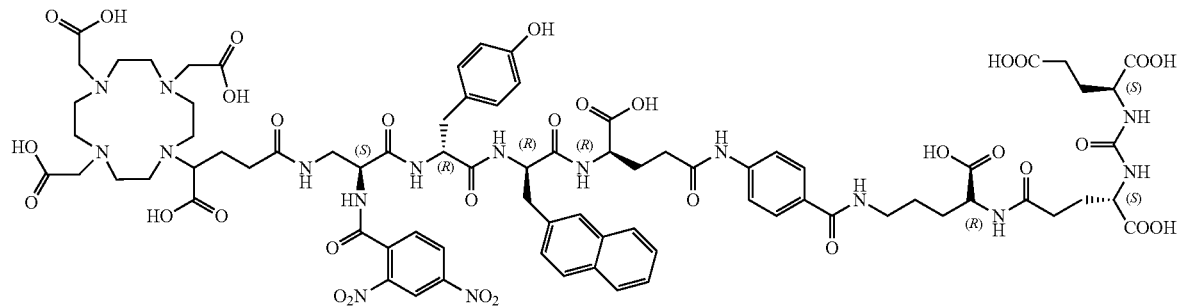

TABLE 7

| PSMA inhibitor | Configuration | IC$_{50}$ [nM] | Internalization [%] | logP | HSA [%] |
|---|---|---|---|---|---|
| [$^{nat/177}$Lu]PSMA-60 | -e(Abz-δ-orn(γ-EuE)) | 6.6 ± 1.5 | 267.4 ± 7.9 | −3.85 ± 0.13 | 98.5 |
| [$^{nat/177}$Lu]PSMA-65 | 2,4-DNBA-Dap(DOTAGA)-y-2-nal-e(Abz-[HO-δ-orn-[γ-EuE]])-OH | 3.5 ± 0.3 | 340.2 ± 18.9 | −4.15 ± 0.08 | 98.7 |

→ The electron deficient aromatic modification 2,4-DNBA was able to increase the internalization.

6. Trimesic Acid was Incorporated into the Linker and Peptide Spacer of the PSMA Inhibitors DOTAGA-F(4-NH$_2$)y-2-nal-k(d[N⁵-orn-C⁴-EuE]-TMA) (PSMA-62)

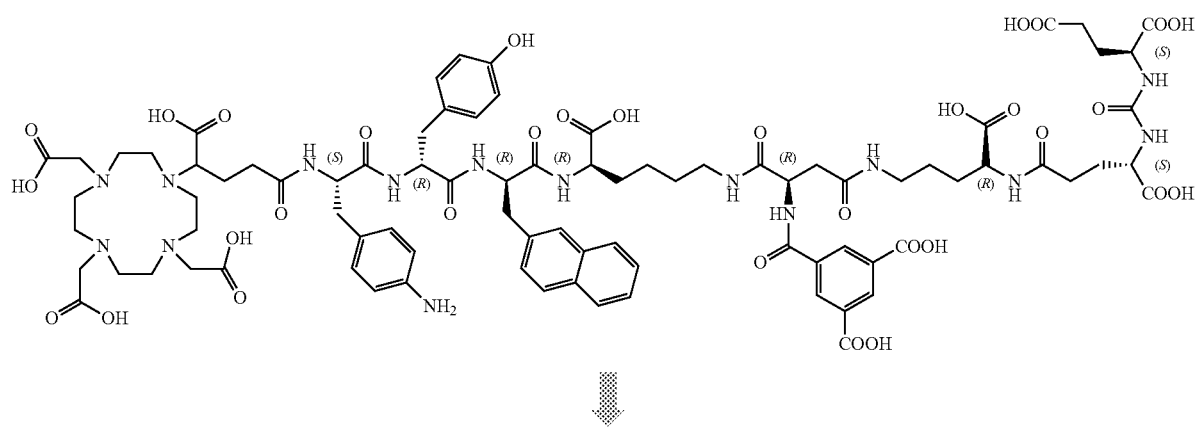

DOTAGA-Dap(TMA)y-2-nal-k(d[N$^5$-orn-C$^4$-EuE]-TMA) (PSMA-66)

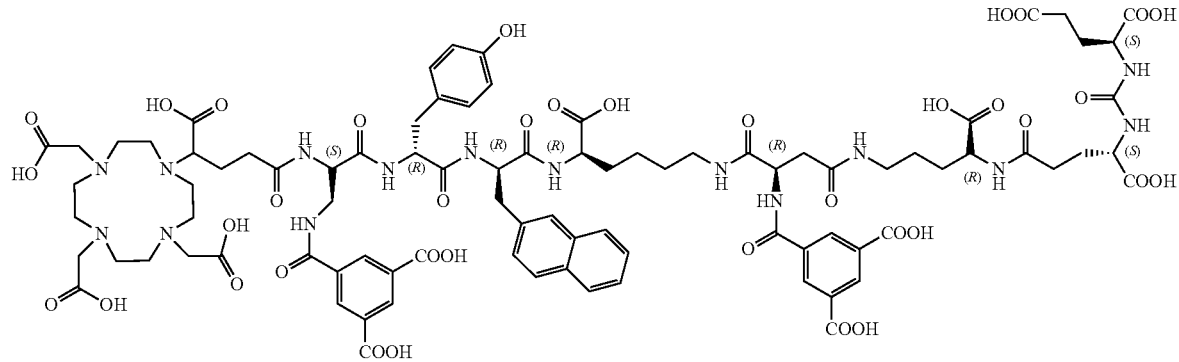

TABLE 8

| PSMA inhibitor | Configuration | IC$_{50}$ [nM] | Internalization [%] | logP | HSA [%] |
|---|---|---|---|---|---|
| [$^{nat/177}$Lu]PSMA I&T | -k(Sub-ε-KuE) | 7.9 ± 2.4* | 75.5 ± 1.6* | −4.12 ± 0.11* | 78.6 |
| [$^{nat/177}$Lu]PSMA-62 | -k((TMA)-d-δ-orn(γ-EuE)) | 4.0 ± 0.2 | 343.9 ± 6.0 | −4.12 ± 0.05 | >91.0 |
| [$^{nat/177}$Lu]PSMA-66 | DOTAGA-Dap(TMA)y-2-nal-k(d[N5-orn-C4-EuE]-TMA) | 3.8 ± 0.3 | 297.8 ± 2.0 | −4.25 ± 0.14 | 64.4 |

→ The exchange of 4-amino-phenylalanine to Dap(TMA) resulted in similar affinity but a slightly reduced internalization capacity. Since both ligands seemed highly promising, both tracer were evaluated in further experiments.

→ The conclusion from these experiments is that an electron deficient aromatic residue is transferable and able to increase the internalization while maintaining a high affinity.

7. The Influence of Internalization on the Cell Retention In Vitro was Evaluated for the Compounds [$^{177}$Lu]PSMA-62 and [$^{177Lu}$]PSMA-66 in Comparison to [$^{177}$Lu]PSMA I&T and [$^{177}$Lu]PSMA-617

[$^{177}$Lu]PSMA-66 demonstrated the highest intracellular activity in the tumor cells after 1 h followed by [$^{177}$Lu]PSMA-62, although the internalization of [$^{177}$Lu]PSMA-62 was found to be higher than for [$^{177}$Lu]PSMA-66 (343.9% vs. 297.8%; respectively). Interestingly, even when re-internalization was blocked with 100 µM 2-PMPA-solution, the intracellular clearance [$^{177}$Lu]PSMA-66 was lower than for all other investigated compounds. The difference compared to reference [$^{177}$Lu]PSMA I&T was more than twofold, if re-internalization was blocked.

[$^{177}$Lu]PSMA-66 has nine free carboxylic groups, which equal nine negative charges in vivo (pH=7.4). The extensively charged character of this compound could be a possible explanation for the protracted intracellular retention due to electrostatic repulsive effects from the negatively charged cell membranes.

8. In Vivo Experiments: Biodistribution

TABLE 9

Biodistribution data of [$^{177}$Lu]PSMA-49, [$^{177}$Lu]PSMA-62 and [$^{177}$Lu]PSMA-66 (in % ID/g) in LNCaP-tumor xenograft bearing CB-17 SCID mice at 1 h p.i. (n = 4, respectively). Between 3.5 MBq and 5.5 MBq of the respective $^{177}$Lu-labeled radioligand were injected (0.15 to 0.25 nmol tracer).

| | [$^{177}$Lu]PSMA I&T 1 h p.i. | [$^{177}$Lu]PSMA-49 1 h p.i. | [$^{177}$Lu]PSMA-62 1 h p.i. | [$^{177}$Lu]PSMA-66 1 h p.i. |
|---|---|---|---|---|
| blood | 0.37 ± 0.10 | 0.46 ± 0.06 | 0.52 ± 0.03 | 0.50 ± 0.03 |
| heart | 0.58 ± 0.15 | 0.57 ± 0.11 | 0.58 ± 0.06 | 0.49 ± 0.06 |
| lung | 1.32 ± 0.45 | 1.47 ± 0.25 | 0.87 ± 0.11 | 0.62 ± 0.12 |
| liver | 0.37 ± 0.10 | 0.99 ± 0.19 | 0.37 ± 0.04 | 0.32 ± 0.02 |
| spleen | 13.8 ± 4.59 | 20.53 ± 6.79 | 4.62 ± 1.81 | 1.93 ± 0.04 |
| pancreas | 1.30 ± 1.39 | 0.56 ± 0.07 | 0.18 ± 0.05 | 0.15 ± 0.04 |
| stomach | 0.29 ± 0.06 | 0.35 ± 0.10 | 0.51 ± 0.2 | 0.28 ± 0.04 |
| intestine | 0.59 ± 0.50 | 0.30 ± 0.08 | 0.49 ± 0.25 | 0.21 ± 0.03 |
| kidney | 128.90 ± 10.74 | 162.96 ± 23.20 | 106.45 ± 17.18 | 117.47 ± 6.86 |

TABLE 9-continued

Biodistribution data of [$^{177}$Lu]PSMA-49, [$^{177}$Lu]PSMA-62 and [$^{177}$Lu]PSMA-66 (in % ID/g) in LNCaP-tumor xenograft bearing CB-17 SCID mice at 1 h p.i. (n = 4, respectively). Between 3.5 MBq and 5.5 MBq of the respective $^{177}$Lu-labeled radioligand were injected (0.15 to 0.25 nmol tracer).

|  | [$^{177}$Lu]PSMA I&T 1 h p.i. | [$^{177}$Lu]PSMA-49 1 h p.i. | [$^{177}$Lu]PSMA-62 1 h p.i. | [$^{177}$Lu]PSMA-66 1 h p.i. |
|---|---|---|---|---|
| adrenal gland | 6.25 ± 2.59 | 5.66 ± 1.66 | 1.92 ± 0.80 | 0.78 ± 0.07 |
| muscle | 0.18 ± 0.07 | 0.17 ± 0.02 | 0.12 ± 0.03 | 0.19 ± 0.07 |
| bone | 0.14 ± 0.04 | 0.29 ± 0.14 | 0.30 ± 0.08 | 0.37 ± 0.13 |
| brain | 0.03 ± 0.01 | 0.03 ± 0.01 | 0.03 ± 0.01 | 0.02 ± 0.01 |
| tumor | 4.69 ± 0.95 | 8.21 ± 0.23 | 8.00 ± 0.78 | 10.00 ± 0.44 |
| tumor/blood | 12.7 | 17.8 | 15.4 | 20.0 |
| tumor/kidney | 0.04 | 0.05 | 0.08 | 0.09 |
| tumor/muscle | 26.1 | 48.3 | 66.7 | 52.6 |

Compared to the tumor uptake of [$^{177}$Lu]PSMA I&T after 1 h p.i. (4.69±0.95%), a significant increase in tumor activity was achieved through the improvement of internalization and affinity. As already observed for [$^{177}$Lu]PSMA-16, [$^{177}$Lu]PSMA-40 and [$^{177}$Lu]PSMA-41, the extension of the peptide spacer with 4-amino-D-phenylalanine led to high kidney uptake and confirmed that this modification increases renal accumulation.

The introduction of trimesic acid into the linker of [$^{177}$Lu]PSMA-62 led to a reduction of renal uptake (106.45±17.18% vs. 162.96±23.20%, respectively) and slightly lower tumor uptake compared to the reference. Since the internalization for [$^{177}$Lu]PSMA-62 was higher in direct comparison to [$^{177}$Lu]PSMA-49, the lower tumor uptake was unexpected. It is unclear to what extent internalization contributes to tumor uptake and if it is less important than affinity. The direct comparison of [$^{177}$Lu]PSMA-49 and [$^{177}$Lu]PSMA-62 indicates that affinity is more crucial since [$^{177}$Lu]PSMA-49 was more affine towards PSMA (2.5±0.6 nM vs. 4.0±0.2 nM, respectively).

pared to 1 h p.i. (Table 9) was observed. While [$^{177}$Lu]PSMA I&T demonstrated after 24 h p.i. the highest renal uptake, [$^{177}$Lu]PSMA-62 showed the lowest, which is in concordance to the observed renal clearance in the PET-study. The tumor uptake of [$^{177}$Lu]PSMA-61 after 24 h p.i. remained almost stable over 23 h (8.00±0.75 vs. 7.70±1.35% ID/g, 1 h p.i. and 24 h p.i., respectively). Although [$^{177}$Lu]PSMA-62 and [$^{177}$Lu]PSMA-66 demonstrated similar in vitro parameter regarding internalization and affinity, the tumor uptake of [$^{177}$Lu]PSMA-66 decreased to a greater extent from 1 h p.i. to 24 h p.i. (10.00±0.44 vs. 5.73±1.39% ID/g, 1 h p.i. and 24 h p.i., respectively) compared to [$^{177}$Lu]PSMA-62. The stronger tumor retention together with the more beneficial tumor to liver and tumor to muscle ratios render [$^{177}$Lu]PSMA-62 superior compared to [$^{177}$Lu]PSMA-66. The highest tumor uptake was observed for PSMA-71, which also exhibited the highest HSA-binding value. While the kidney uptake 24 h p.i. was similar to

TABLE 10

Biodistribution data of [$^{177}$Lu]PSMA I&T, [$^{177}$Lu]PSMA-62 and [$^{177}$Lu]PSMA-66 and [$^{177}$Lu]PSMA-71 (in % ID/g) in LNCaP-tumor xenograft bearing CB-17 SCID mice after 24 h p.i. (n = 4, respectively). Between 3.5 MBq and 5.5 MBq of the respective $^{177}$Lu-labeled radioligand were injected (0.15 to 0.25 nmol tracer).

|  | [$^{177}$Lu]PSMA I&T 24 h p.i. | [$^{177}$Lu]PSMA-62 24 h p.i. | [$^{177}$Lu]PSMA-66 24 h p.i. * | [$^{177}$Lu]PSMA-71 24 h p.i. |
|---|---|---|---|---|
| blood | 0.012 ± 0.01 | 0.004 ± 0.001 | 0.003 ± 0.001 | 0.008 ± 0.001 |
| heart | 0.05 ± 0.03 | 0.02 ± 0.01 | 0.03 ± 0.007 | 0.07 ± 0.01 |
| lung | 0.16 ± 0.03 | 0.03 ± 0.02 | 0.03 ± 0.007 | 0.05 ± 0.01 |
| liver | 0.05 ± 0.01 | 0.17 ± 0.07 | 0.14 ± 0.02 | 0.38 ± 0.14 |
| spleen | 1.94 ± 1.01 | 0.09 ± 0.06 | 0.09 ± 0.02 | 0.27 ± 0.15 |
| pancreas | 0.05 ± 0.02 | 0.01 ± 0.002 | 0.02 ± 0.007 | 0.15 ± 0.15 |
| stomach | 0.05 ± 0.02 | 0.03 ± 0.01 | 0.07 ± 0.03 | 0.20 ± 0.10 |
| intestine | 0.12 ± 0.06 | 0.03 ± 0.02 | 0.11 ± 0.07 | 0.27 ± 015 |
| kidney | 34.66 ± 17.20 | 5.26 ± 1.58 | 20.92 ± 2.51 | 32.36 ± 2.49 |
| adrenal g. | 1.06 ± 0.24 | 0.04 ± 0.02 | 0.09 ± 0.09 | 0.32 ± 0.15 |
| muscle | 0.01 ± 0.01 | 0.007 ± 0.001 | 0.02 ± 0.006 | 0.01 ± 0.001 |
| bone | 0.01 ± 0.01 | 0.04 ± 0.006 | 0.02 ± 0.01 | 0.04 ± 0.02 |
| brain | 0.02 ± 0.01 | 0.01 ± 0.006 | 0.01 ± 0.001 | 0.01 ± 0.002 |
| tumor | 4.06 ± 1.12 | 7.70 ± 1.35 | 5.73 ± 1.39 | 14.29 ± 0.89 |
| t/blood | 406 | 1925.0 | 1910.0 | 1786.3 |
| t/kidney | 0.1 | 1.5 | 0.3 | 0.4 |
| t/muscle | 406 | 1100.0 | 286.5 | 1429.0 |
| t/liver | 81.2 | 45.3 | 40.9 | 37.6 |

The results in Table 10 show distinct differences between the evaluated tracer [$^{177}$Lu]PSMA-62, [$^{177}$Lu]PSMA-66 and [$^{177}$Lu]PSMA-71. Regarding renal clearance, it was visible that for all ligands a decrease in renal uptake compared to [$^{177}$Lu]PSMA I&T, the tumor uptake was more than three-fold higher for [$^{177}$Lu]PSMA-71 (4.06±1.12 vs. 14.29±0.89% ID/g, [$^{177}$Lu]PSMA I&T and [$^{177}$Lu]PSMA-71, respectively).

In this respect, [$^{177}$Lu]PSMA-71 may be considered as a particularly valuable tracer for endoradiotherapeutic application and is a candidate for clinical application.

9. In Vivo Experiments: PET-Imaging

Effect of 2,4-Dinitrobenzoic Linker Substitution on EuK-Based Inhibitors

The EuK-based inhibitor PSMA-36 was evaluated in a small animal PET scan to examine the influence of the 2,4-dinitrobenzoic acid in the linker on the in vivo distribution.

The logarithmic TACs plot shows specific kidney and tumor uptake of [$^{68}$Ga]PSMA-36. Linear decrease of the blood pool activity and in the muscle region imply low unspecific binding and fast excretion. Accumulation in the tumor remained steady over the observed period. Although [$^{177}$Lu]PSMA-36 exhibited a more than threefold higher internalization rate than [$^{177}$Lu]PSMA I&T, tumor uptake was only moderate with 3.5% ID/mL after 85 min p.i. The most significant difference compared to [$^{68}$Ga]PSMA I&T was the high and steady uptake in the lacrimal and salivary gland, displaying approx. 2% ID/mL in both regions. Since the only structural difference to the reference [$^{68}$Ga]PSMA I&T is the introduction of 2,4-dinitrobenzoic acid, the linker modification must be the reason for this enhanced uptake. However, further studies are necessary to confirm this effect.

It is also interesting, that the clearance in these regions was slower compared to the blood pool and muscle, which implies that a distinct retaining mechanism is involved. It was reported that PSMA participates in angiogenesis during ocular neovascularization in mice and might therefore explain the uptake of [$^{68}$Ga]PSMA-36 [1]. Tracer accumulation in the salivary glands is a common problem during clinical therapeutic approaches with $^{177}$Lu-labeled PSMA inhibitors [2]. Drug uptake into the salivary glands depends on intra- or extracellular pathways and most commonly on simple diffusion among the phospholipid bilayer of the acinar cells. Saliva drug concentrations are reflected predominantly by the free, non-ionized fraction in the blood plasma regarding passive diffusion [3-5]. In this respect, it seems highly unlikely that passive diffusion is responsible for the salivary gland uptake. Other mechanisms have to be involved since EuK-based PSMA inhibitors are highly charged in vivo and thus exhibit high polarity. Further, passive diffusion would be visualized during PET scans in every region as high background activity, which does not occur for most PSMA ligands since the rapid clearance removes the tracer from the blood pool.

Effect of Trimesic Acid on EuE-Based Inhibitors

Substitution of the PSMA ligands with electron deficient aromatic systems resulted in enhanced internalization rates of [$^{177}$Lu]PSMA-62 and [$^{177}$Lu]PSMA-66 (343.9% and 297.8%, respectively). Both ligands were therefore evaluated and compared among each other in PET studies.

Both tracer exhibited excellent tracer kinetics regarding kidney, muscle and blood pool uptake. Specific uptake in the kidneys was slightly higher for [$^{68}$Ga]PSMA-66 compared to [$^{68}$Ga]PSMA-62 (45.3% ID/mL vs. 34.8% ID/mL, respectively). The higher renal accumulation in the PET scan of [$^{68}$Ga]PSMA-66 compared to [$^{68}$Ga]PSMA-62 nicely correlated with the biodistribution experiments. TACs for muscle and blood pool activity showed linear uptake and ongoing clearance from these compartments.

10. References in Example 2

1. Grant, C. L., et al., *Prostate specific membrane antigen (PSMA) regulates angiogenesis independently of VEGF during ocular neovascularization*. PloS one, 2012. 7(7): p. e41285.
2. Kulkarni, H. R., et al., *PSMA-Based Radioligand Therapy for Metastatic Castration-Resistant Prostate Cancer: The Bad Berka Experience Since 2013*. Journal of Nuclear Medicine, 2016. 57(Supplement 3): p. 97S-104S.
3. Haeckel, R., *Factors influencing the saliva/plasma ratio of drugs*. Annals of the New York Academy of Sciences, 1993. 694(1): p. 128-142.
4. Jusko, W. J. and R. L. Milsap, *Pharmacokinetic Principles of Drug Distribution in Salivaa*. Annals of the New York Academy of Sciences, 1993. 694(1): p. 36-47.
5. Aps, J. K. and L. C. Martens, *Review: the physiology of saliva and transfer of drugs into saliva*. Forensic science international, 2005. 150(2): p. 119-131.
6. Young, J. D., et al., *68Ga-THP-PSMA: a PET imaging agent for prostate cancer offering rapid, room temperature, one-step kit-based radiolabeling*. Journal of Nuclear Medicine, 2017: p. jnumed. 117.191882.
7. Wüstemann, T., et al., *Design of Internalizing PSMA-specific Glu-ureido-based Radiotherapeuticals*. Theranostics, 2016. 6(8): p. 1085.
8. Hao, G., et al., *A multivalent approach of imaging probe design to overcome an endogenous anion binding competition for noninvasive assessment of prostate specific membrane antigen*. Molecular pharmaceutics, 2013. 10(8): p. 2975-2985.
9. Soret, M., S. L. Bacharach, and I. Buvat, *Partial-volume effect in PET tumor imaging*. Journal of Nuclear Medicine, 2007. 48(6): p. 932-945.
10. Bao, Q., et al., *Performance evaluation of the inveon dedicated PET preclinical tomograph based on the NEMA NU-4 standards*. Journal of Nuclear Medicine, 2009. 50(3): p. 401-408.

The invention claimed is:

1. A compound or salt that comprises a structure of one of the following formulae:

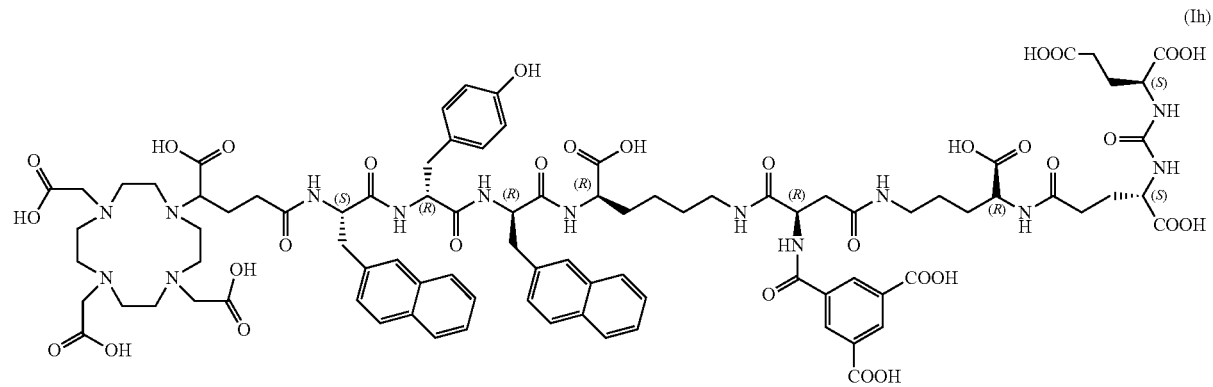

(Ih)

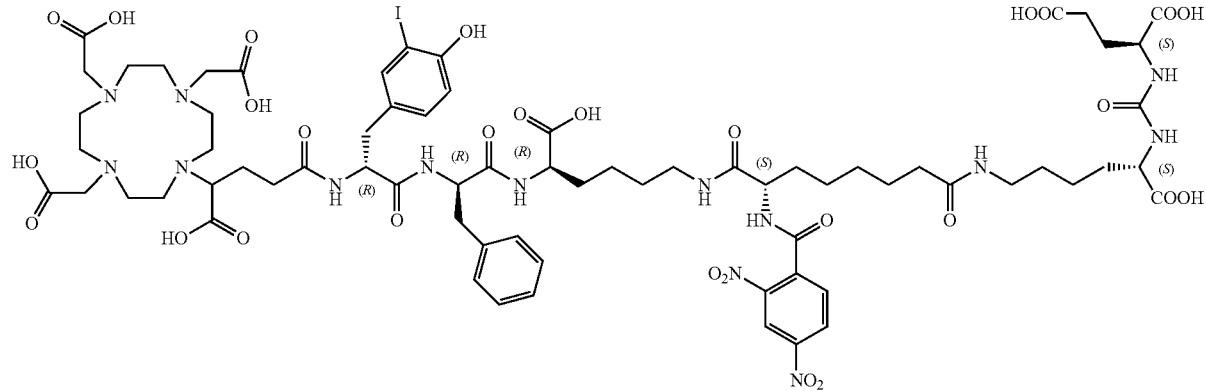
(Ii)
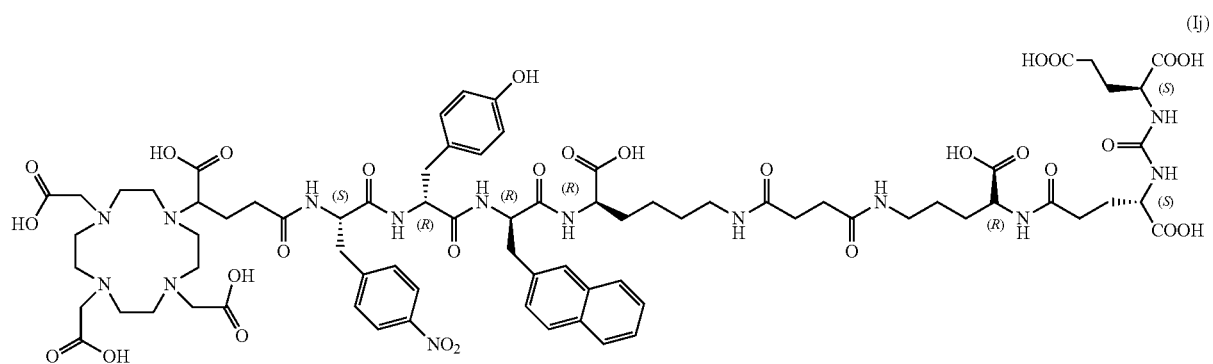
(Ij)
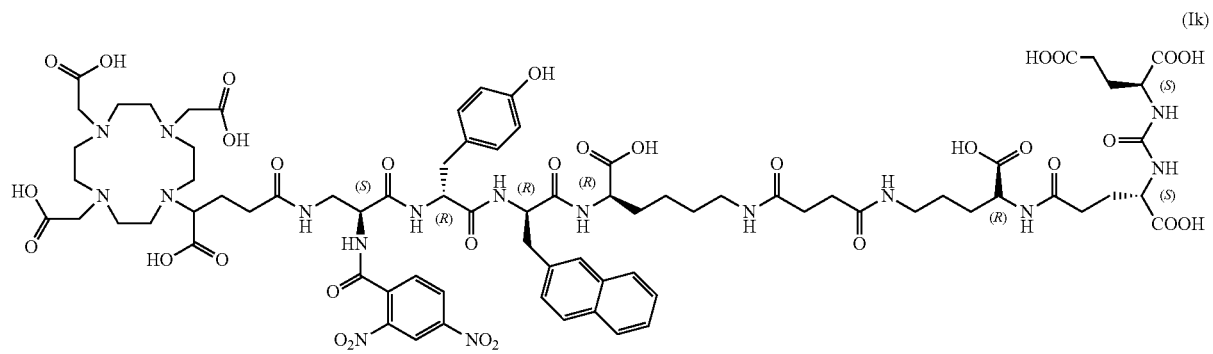
(Ik)
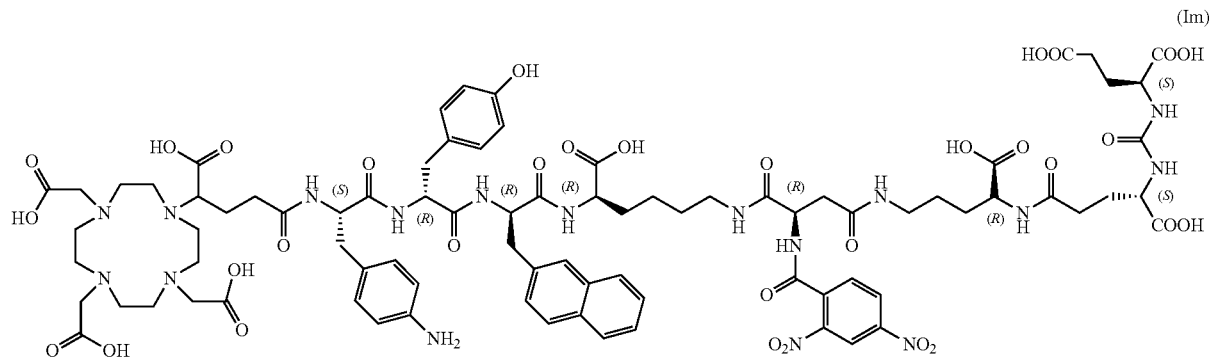
(Im)

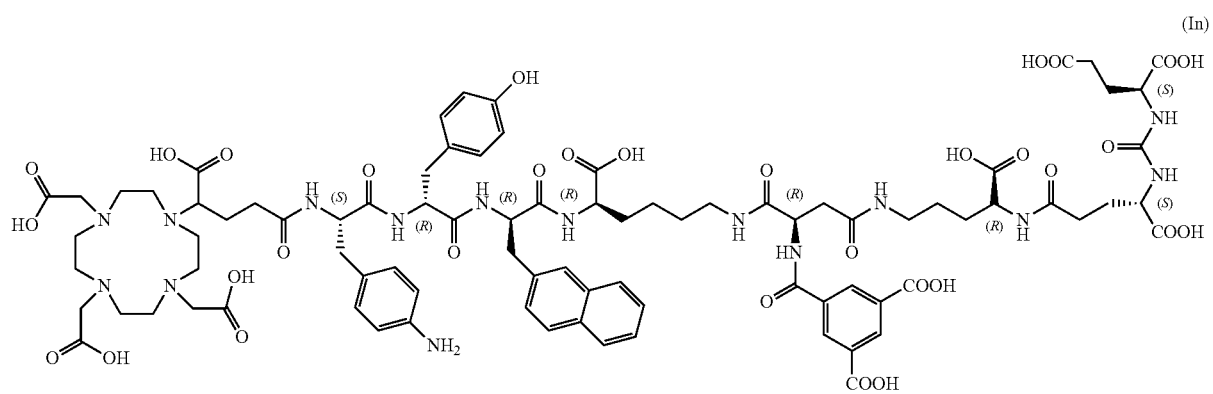
(In)
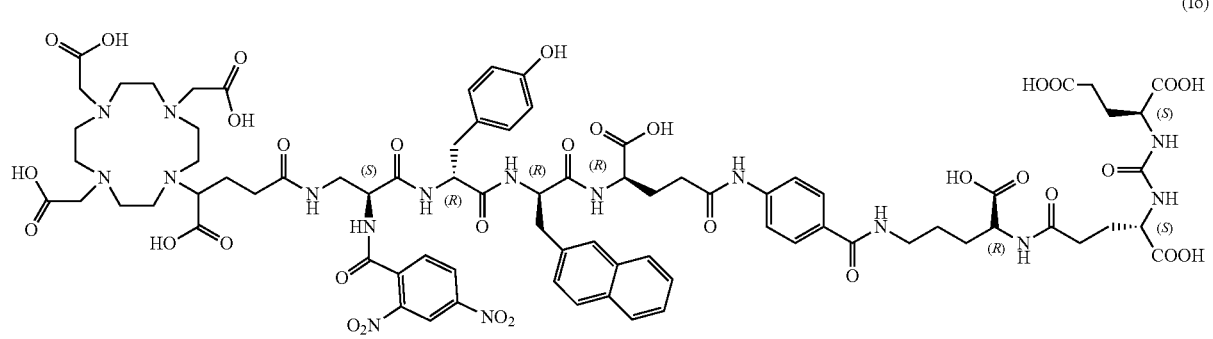
(Io)
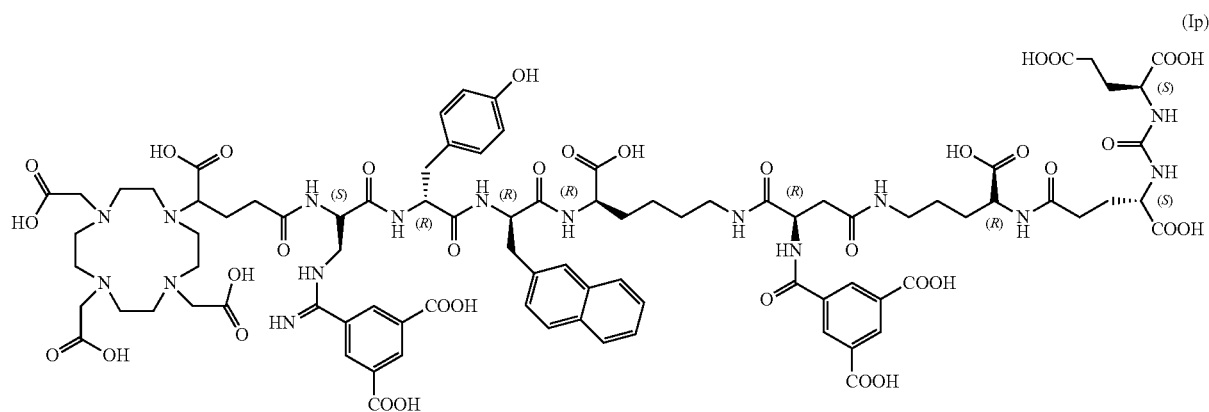
(Ip)
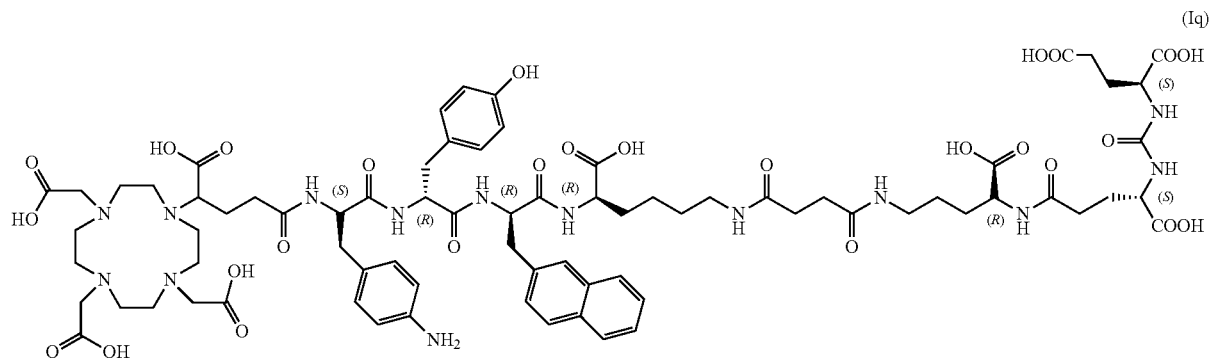
(Iq)

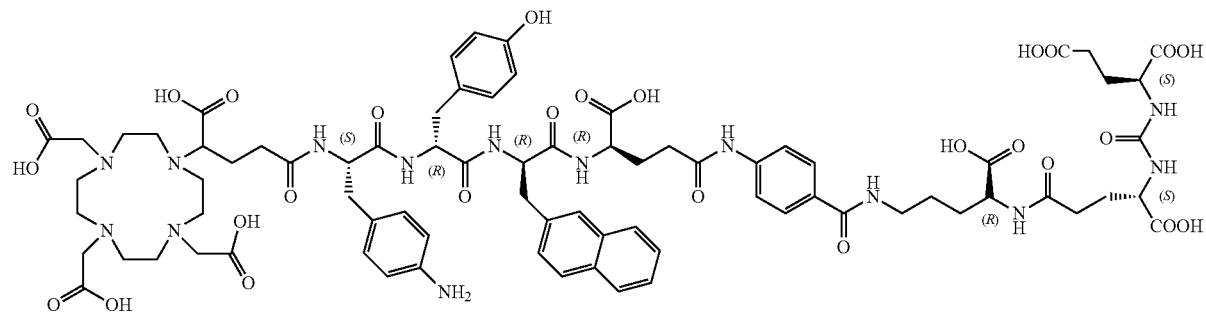
(Ir)
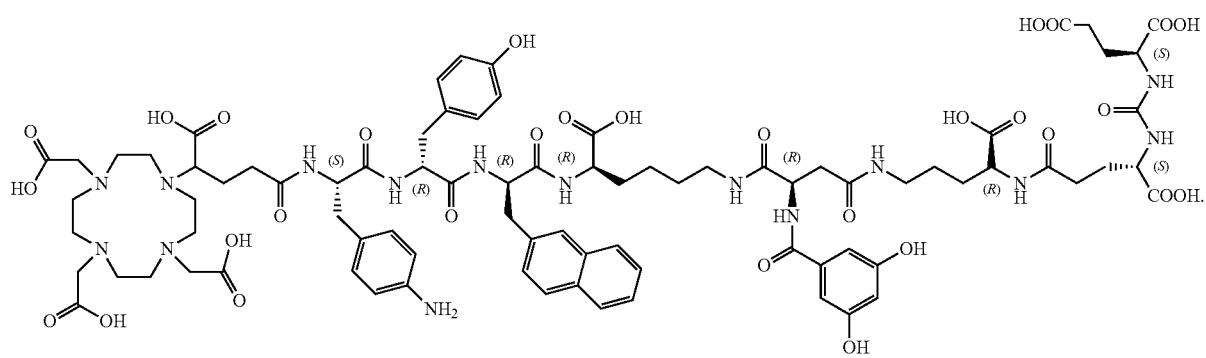
(Is)
2. A compound of claim 1 that comprises a structure of the following formula:
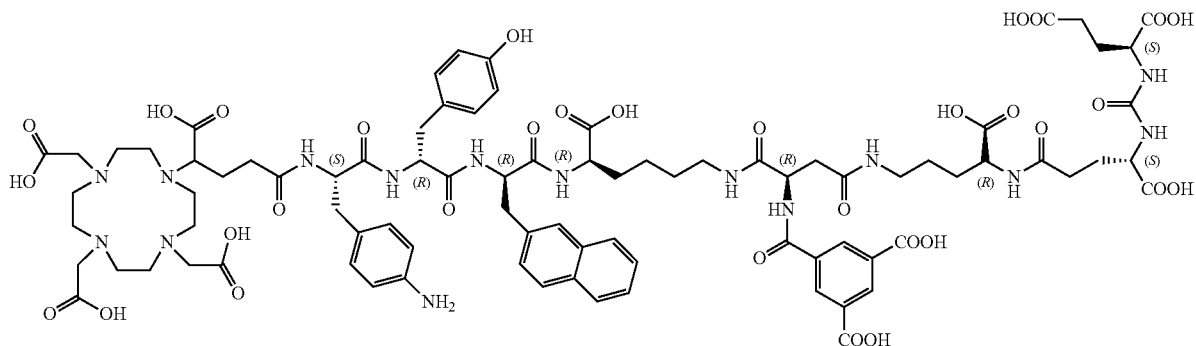
or salt thereof.

3. A compound of claim 1 that comprises a structure of the following formula:

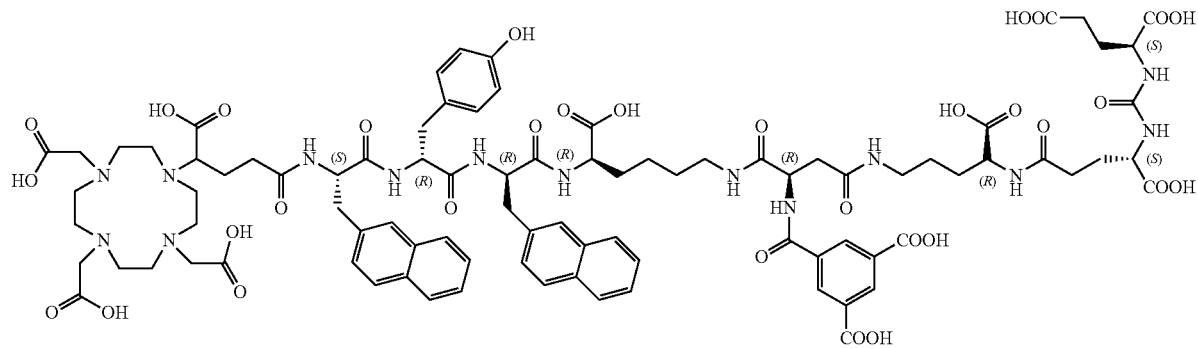

or salt thereof.

4. A compound of claim 1 that comprises a structure of the following formula:

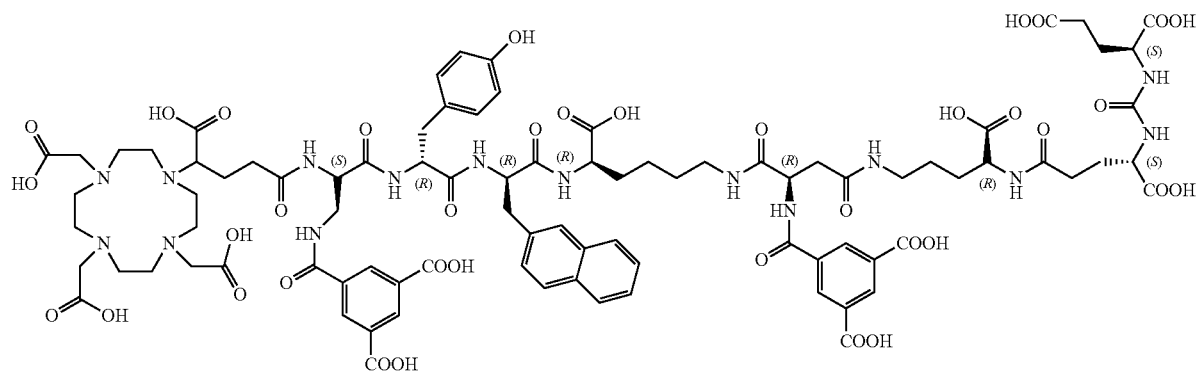

or salt thereof.

5. A compound of claim 1 that comprises a structure of the following formula:

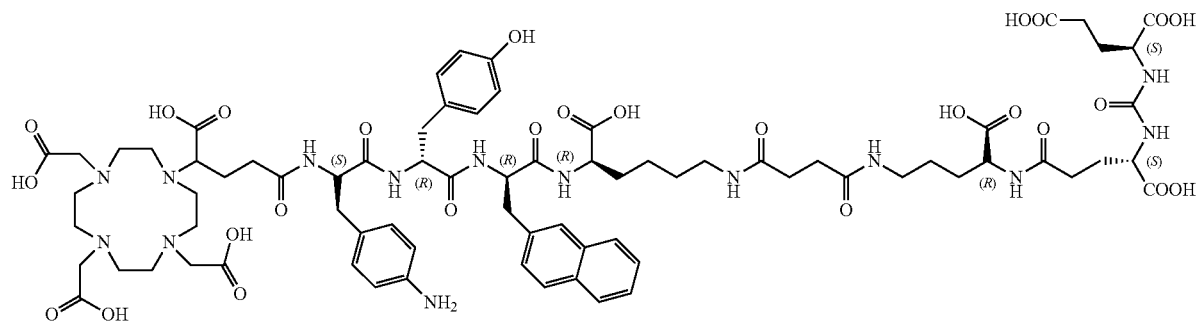

or salt thereof.

6. A compound of claim 1 comprising a radioactive cation.

7. A compound of claim 6 comprising $^{177}$Lu.

8. A compound of claim 2 comprising a radioactive cation.

9. A compound of claim 8 comprising $^{177}$Lu.

10. A compound of claim 3 comprising a radioactive cation.

11. A compound of claim 10 comprising $^{177}$Lu.

12. A compound of claim 4 comprising a radioactive cation.

13. A compound of claim 12 comprising $^{177}$Lu.

14. A compound of claim 5 comprising a radioactive cation.

15. A compound of claim 14 comprising $^{177}$Lu.

16. A pharmaceutical composition comprising one or more compounds or salts of claim 1.

17. A pharmaceutical composition comprising one or more compounds or salts of claim 6.

18. A method for treating prostate-specific membrane antigen (PSMA)-associated cancer in a subject, comprising administering to the subject an effective amount of the composition of claim 6.

19. A method for treating prostate-specific membrane antigen (PSMA)-associated cancer in a subject, comprising administering to the subject an effective amount of the composition of claim 7.

20. A method for treating prostate-specific membrane antigen (PSMA)-associated cancer in a subject, comprising administering to the subject an effective amount of the composition of claim 8.

21. A method for treating prostate-specific membrane antigen (PSMA)-associated cancer in a subject, comprising administering to the subject an effective amount of the composition of claim 9.

22. A method for treating prostate-specific membrane antigen (PSMA)-associated cancer in a subject, comprising administering to the subject an effective amount of the composition of claim 10.

23. A method for treating prostate-specific membrane antigen (PSMA)-associated cancer in a subject, comprising administering to the subject an effective amount of the composition of claim 11.

24. A method for treating prostate-specific membrane antigen (PSMA)-associated cancer in a subject, comprising administering to the subject an effective amount of the composition of claim 12.

25. A method for treating prostate-specific membrane antigen (PSMA)-associated cancer in a subject, comprising administering to the subject an effective amount of the composition of claim 13.

26. A method for treating prostate-specific membrane antigen (PSMA)-associated cancer in a subject, comprising administering to the subject an effective amount of the composition of claim 14.

27. A method for treating prostate-specific membrane antigen (PSMA)-associated cancer in a subject, comprising administering to the subject an effective amount of the composition of claim 15.

28. A method for treating prostate cancer in a subject, comprising administering to the subject an effective amount of the composition of claim 6.

29. A method for treating prostate cancer in a subject, comprising administering to the subject an effective amount of the composition of claim 7.

30. A method for treating prostate cancer in a subject, comprising administering to the subject an effective amount of the composition of claim 8.

31. A method for treating prostate cancer in a subject, comprising administering to the subject an effective amount of the composition of claim 9.

32. A method for treating prostate cancer in a subject, comprising administering to the subject an effective amount of the composition of claim 10.

33. A method for treating prostate cancer in a subject, comprising administering to the subject an effective amount of the composition of claim 11.

34. A method for treating prostate cancer in a subject, comprising administering to the subject an effective amount of the composition of claim 12.

35. A method for treating prostate cancer in a subject, comprising administering to the subject an effective amount of the composition of claim 13.

36. A method for treating prostate cancer in a subject, comprising administering to the subject an effective amount of the composition of claim 14.

37. A method for treating prostate cancer in a subject, comprising administering to the subject an effective amount of the composition of claim 15.

\* \* \* \* \*